(12) United States Patent
Lewis et al.

(10) Patent No.: US 6,331,244 B1
(45) Date of Patent: Dec. 18, 2001

(54) SENSORS FOR DETECTING ANALYTES IN FLUIDS

(75) Inventors: Nathan S. Lewis, La Canada; Erik Severin, Pasadena, both of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/478,680

(22) Filed: Jan. 6, 2000

Related U.S. Application Data

(63) Continuation of application No. 09/258,713, filed on Feb. 26, 1999, now Pat. No. 6,093,308, which is a continuation of application No. 08/949,730, filed on Oct. 14, 1997, now Pat. No. 5,911,872, which is a continuation of application No. 08/696,128, filed on Aug. 14, 1996, now Pat. No. 5,788,833, which is a continuation-in-part of application No. 08/410,809, filed on Mar. 27, 1995, now Pat. No. 5,571,401.

(51) Int. Cl.$^7$ .................................................. G01N 27/26

(52) U.S. Cl. .................. 205/777.5; 204/403; 422/82.01; 422/82.02; 436/150

(58) Field of Search ................................ 205/787, 782.5, 205/775, 777.5; 204/406, 415, 418, 403; 422/68.1, 69, 82.01, 82.02; 436/150

(56) References Cited

U.S. PATENT DOCUMENTS

| | | |
|---|---|---|
| 3,045,198 | 7/1962 | Dolan et al. ............................ 338/13 |
| 3,428,892 | 2/1969 | Meinhard ................................ 324/71 |
| 3,970,863 | 7/1976 | Kishikawa et al. ................... 307/116 |
| 3,999,122 | 12/1976 | Winstel et al. ....................... 324/715 N |
| 4,142,400 | 3/1979 | Colla et al. .............................. 73/23 |
| 4,225,410 | 9/1980 | Pace .................................. 204/195 R |
| 4,236,307 | 12/1980 | Colla et al. ............................. 29/857 |
| 4,322,383 | 3/1982 | Yasuda et al. .......................... 422/95 |
| 4,457,161 | 7/1984 | Iwanaga et al. ......................... 73/23 |
| 4,542,640 | 9/1985 | Cliffford ................................ 73/23 |
| 4,631,952 | 12/1986 | Donaghey ............................... 73/23 |
| 4,674,320 | 6/1987 | Hirchfeld ................................ 73/23 |
| 4,759,210 | 7/1988 | Wohltjen ............................... 422/88 |
| 4,795,968 | 1/1989 | Madou et al. .......................... 324/61 |
| 4,812,221 | 3/1989 | Madou et al. ........................ 204/412 |
| 4,847,783 | 7/1989 | Grace et al. .......................... 364/497 |
| 4,855,706 | 8/1989 | Hauptly ................................ 338/34 |
| 4,884,435 | 12/1989 | Ehara .................................... 73/23 |
| 4,893,108 | 1/1990 | Kolesar, Jr. ............................ 338/34 |
| 4,900,405 | 2/1990 | Otagawa et al. ....................... 204/23 |
| 4,907,441 | 3/1990 | Shurmer ................................ 73/34 |
| 4,911,892 | 3/1990 | Grace et al. ......................... 422/1 T |
| 4,926,156 | 5/1990 | Dickert et al. ......................... 338/23 |
| 4,992,244 | 2/1991 | Grate .................................... 422/94 |
| 5,023,133 | 6/1991 | Yodice et al. .......................... 428/36 |
| 5,045,285 | 9/1991 | Kolesar, Jr. ............................ 422/98 |
| 5,079,944 | 1/1992 | Boenning et al. ..................... 73/23.4 |
| 5,089,780 | 2/1992 | Megerle .............................. 324/448 |
| 5,120,421 | 6/1992 | Glass et al. .......................... 204/406 |
| 5,137,991 | 8/1992 | Epstein et al. ......................... 525/54 |
| 5,145,645 | 9/1992 | Zakin et al. ........................... 422/98 |
| 5,150,603 | 9/1992 | Boenning et al. ................... 73/31.05 |
| 5,177,994 | 1/1993 | Moriizumi et al. ................. 73/23.34 |
| 5,217,692 | 6/1993 | Rump et al. ............................ 422/98 |
| 5,239,483 | 8/1993 | Weir .................................... 364/497 |

(List continued on next page.)

FOREIGN PATENT DOCUMENTS

| | | |
|---|---|---|
| 286 307 | 10/1988 | (EP) . |
| 293 255 | 11/1988 | (EP) . |
| 298 463 | 1/1989 | (EP) . |
| 1 041 575 | 9/1966 | (GB) . |
| 2 203 249 A | 10/1988 | (GB) . |
| WO 85/01351 | 3/1985 | (WO) . |
| WO 93/06237 | 4/1993 | (WO) . |
| WO 96/07901 | 3/1996 | (WO) . |
| WO 96/30750 | 10/1996 | (WO) . |

OTHER PUBLICATIONS

Amrani, et al., "High–frequency measurements of conducting polymers: Development of a new technique for sensing volatile chemicals," *Meas. Sci. Technol.*, 6:1500–1507 (1995), no month available.

Amrani, et al., "Synthesis, chemical characterisation and multifrequency measurement of poly N–(2 pyridyl) pyrrole for sensing volatile chemicals," *Materials Science and Engineering*, C1:17–22 (1993), no month available.

Andrieux et al., "Observation of the cation radicals of pyrrole and of some substituted pyrroles in fast–scan cyclic voltammetry. Standard potentials and lifetimes," *J. Am. Chem. Soc.*, 112:2439–2440 (1990), no month available.

Barlett, P.N. et al., "Electrochemical deposition of conducting polymers onto electronic substrates for sensor applications," *Sensors and Actuators*, A21–A23:911–914 (1990), no month available.

(List continued on next page.)

*Primary Examiner*—Bruce F. Bell
(74) *Attorney, Agent, or Firm*—Townsend & Townsend & Crew LLP

(57) ABSTRACT

Chemical sensors for detecting analytes in fluids comprise first and second conductive elements (e.g., electrical leads) electrically coupled to and separated by a chemically sensitive resistor which provides an electrical path between the conductive elements. The resistor comprises a plurality of alternating nonconductive regions (comprising a nonconductive organic polymer) and conductive regions (comprising a conductive material) transverse to the electrical path. The resistor provides a difference in resistance between the conductive elements when contacted with a fluid comprising a chemical analyte at a first concentration, than when contacted with a fluid comprising the chemical analyte at a second different concentration. Arrays of such sensors are constructed with at least two sensors having different chemically sensitive resistors providing dissimilar such differences in resistance. Variability in chemical sensitivity from sensor to sensor is provided by qualitatively or quantitatively varying the composition of the conductive and/or nonconductive regions. An electronic nose for detecting an analyte in a fluid may be constructed by using such arrays in conjunction with an electrical measuring device electrically connected to the conductive elements of each sensor.

23 Claims, 22 Drawing Sheets

U.S. PATENT DOCUMENTS

| | | | |
|---|---|---|---|
| 5,256,574 | 10/1993 | Neuberger et al. | 436/143 |
| 5,298,783 | 3/1994 | Wu | 257/414 |
| 5,310,507 | 5/1994 | Zakin et al. | 252/500 |
| 5,372,785 | 12/1994 | Johnson et al. | 422/90 |
| 5,400,641 | 3/1995 | Slemon et al. | 73/19.01 |
| 5,417,100 | 5/1995 | Miller | 73/31.02 |
| 5,482,678 | 1/1996 | Sittler | 422/90 |
| 5,512,882 | 4/1996 | Stetter | 340/632 |
| 5,541,851 | 7/1996 | Sato et al. | 364/497 |
| 5,605,612 | 2/1997 | Park et al. | 204/429 |
| 5,623,212 | 4/1997 | Yamanaka | 324/693 |
| 5,654,497 | 8/1997 | Hoffheins et al. | 73/23.2 |
| 5,698,089 | 12/1997 | Lewis et al. | 205/787 |
| 5,788,833 * | 8/1998 | Lewis et al. | 205/787 |
| 5,807,701 | 9/1998 | Payne et al. | 435/34 |

OTHER PUBLICATIONS

Bidan et al., "Polypyrrole and poly(N–methylpyrrole) films doped with Keggin–type heteropolyanions: preparation and properties,"*J. Electroanal. Chem.*, 251:297–306 (1988), no month available.

Charlesworth, J.M., et al., "Mechanistic studies on the interactions between poly(pyrrole) and organic vapors," *J. Phys. Chem.*, 97:5418–5423 (1993), no month available.

Corcoran et al., "Integrated tin oxide sensors of low power consumption for use in gas and odour sensing," *Sensors and Actuators B*, 15–16:32–37 (1993), no month available.

DeVries, et al., "Synaptic circuitry of the retina and olfactory bulb," *Cell/Neuron*, 72/10 (Suppl):139–149 (1993), no month available.

Diaz, et al., "Electrooxidation of aromatic oligomers and conducting polymers," *J. Electr. Chem.*, 121:355–361 (1981), no month available.

Gardner, et al., "Integrated array sensor for detecting organic solvents," *Sensors and Actuators B*, 26–27 (1995), no month available.

Gardner, J.W., et al., "A brief history of electronic noses," *Sensors and Actuators B*, 18–19:221–220 (1994), no month available.

Gardner, J.W., et al., "A multisensor system for beer flavour monitoring using an array of conducting polymers and predictive classifiers," *Sensors and Actuators B*, 18–19:240–243 (1994), no month available.

Gardner, J.W., et al., "Application of an electronic nose to the discrimination of coffees," *Sensors and Actuators B*, 6:71–75 (1992), no month avaiable.

Gardner, J.W., et al., "Design of conducting polymer gas sensors: Modeling and experiment," *Synthetic Metals*, 55–57:3665–3670 (1983), no month available.

Gardner, J.W., et al., "Detection of vapours and odours from a multisensor array using pattern recognition. Part 1. Principal component and cluster analysis," *Sensors and Actuators B*, 4:109–115 (1991), no month available.

Gardner, J.W., et al., "Detection of vapours and odours from a multisensor array using pattern–recognition techniques. Part 2. Artificial neural networks," *Sensors and Actuators B*, 9:9–15 (1992), no month available.

Gardner, J.W., et al., "Integrated tin oxide odour sensor," *Sensors and Actuators B*, 4:117–121 (1991), no month available.

Grate, J.W., et al., "Smart sensor system for trace organophosphorus and organosulfur vapor detection employing a temperature–controlled array of surface acoustic wave sensors, automated sample preconcentration, and pattern recognition," *Anal. Chem.*, 65:1868–1881 (1993), no month available.

Grate, J.W., et al., "Solubility interactions and the design of chemically selective sorbent coatings for chemical sensors and arrays," *Sensors and Actuators B*, 3:85–111 (1991), no month available.

Kanazawa, et al., "Electrical properties of pyrrole and its copolymers," *Synthetic Metals*, 4:119–130 (1981), no month available.

Kauer, "Contributions of topography and parallel processing to odor coding in the vertebrate olfactory pathway," *TINS*, 14(2):79–85(1991), no month available.

Kaufman, et al., "Evolution of polaron states into bipolarons in polypyrrole," *Physical Review Letters*, 53(19):1005–1008 (1984), no month available.

Lancet, et al., "Olfactory receptors," *Current Biology*, 3(10):668–674 (1993), no month available.

Lundberg et al., "Resistivity of a composite conducting polymer as a function of temperature, pressure and enviroment: Applications as a pressure and gas concentrator," *J. Appl. Phys.*, 60(3), Aug. 1986.

Lundström, I., et al., "Artificial 'olfactory' images from a chemical sensor using a light–pulse technique," *Nature*, 352:47–50 (1991), no month available.

Morris, et al., "The system ethanol–methanol at 40oC, "*Canadian J. Res.*, 20(B):207–211 (1942), no. month available.

Musio, et al., "High–frequency a.c. investigation of conducting polymer gas sensors," *Sensors and Actuators B*, 223–226 (1995), no month available.

Pearce, T.C., et al., "Electronic nose for monitoring the flavour of beers," *Analyst*, 118:371–377 (1993), no month available.

Reed, "Signaling pathways on odorant detection," *Neuron*, 8:205–209 (1992), no month available.

Salmon, et al., "A chemical route to pyrrole polymer films," *J. Polymer Sci.*, 20(3):187–193 (1982), no month available.

Setter, et al., "Sensor array and catalytic filament for chemical analysis of vapors and mixtures," *Sensors and Actuators*, B1:43–47 (1990), no month available.

Shurmer, et al., "An electronic nose: a sensitive and discriminating substitute for a mammalian olfactory system," *IEE Proceedings*, 137G(3):197–204 (1990), no month available.

Shurmer, H.V., et al., "Integrated arrays of gas sensors using conducting polymers with molecular sieves," *Sensors and Actuators B*, 4:29–33 (1991).

Shurmer, H.V., et al., "Odour discrimination with an electroic nose," *Sensors and Actuators B.*, 8:1–11 (1992).

Stetter, et al., "Detection of hazardous gasses and vapors: Pattern recognition analysis of data from an electrochemical sensor array," *Anal. Chem.*, 58:860–866 (1986).

Stetter, J.R., et al., "Quality classification of grain using a sensor array and pattern recognition," *Analytica Chimica Acta*, 284:1–11 (1993).

Topart, P., et al., "Characterization of the interaction between poly(pyrrole) films and methanol vapor," *J. Phys. Chem.*, 96:7824–7830 (1992).

Winquist, F., "Performance of an electronic nose for quality estimation of ground meat," IOP Publishing Ltd, pp. 1493–1500 (1993).

Yakushi et al., "Optical study of polypyrrole perchlorate," *J. Chem. Phys.*, 79(10):4774–4778 (1984).

Zaromb, S., et al. "Theoretical basis for identification and measurement of air contaminants using an array of sensors having partly overlapping selectivities," *Sensors and Actuators*, 6:225–243 (1984).

* cited by examiner

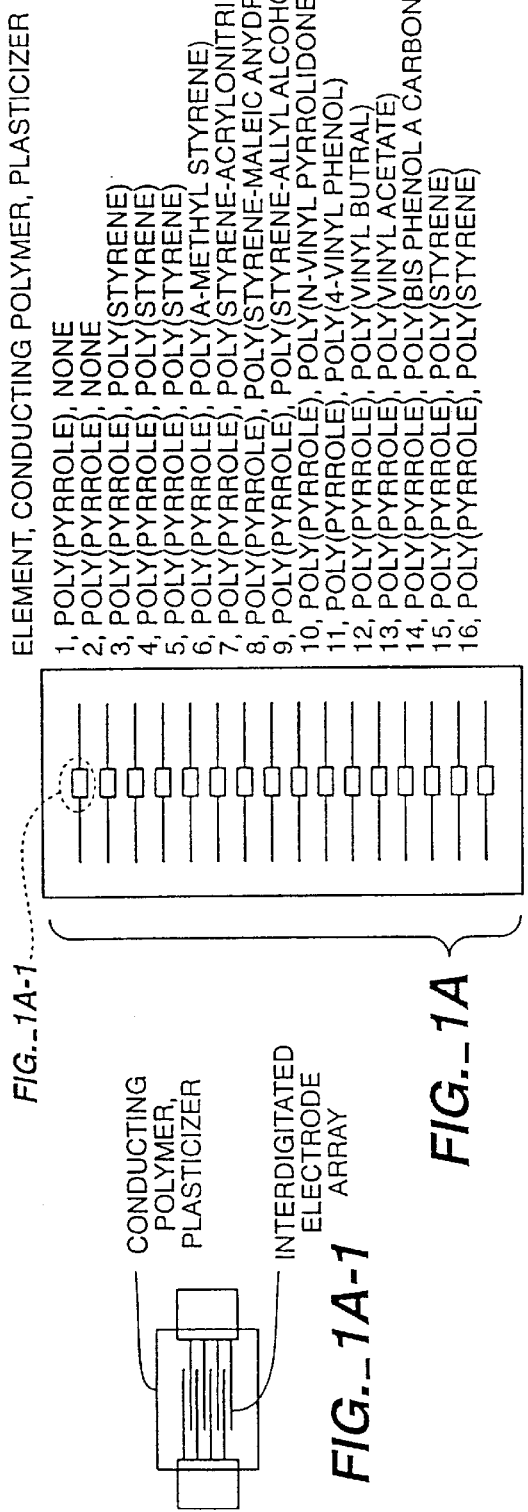
FIG._1A
FIG._1A-1
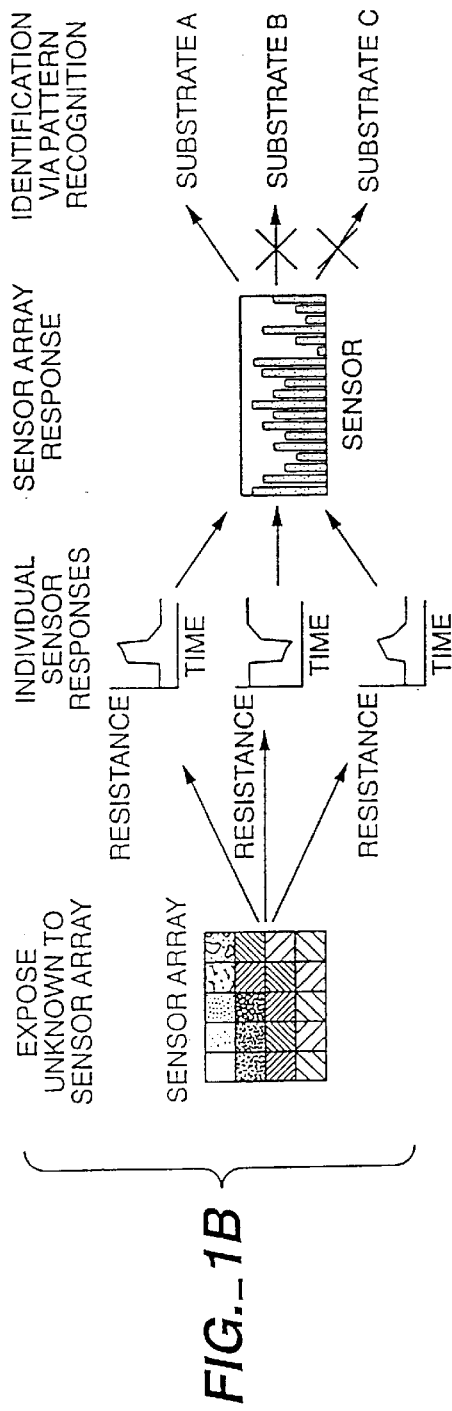
FIG._1B

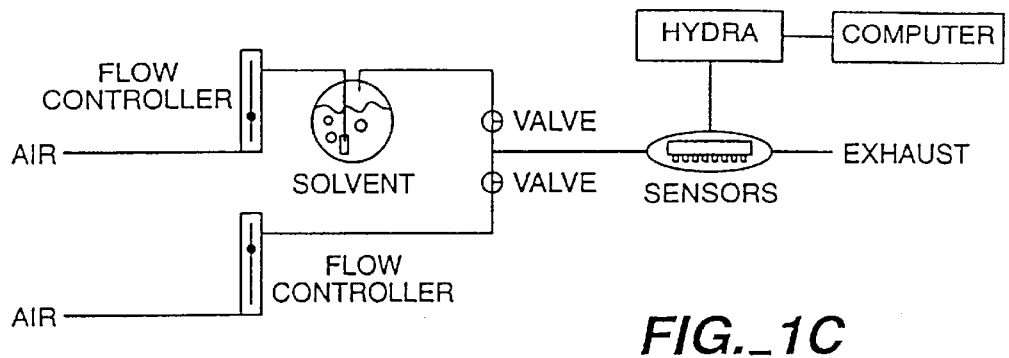
FIG._1C
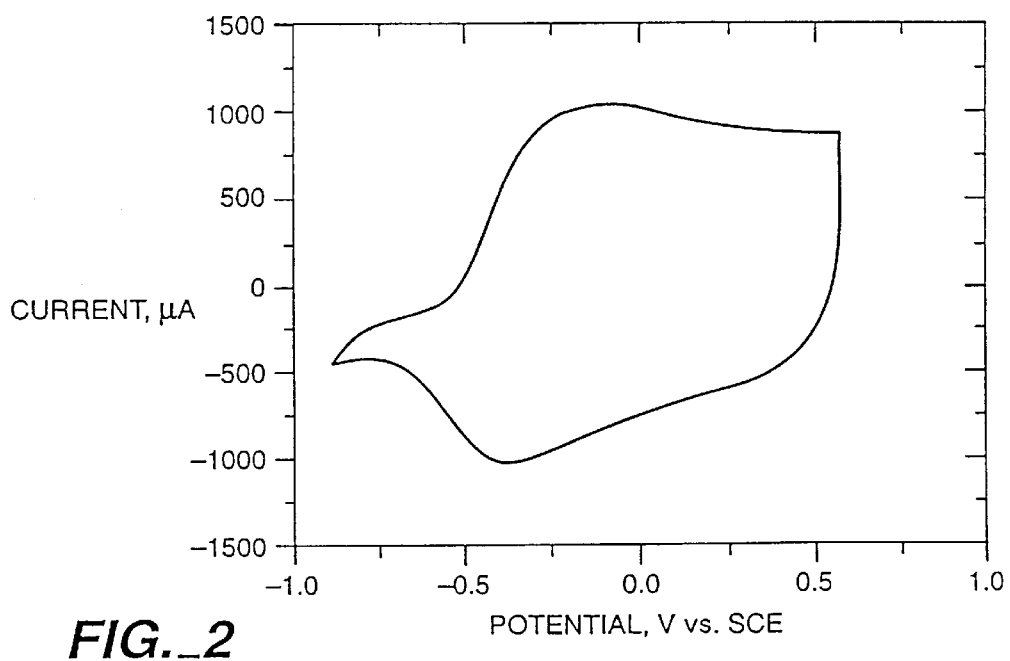
FIG._2

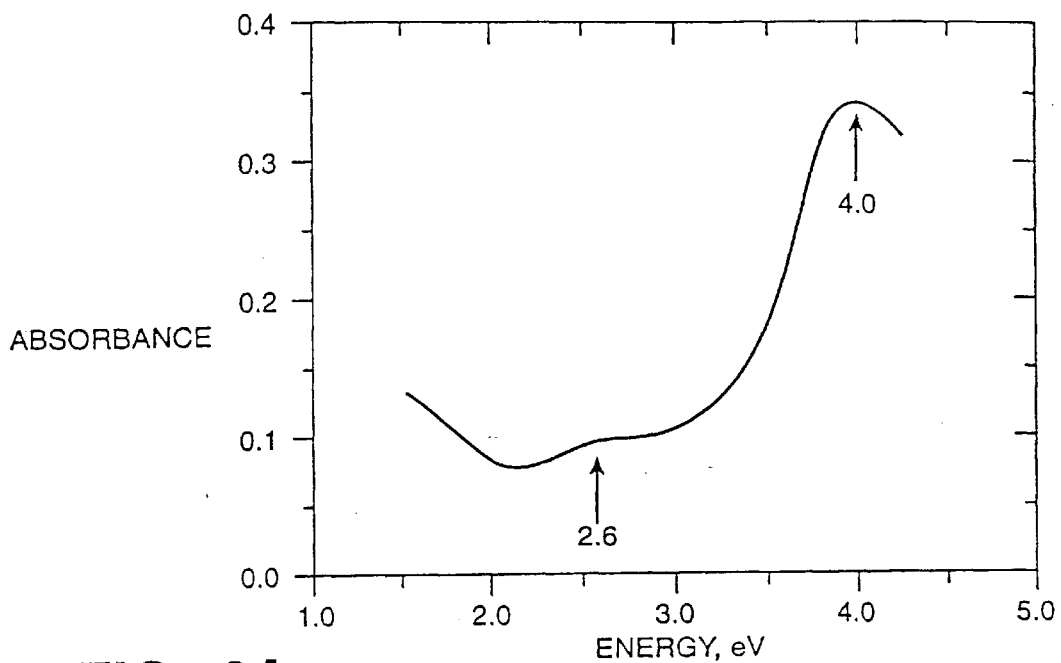
FIG._3A
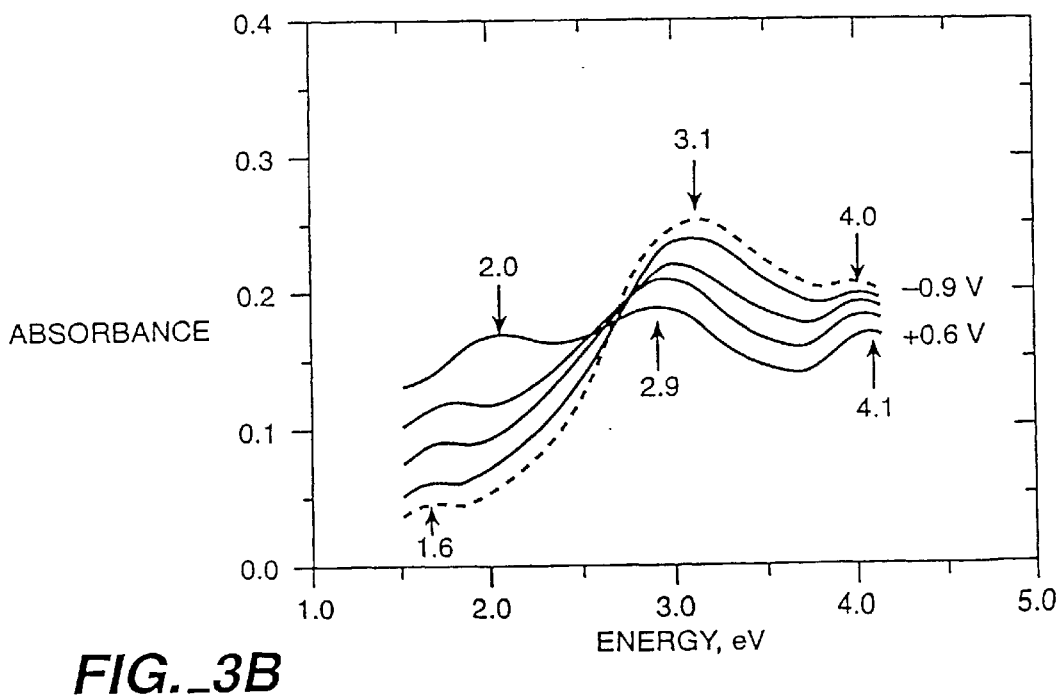
FIG._3B

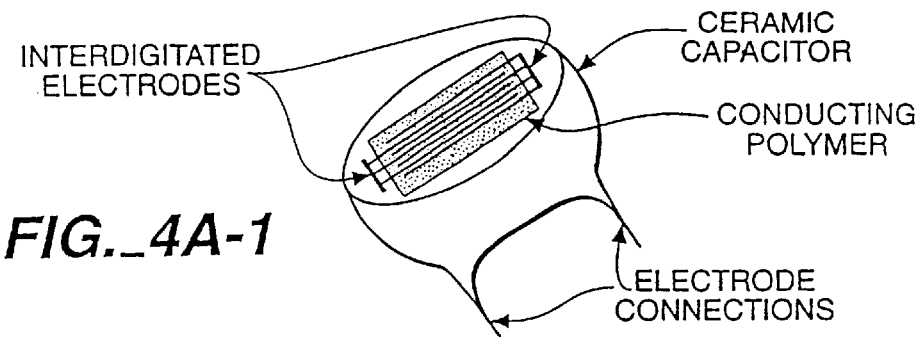
FIG._4A-1
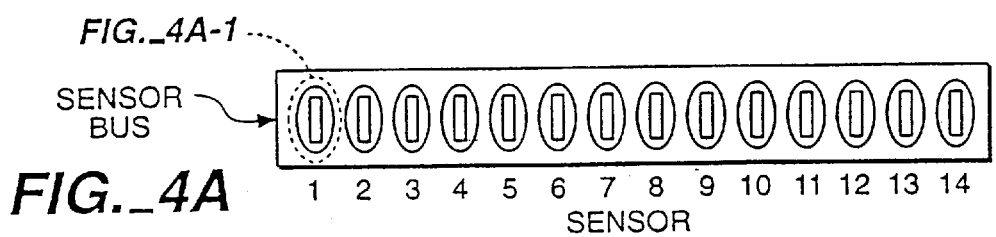
FIG._4A
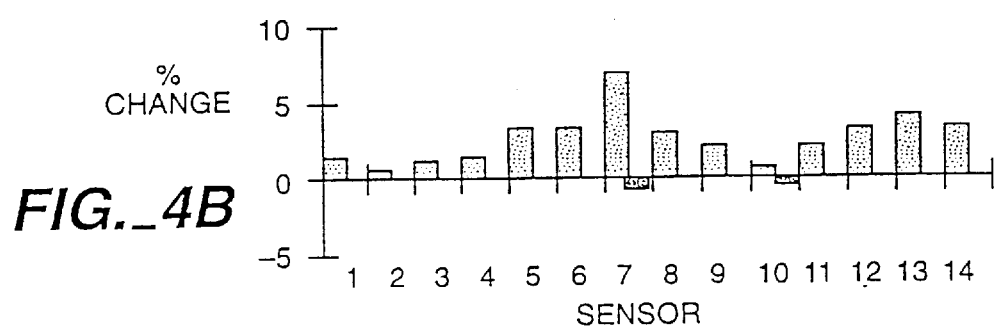
FIG._4B
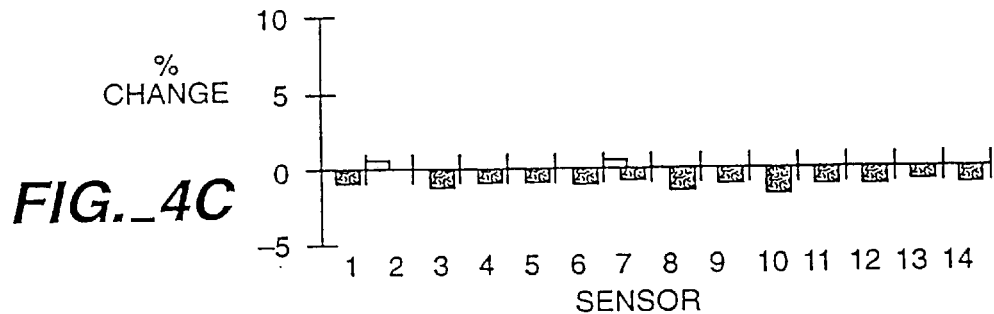
FIG._4C
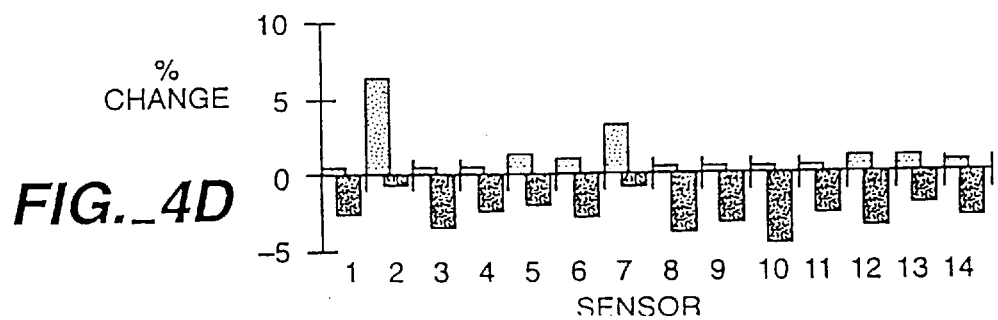
FIG._4D

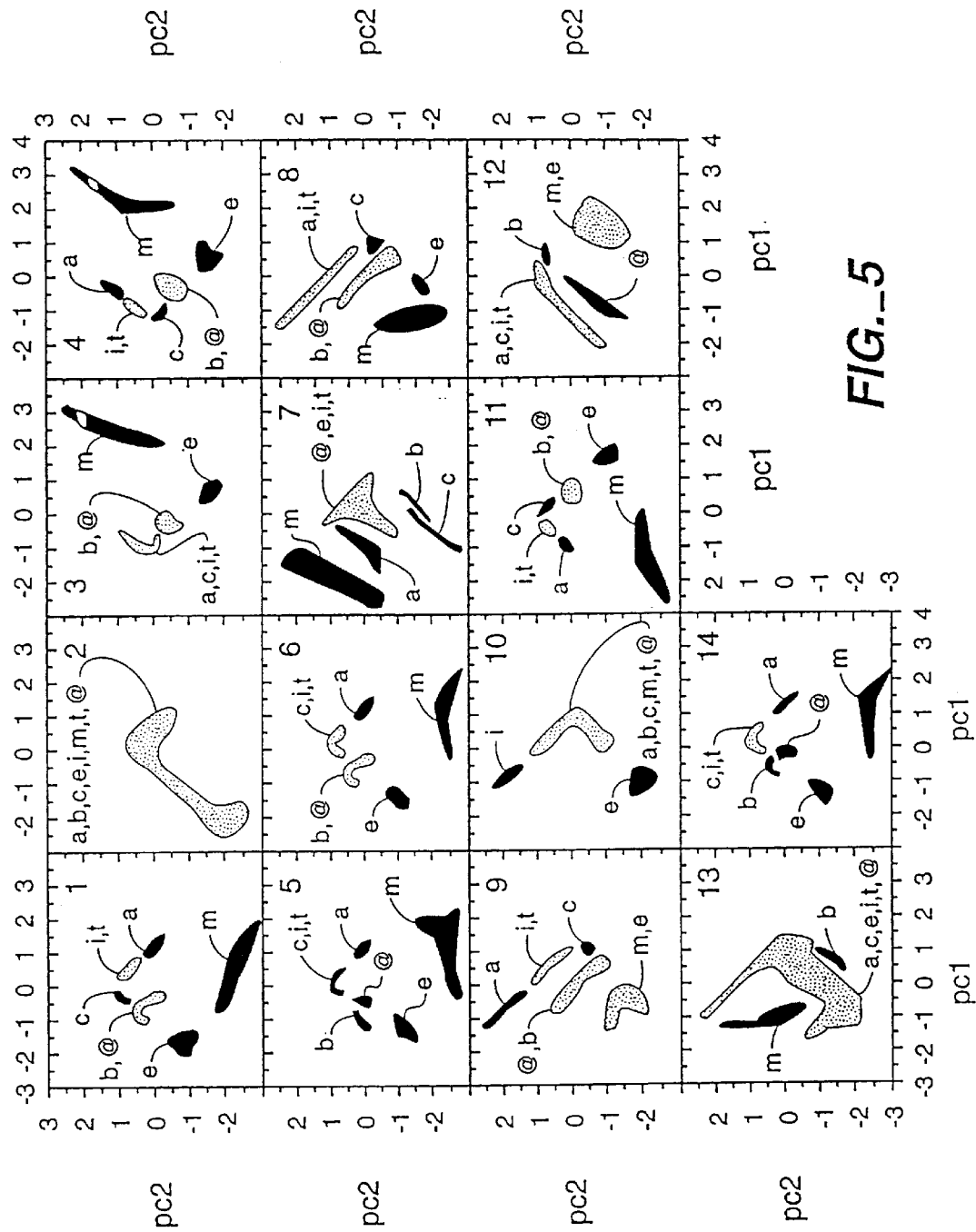
FIG._5

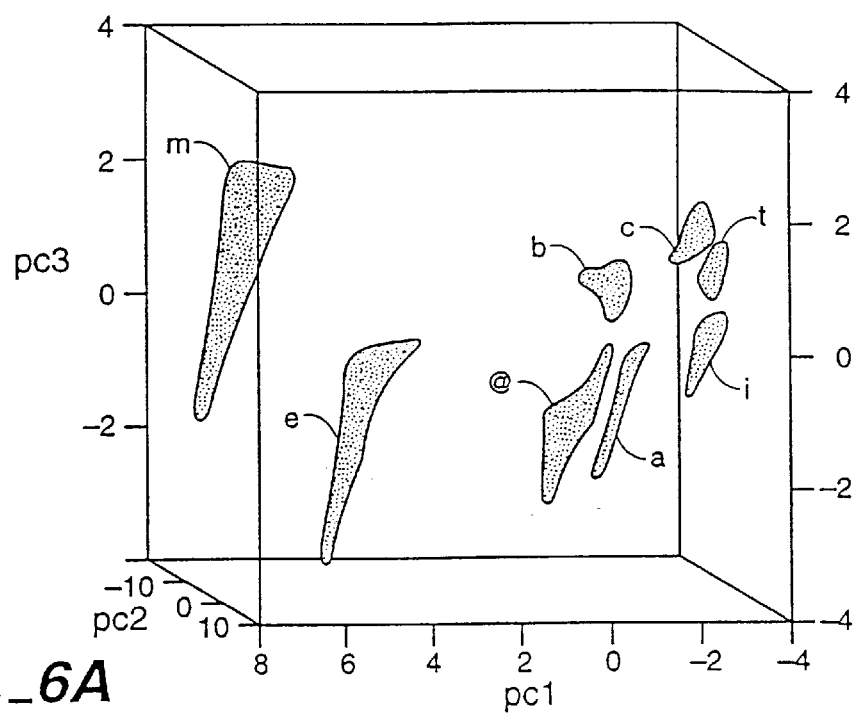
FIG._6A
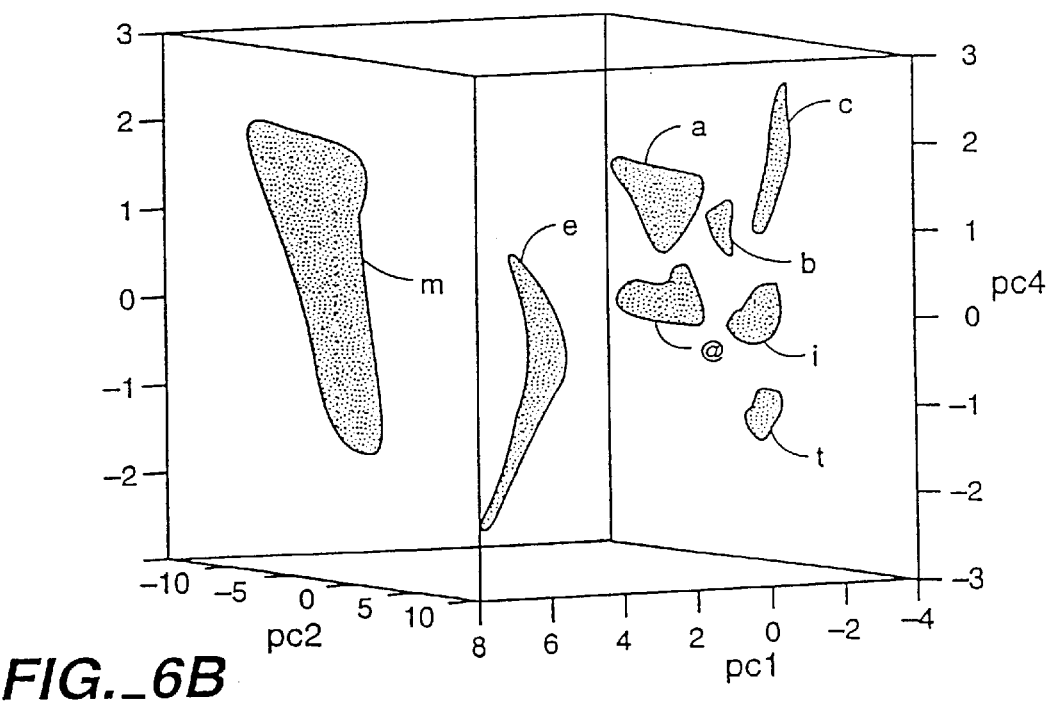
FIG._6B

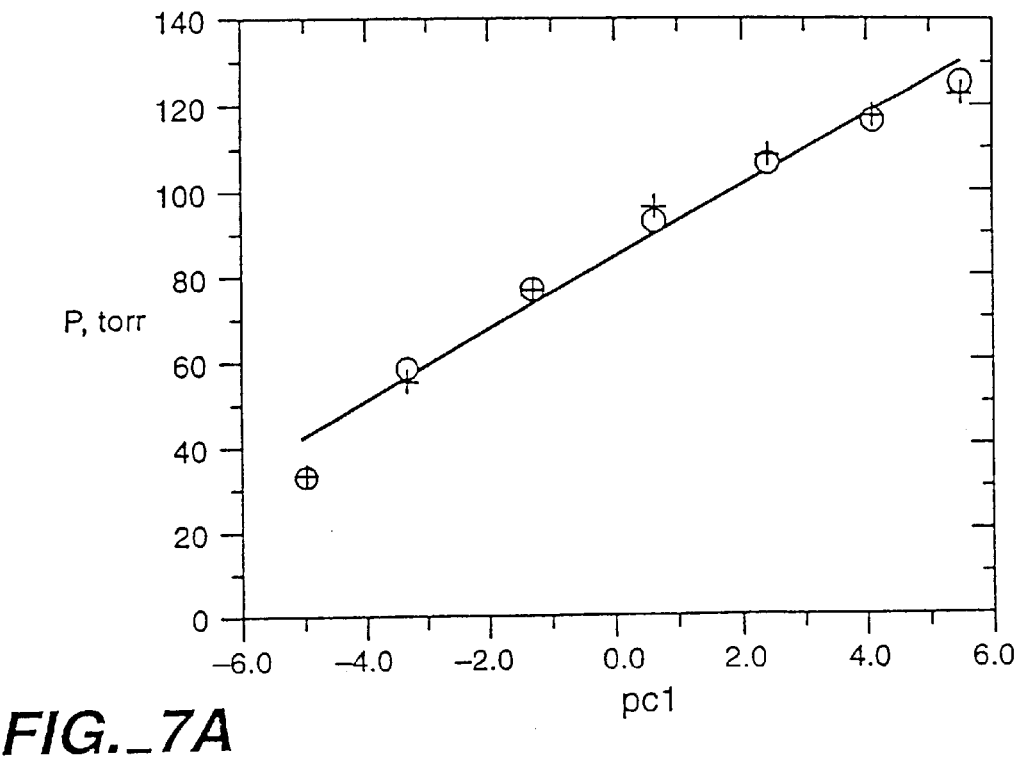
FIG._7A
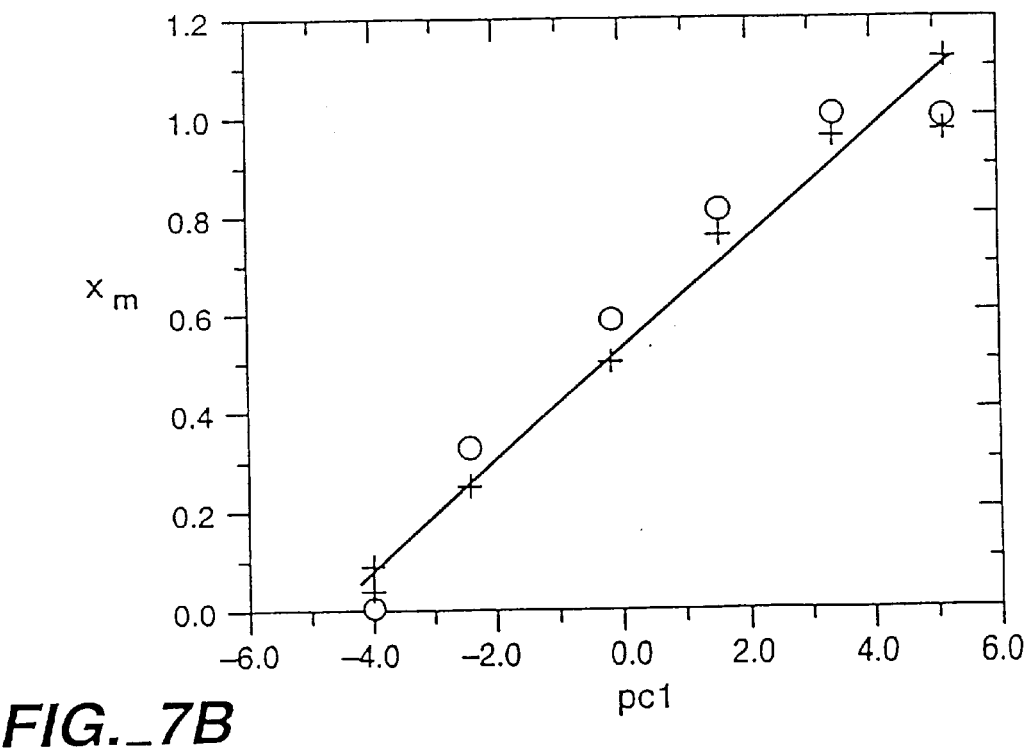
FIG._7B

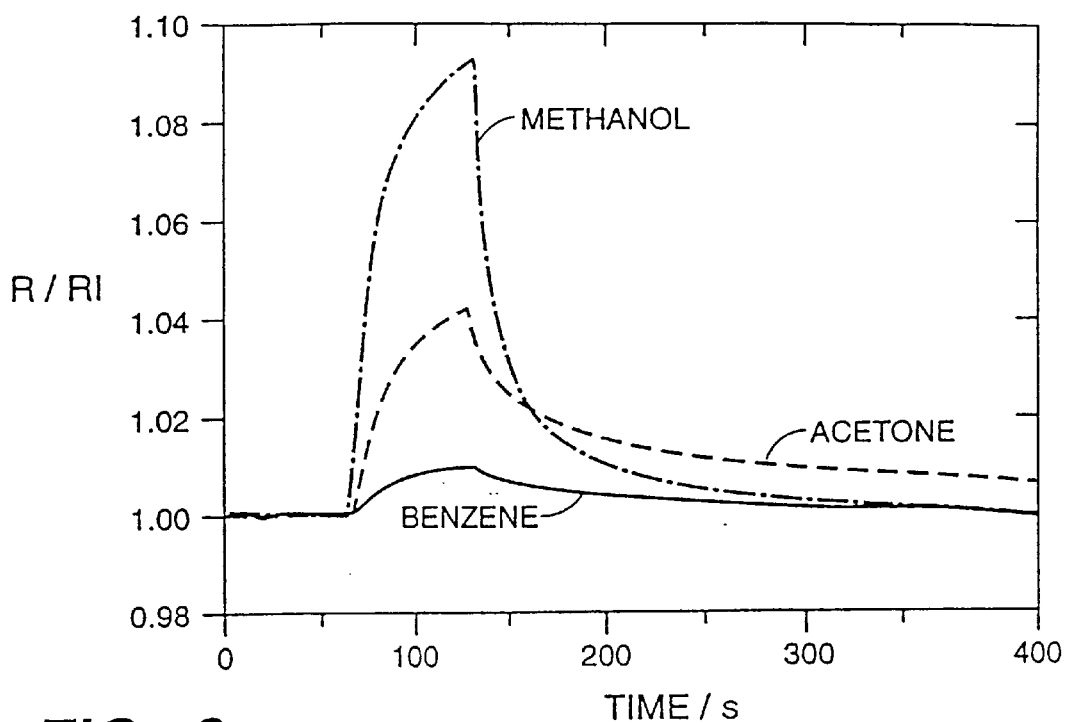
FIG._8
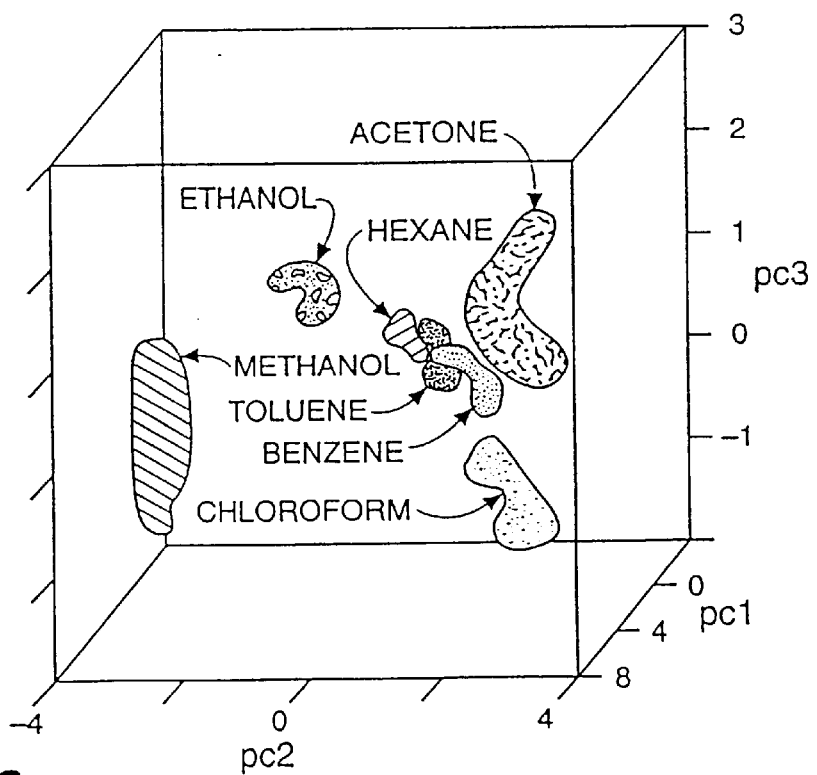
FIG._9

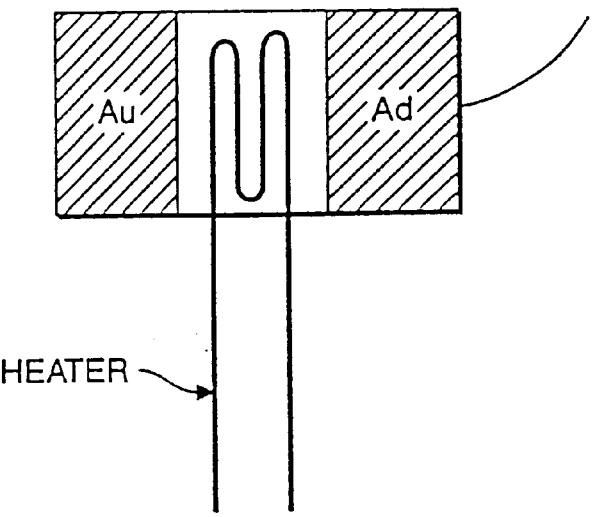
FIG._10A
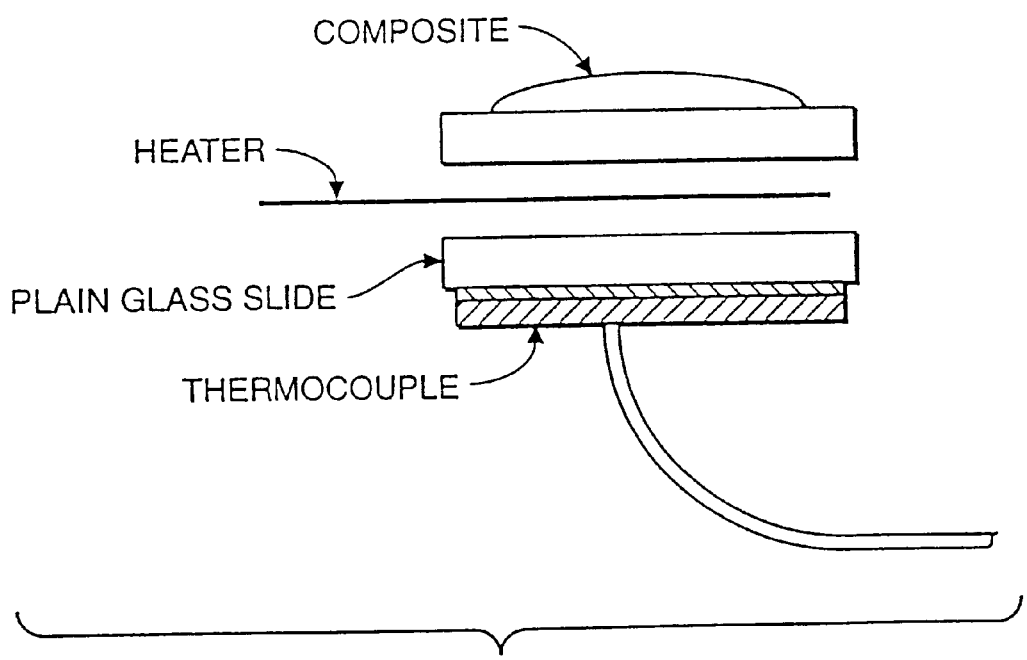
FIG._10B

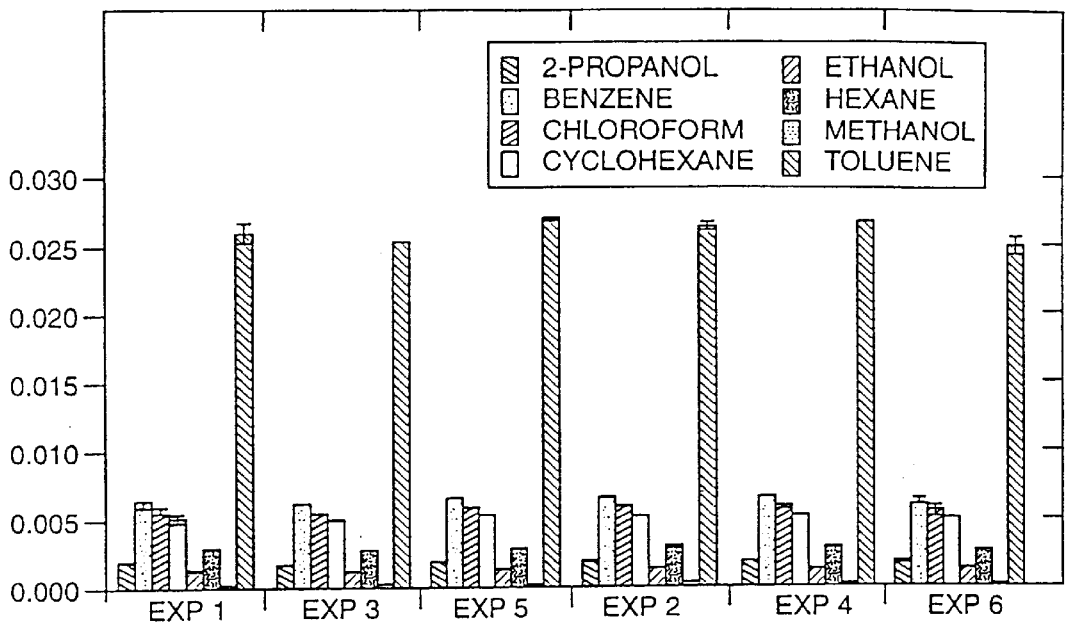
FIG._11A
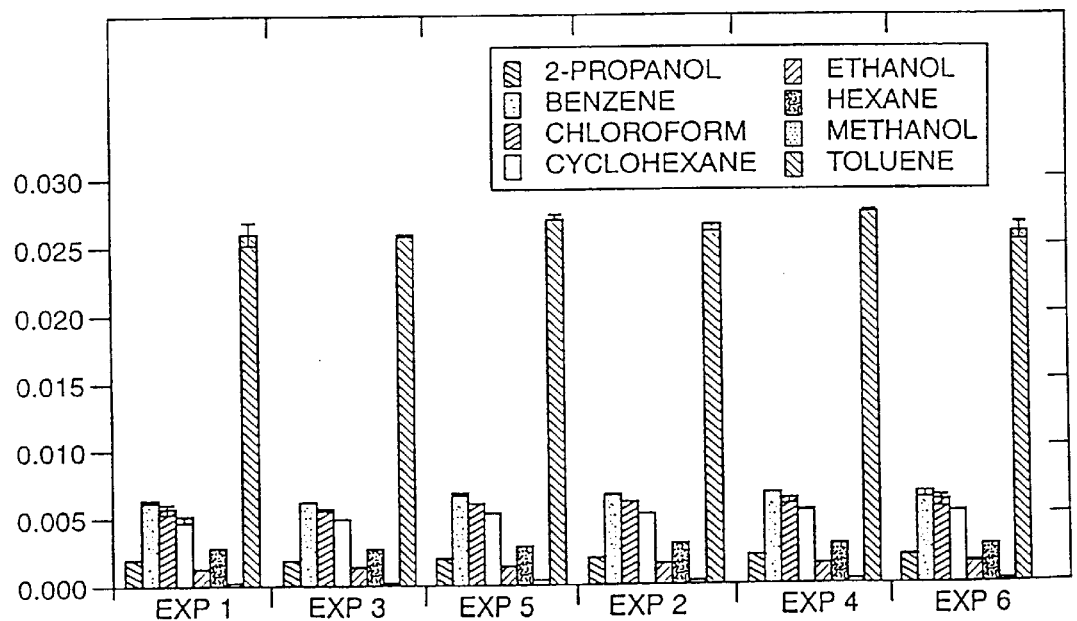
FIG._11B

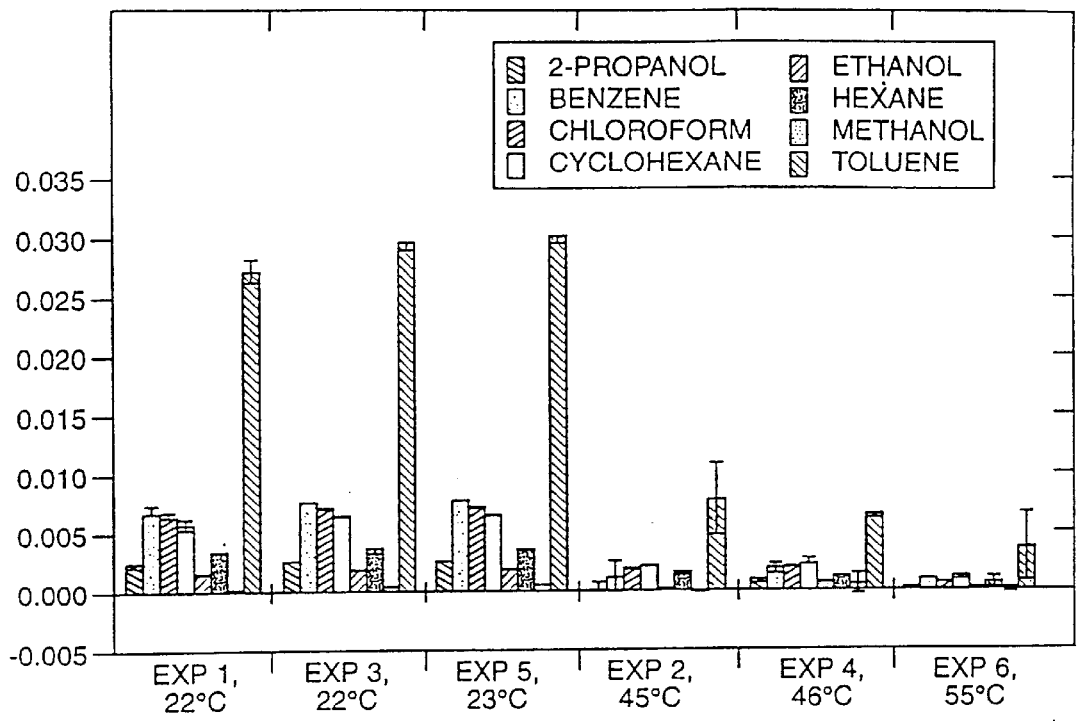
FIG._11C
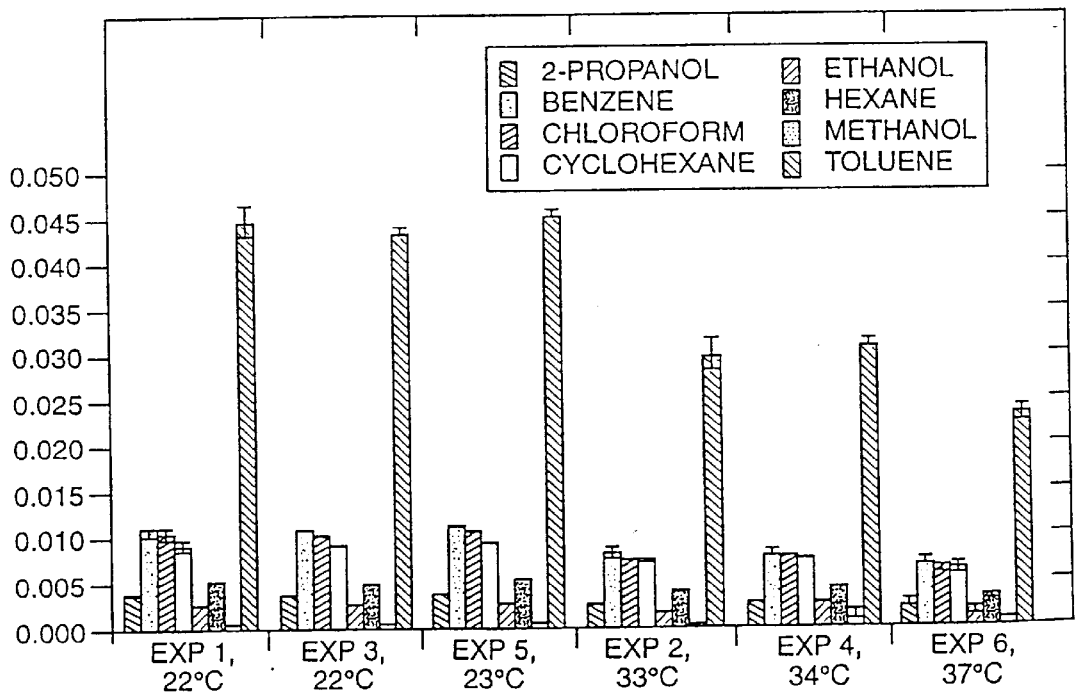
FIG._11D

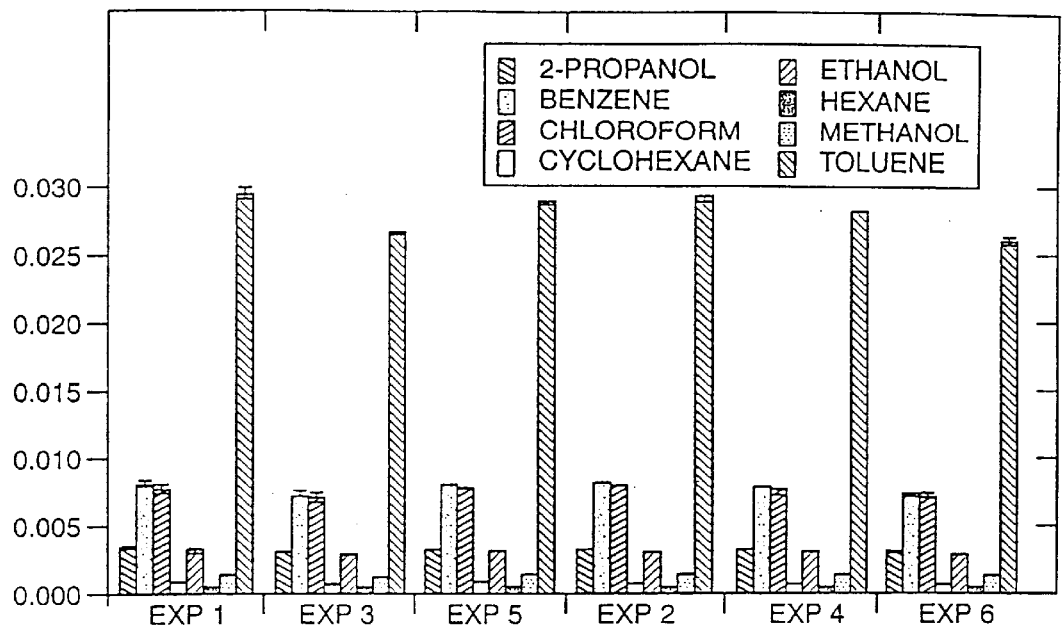
FIG._11E
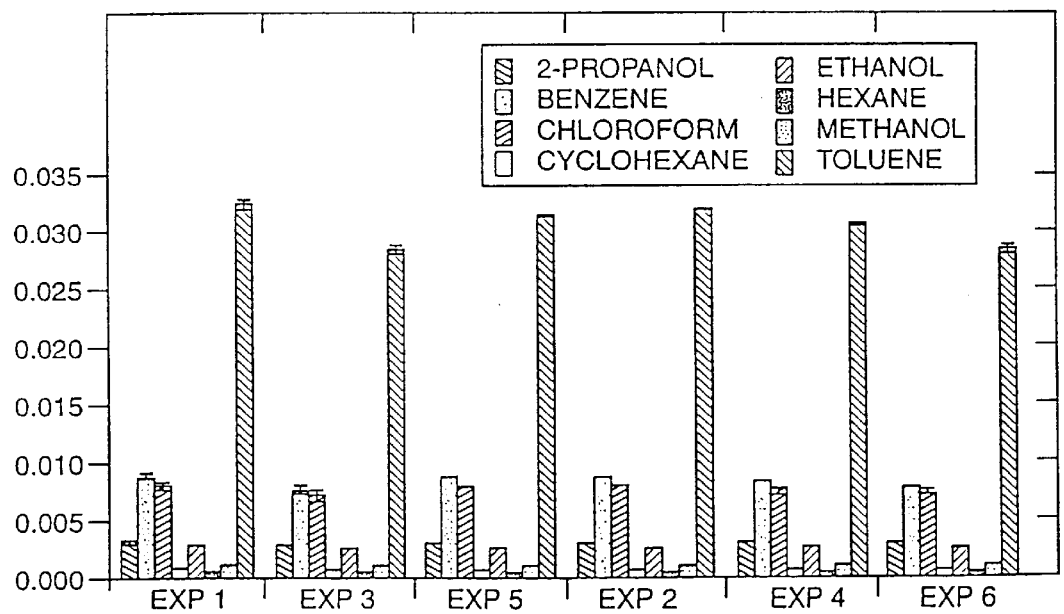
FIG._11F

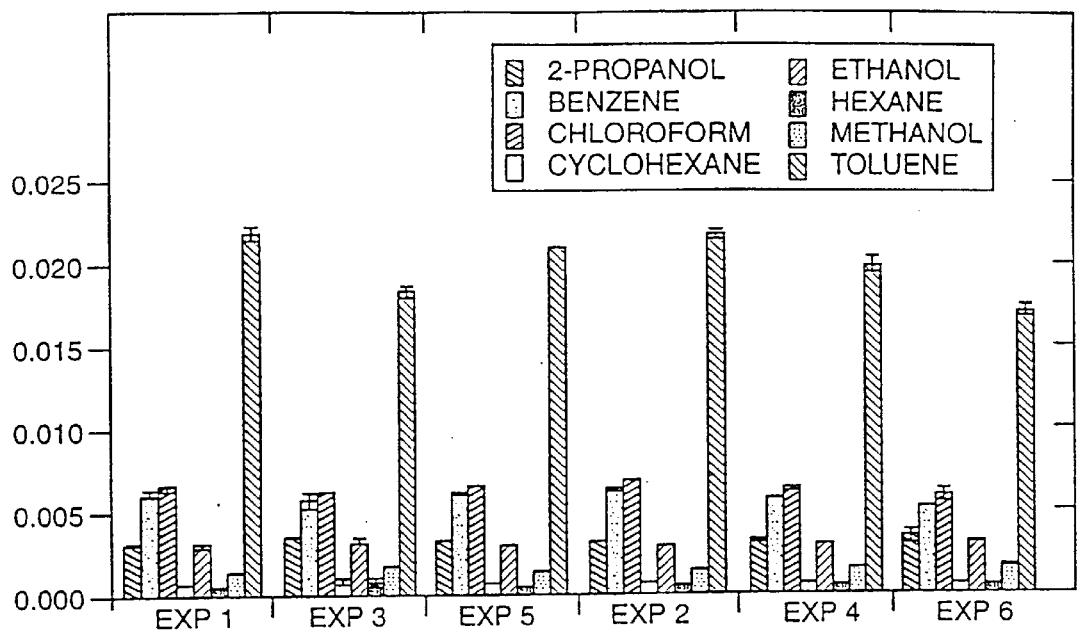
*FIG._11G*
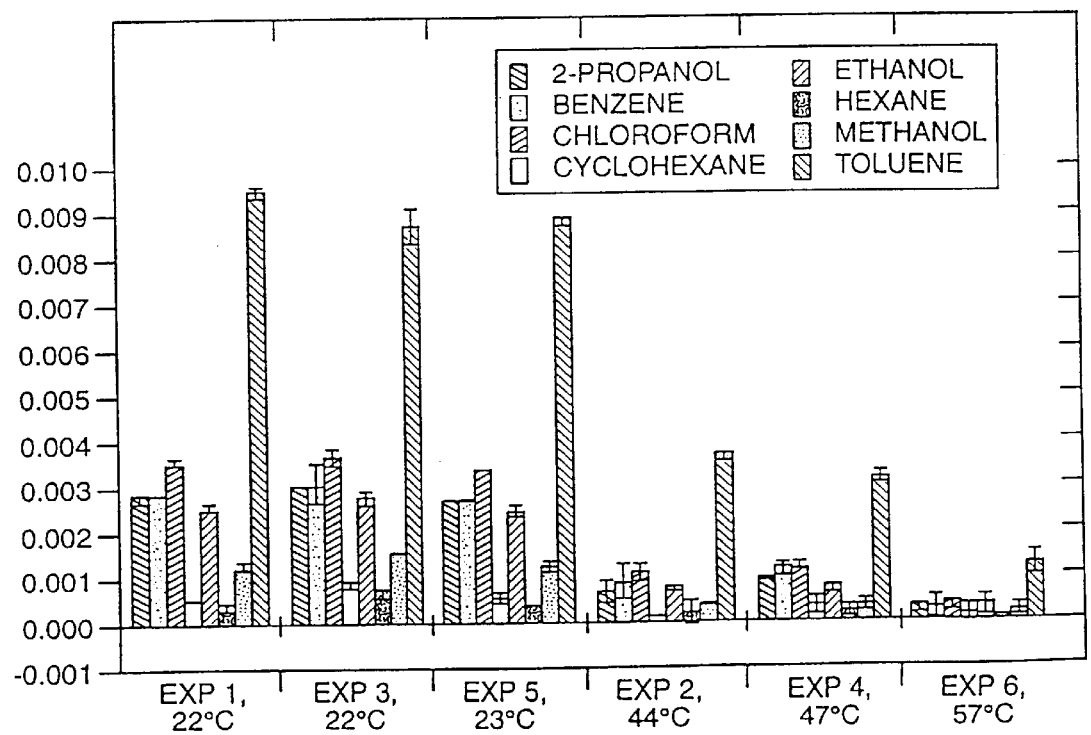
*FIG._11H*

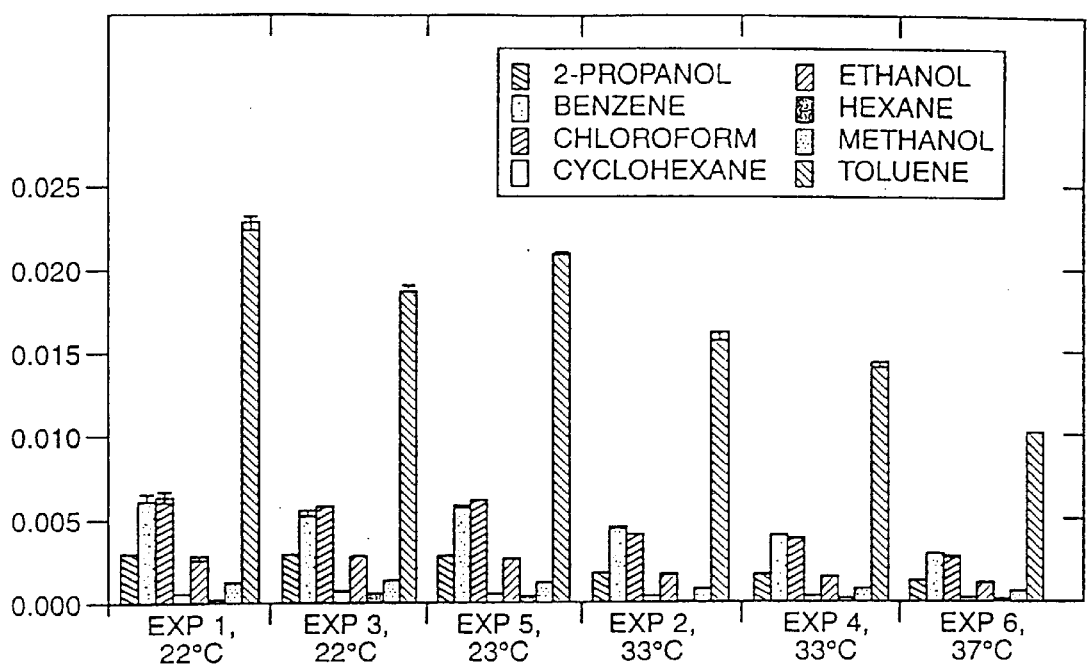
FIG._11I
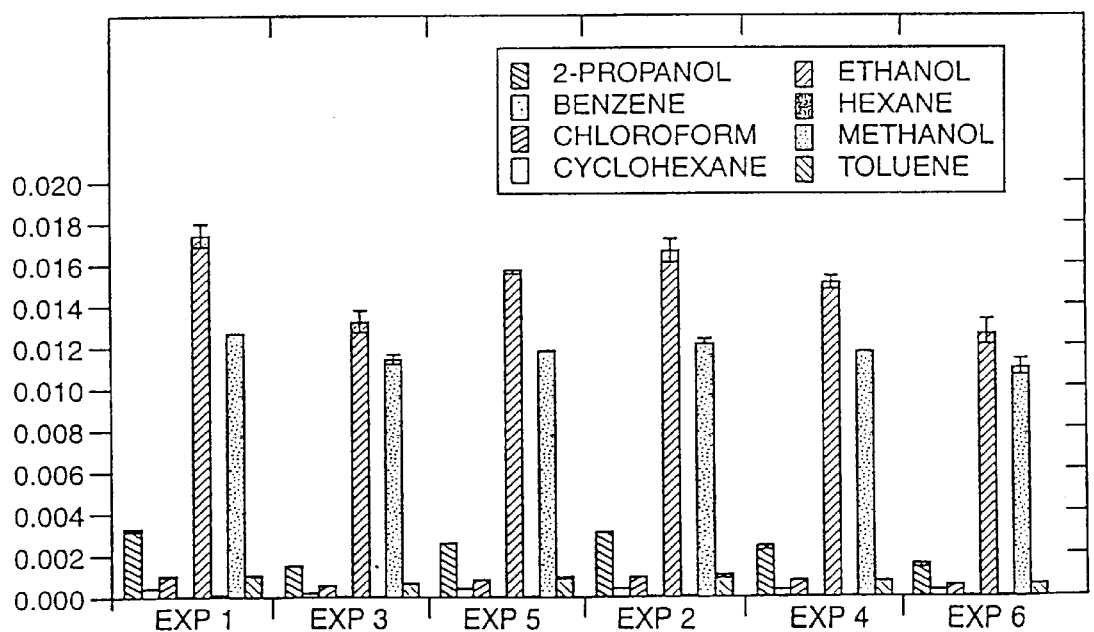
FIG._11J

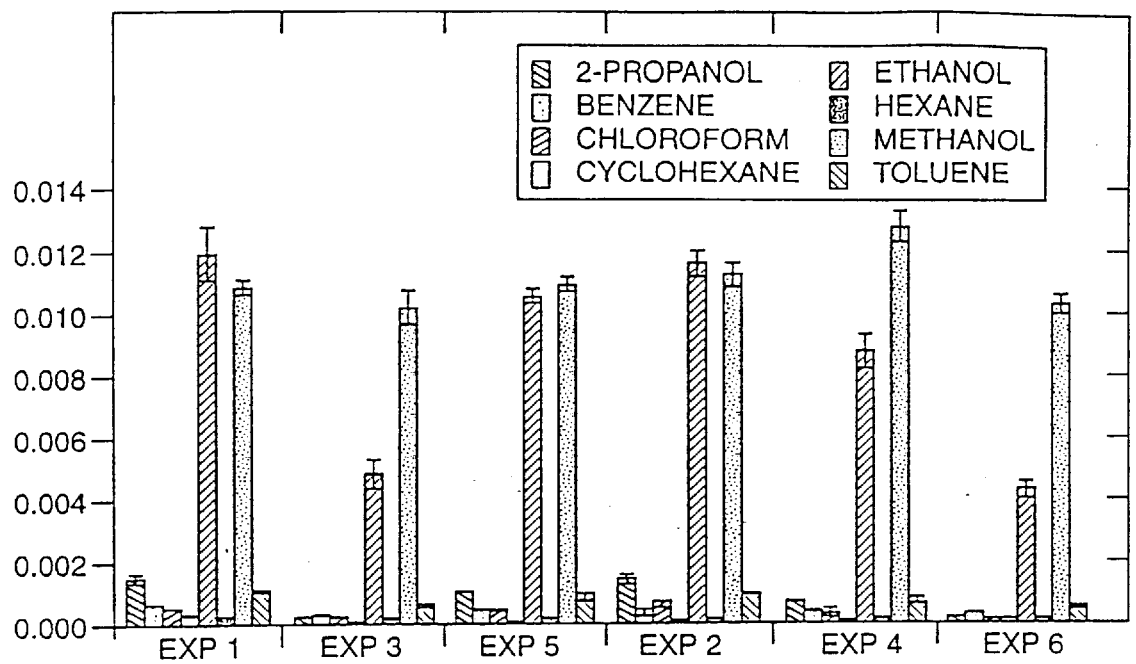
FIG._11K
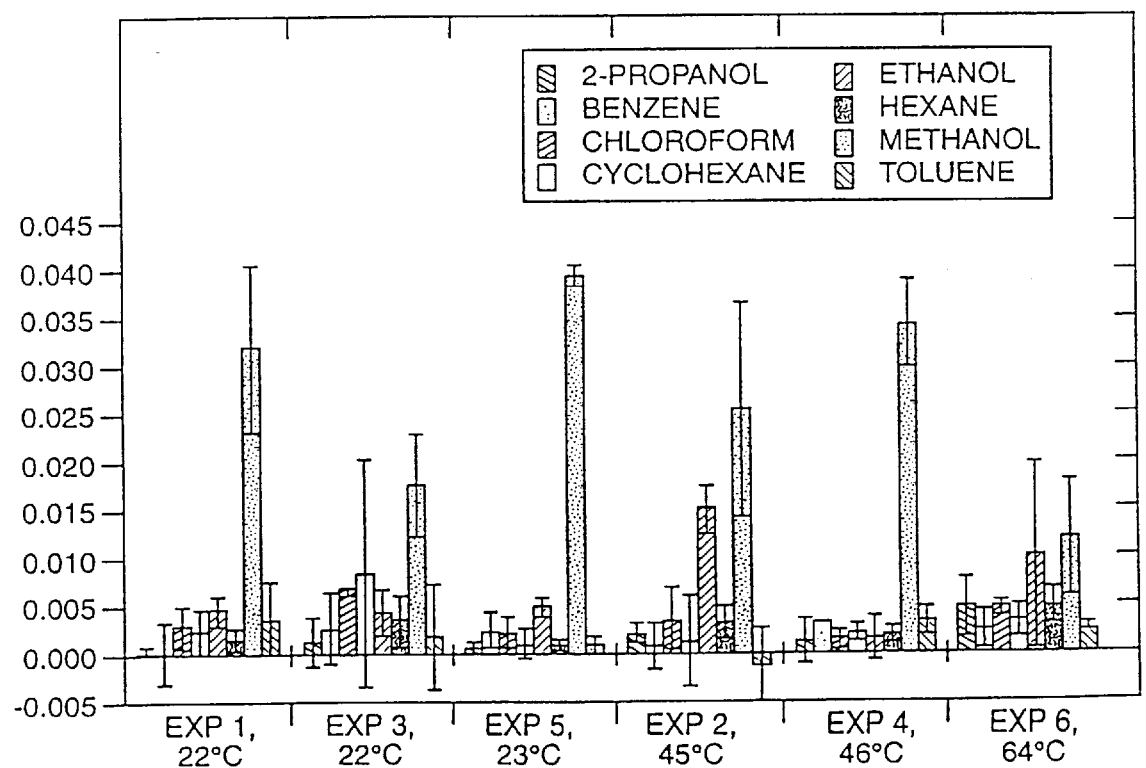
FIG._11L

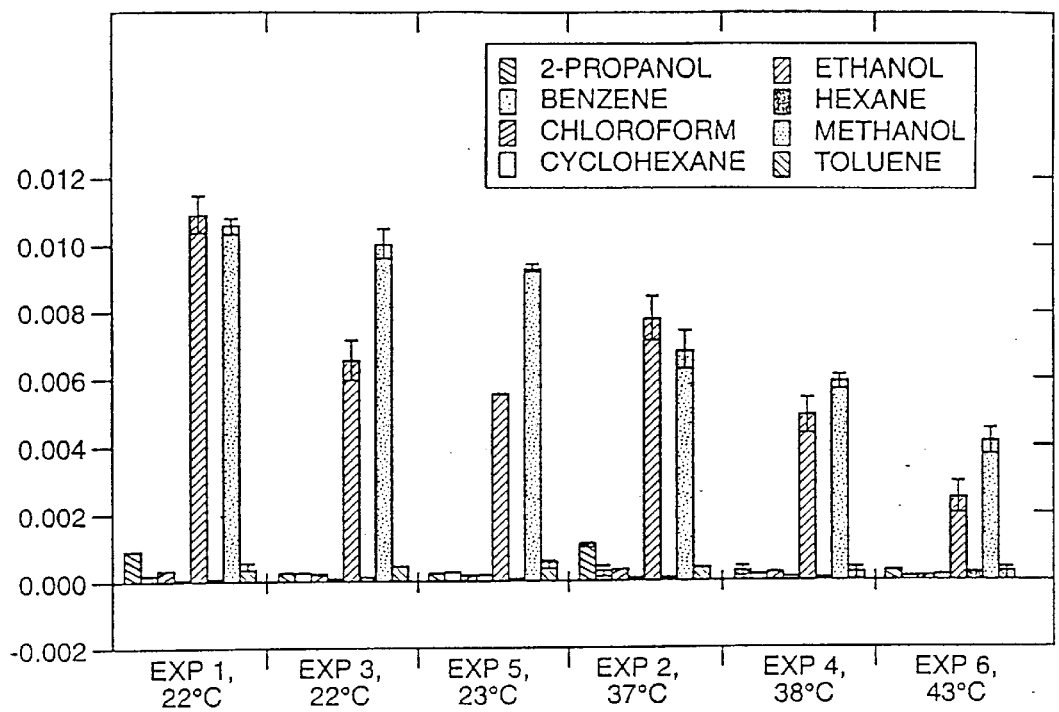
FIG._11M
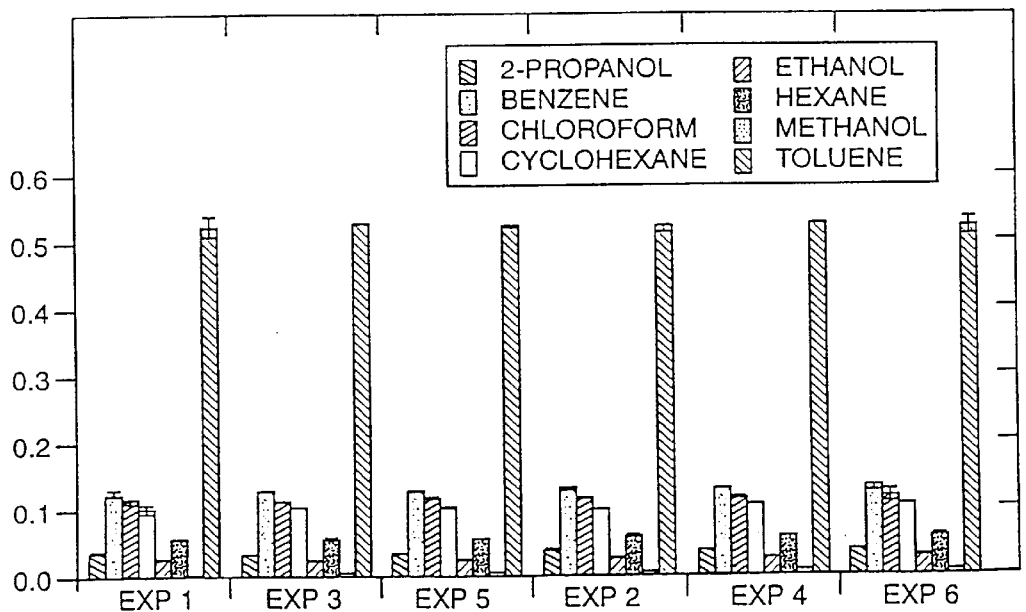
FIG._12A

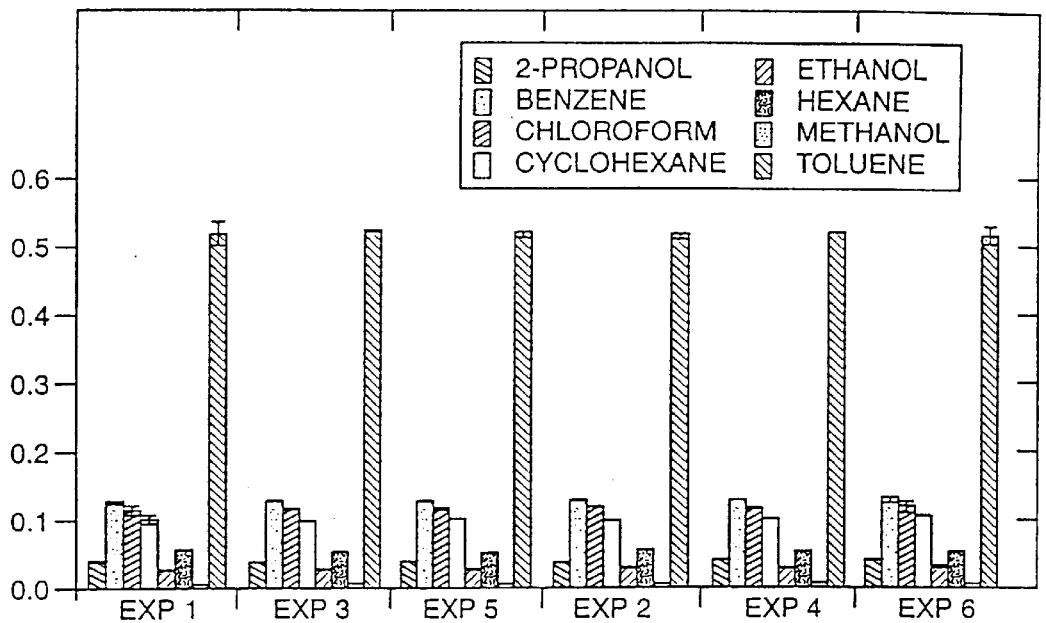
FIG._12B
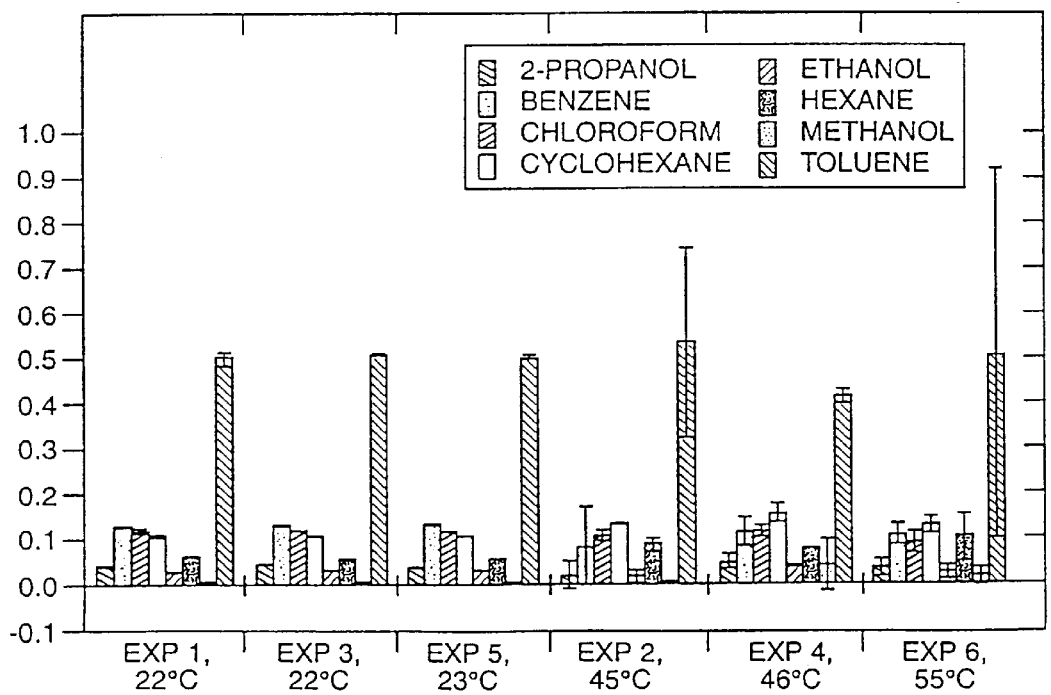
FIG._12C

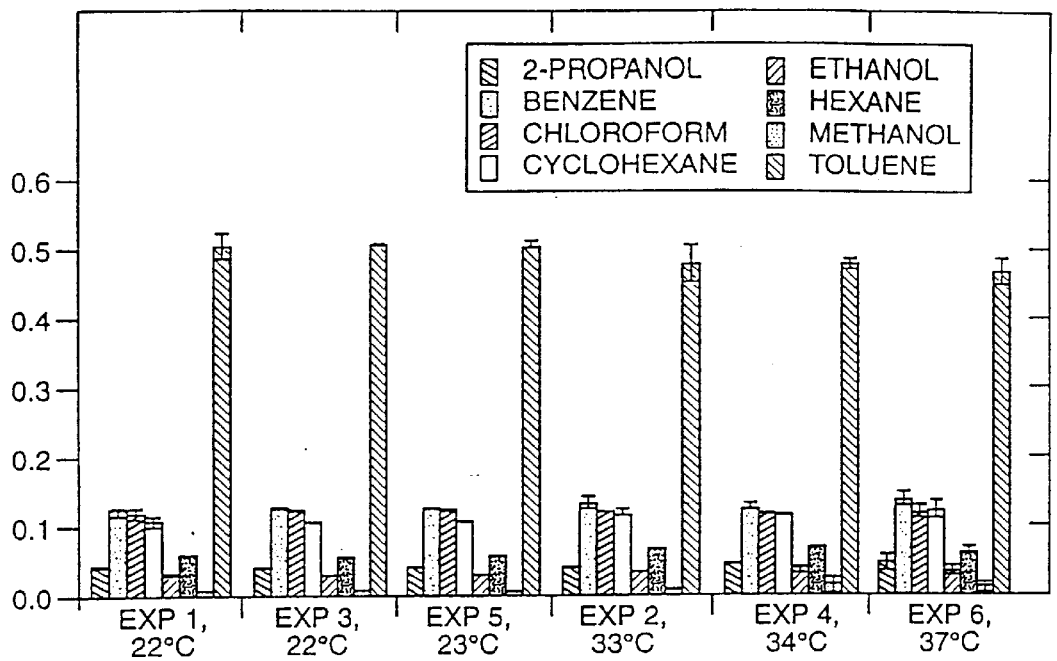
FIG._12D
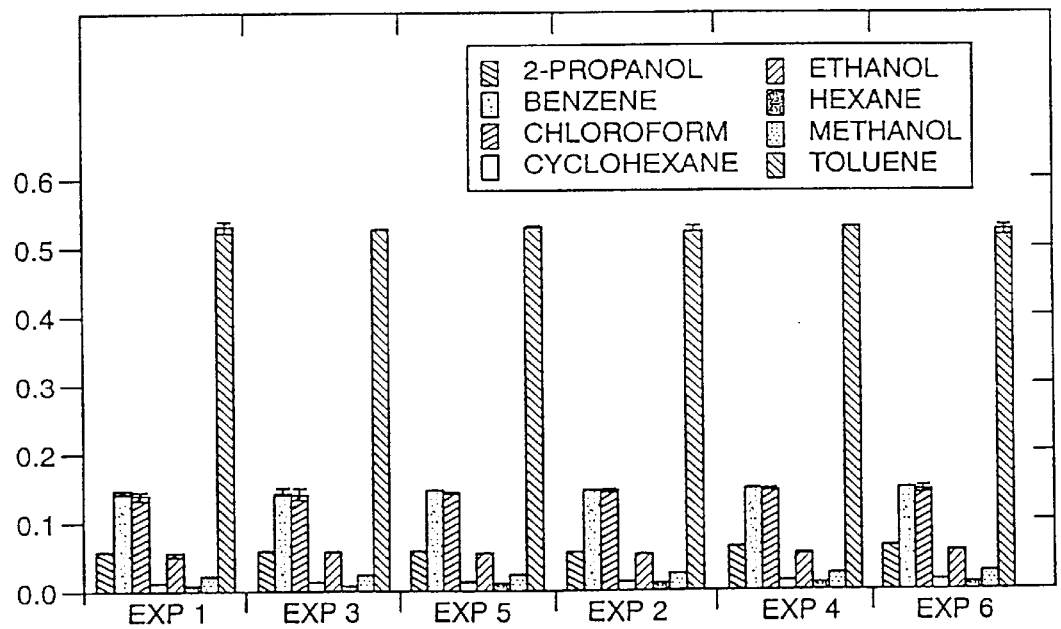
FIG._12E

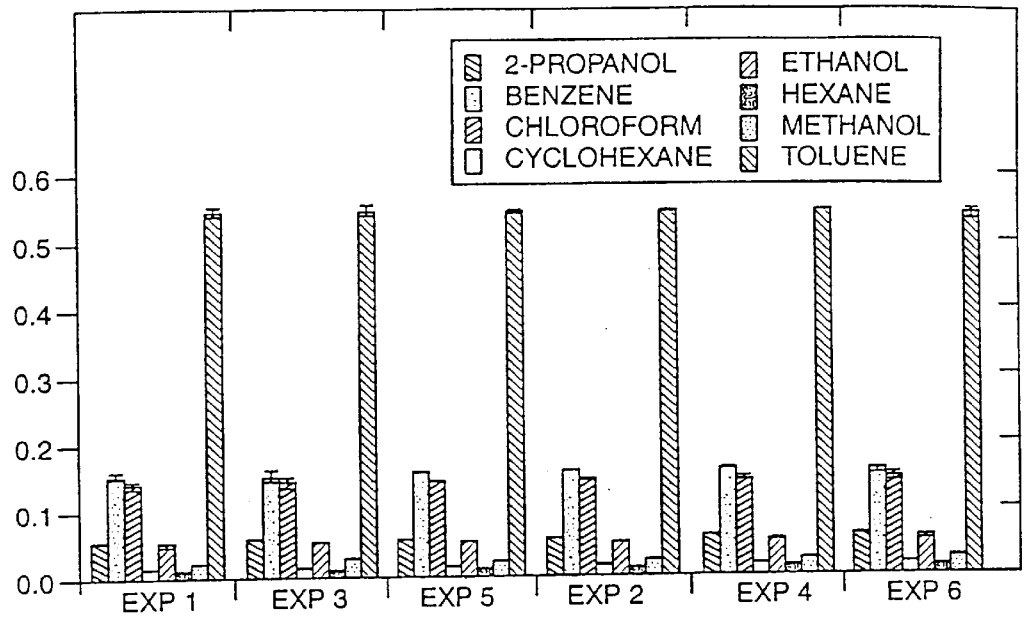
FIG._12F
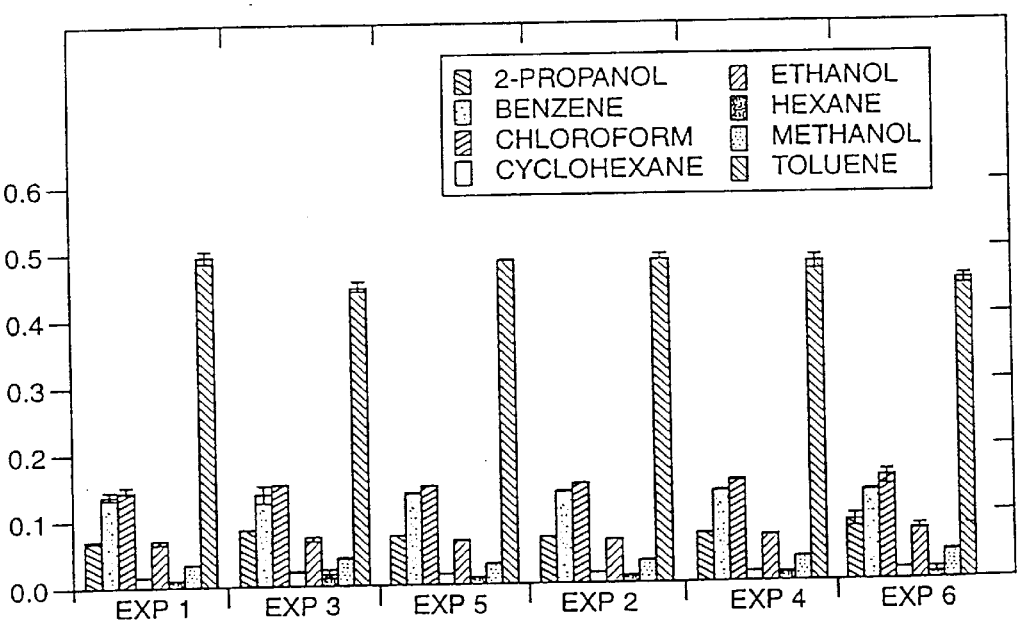
FIG._12G

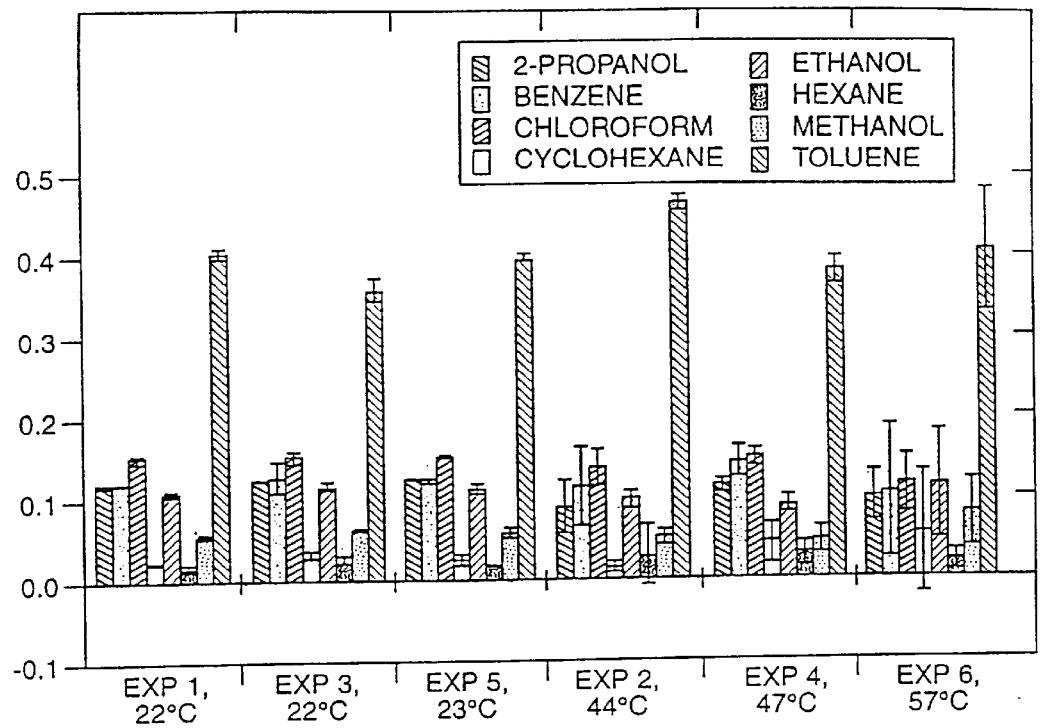
FIG._12H
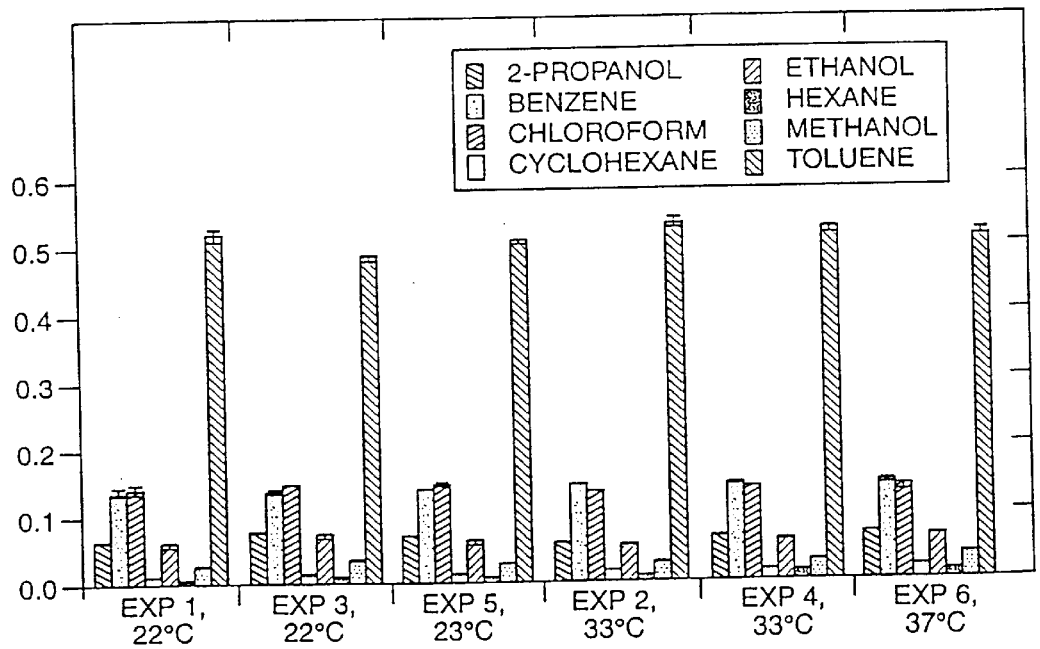
FIG._12I

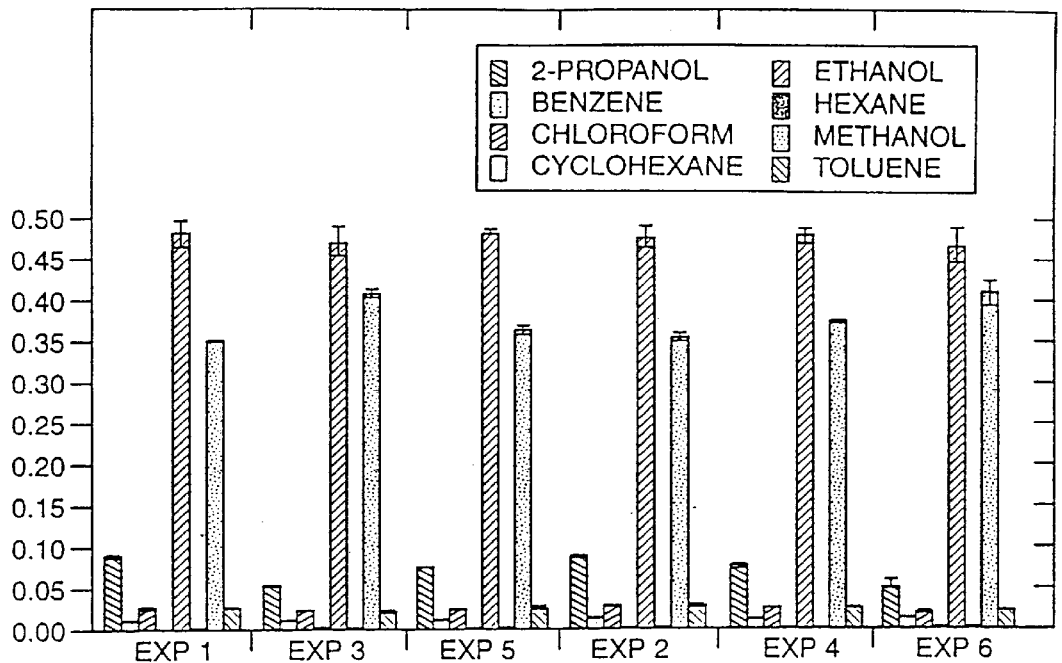
FIG._12J
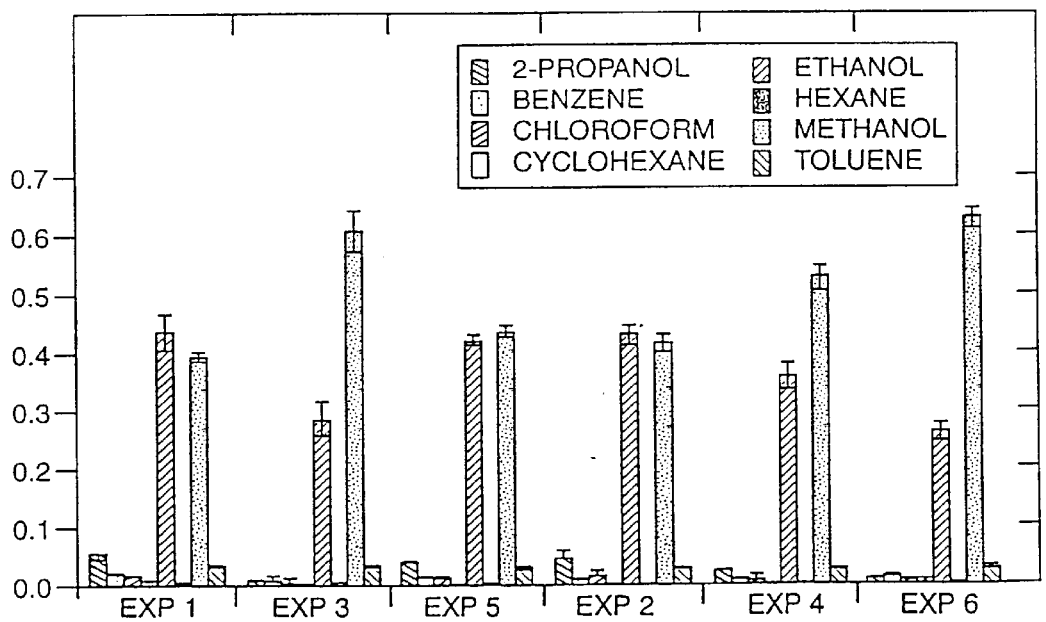
FIG._12K

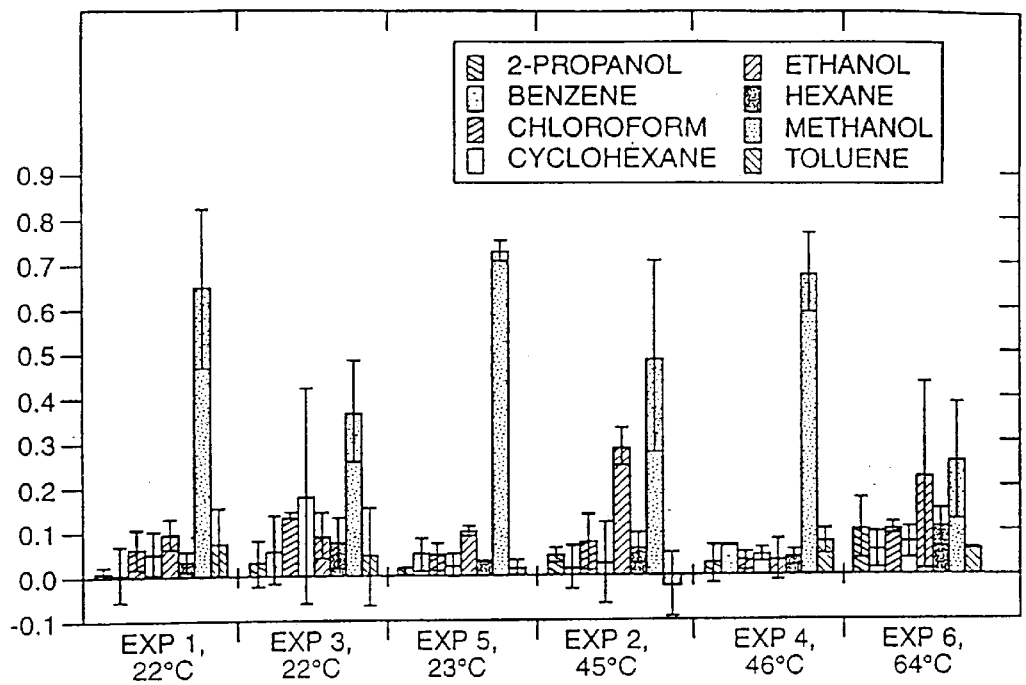
FIG._12L
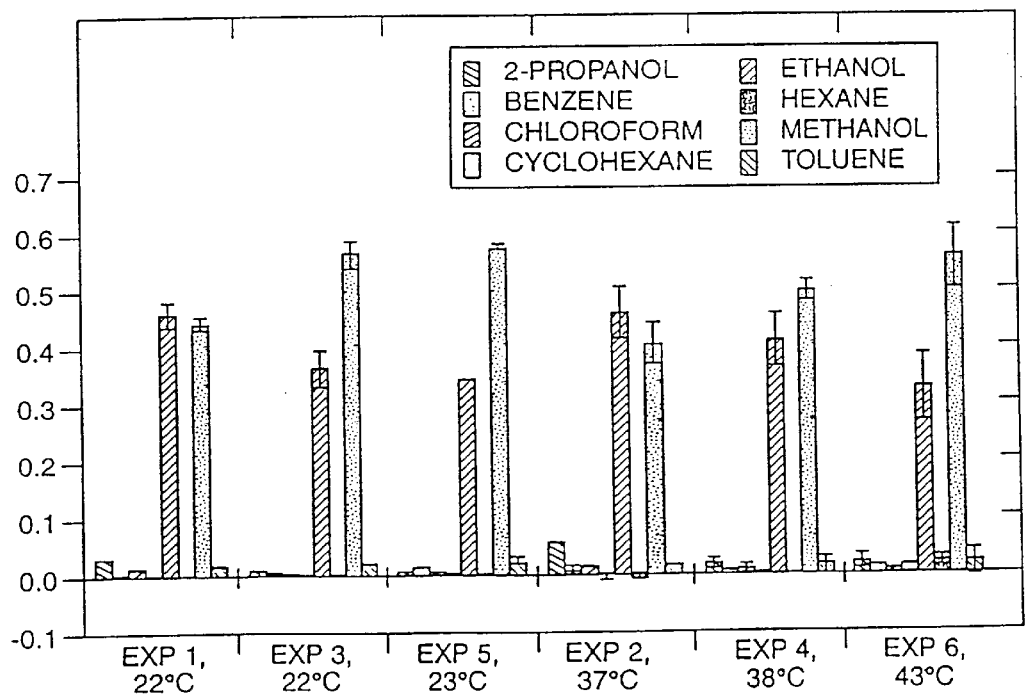
FIG._12M

SENSORS FOR DETECTING ANALYTES IN FLUIDS

This application is a continuation of and claims the benefit of U.S. Continuation application Ser. No. 09/258,713, filed Feb. 26, 1999 now U.S. Pat. No. 6,093,308, which is a Continuation application of Ser. No. 08/949,730, filed Oct. 14, 1997, now U.S. Pat. No. 5,911,872, which is a Continuation application of Ser. No. 08/696,128, filed Aug. 14, 1996, now U.S. Pat. No. 5,788,833, which is a Continuation-in-Part application of Ser. No. 08/410,809, filed Mar. 27, 1995, now U.S. Pat. No. 5,571,401, the disclosures of which are incorporated by reference.

The research carried out in the subject application was supported in part by grants from the National Science Foundation (CHE 9202583), was made during the performance of work under a NASA contract, and is subject to the provisions of Public Law 96-517 (35 U.S.C. § 202). The government may have rights in any patent issuing on this application.

INTRODUCTION

1. Field of the Invention

The field of the invention is electrical sensors for detecting analyses in fluids.

2. Background

There is considerable interest in developing sensors that act as analogs of the mammalian olfactory system (Lundström el al. (1991) *Nature* 352:47–50, Shurmer and Gardner (1992) *Sens. Act. B* 8:1–11). This system is thought to utilize probabilistic repertoires of many different receptors to recognize a single odorant (Reed (1992) *Neuron* 8:205–209; Lancet and Ben-Airie (1993) *Curr. Biol.* 3:668–674). In such a configuration, the burden of recognition is not on highly specific receptors, as in the traditional "lock-and-key" molecular recognition approach to chemical sensing, but lies instead on the distributed pattern processing of the olfactory bulb and the brain (Kauer (1991) *TINS* 14:79–85, DeVries and Baylor (1993) *Cell* 10(S):139–149). Prior attempts to produce a broadly responsive sensor array have exploited heated metal oxide thin film resistors (Gardner et al. (1991) *Sens. Act. B* 4 117–121; Gardner et al. (1991) *Sens. Act. B* 6:71–75; Corcoran et al. (1993) *Sens. Act. B* 15:32–37), polymer sorption layers on the surfaces of acoustic wave resonators (Grate and Abraham (1991) *Sens. Act. B* 3:85–111; Grate et al. (1993) *Anal. Chem.* 65:1868–1881), arrays of electrochemical detectors (Stetter et al. (1986) *Anal. Chem.* 58:860–866; Stetter et al. (1990) *Sens. Act. B* 1:43–47; Stetter et al. (1993) *Anal. Chem. Acta* 284:1–11), or conductive polymers (Pearce et al. (1993) *Analyst* 118:371–377; Shurmer et al. (1991) *Sens. Act. B* 4:29–33). Arrays of metal oxide thin film resistors, typically based on $SnO_2$ films that have been coated with various catalysts, yield distinct, diagnostic responses for several vapors (Gardner et al. (1991) *Sens. Act. B* 4:117–121; Gardner et al. (1991) *Sens. Act. B* 6:71–75; Corcoran et al. (1993) *Sens. Act. B* 15:32–37). However, due to the lack of understanding of catalyst function, $SnO_2$ arrays do not allow deliberate chemical control of the response of elements in the arrays nor reproducibility of response from array to array. Surface acoustic wave resonators are extremely sensitive to both mass and acoustic impedance changes of the coatings in array elements, but the signal transduction mechanism involves somewhat complicated electronics, requiring frequency measurement to 1 Hz while sustaining a 100 MHz Rayleigh wave in the crystal (Grate and Abraham (1991) *Sens. Act. B* 3:85–111; Grate et al. (1993) *Anal. Chem.* 65:1868–1881). Attempts have been made to construct sensors with conducting polymer elements that have been grown electrochemically through nominally identical polymer films and coatings (Pearce et al. (1993) *Analyst* 118:371–377; Shurmer et al. (1991) *Sens. Act. B* 4:29–33; Topart and Josowicz (1992) *J. Phys. Chem.* 96:7824–7830, Charlesworth et al. (1993) *J. Phys. Chem.* 97:5418–5423).

It is an object herein to provide a broadly responsive analyte detection sensor based on one or more "chemiresistor" elements. Such elements are simply prepared and are readily modified chemically to respond to a broad range of analytes. Such elements may also respond to temperature and current variation. In addition, these sensors yield a rapid, low power, dc electrical signal in response to the fluid of interest, and their signals are readily integrated with software or hardware-based neural networks for purposes of analyte identification.

Relevant Literature

Pearce et al. (1993) *Analyst* 118:371–377 and Gardner et al. (1994) *Sensors and Actuators B* 18–19:240–243 describe polypyrrole-based sensor arrays for monitoring beer flavor. Shurmer (1990) U.S. Pat. No. 4,907,441, describes general sensor arrays with particular electrical circuitry.

SUMMARY OF THE INVENTION

The invention provides methods, apparatuses and systems for detecting and identifying analytes in fluids. In one embodiment, the apparatuses include a chemical sensor comprising first and second conductive elements (e.g., electrical leads) electrically coupled to a chemically sensitive resistor which provides an electrical path between the conductive elements. The resistor comprises a plurality of alternating nonconductive regions (comprising a nonconductive organic polymer) and conductive regions (comprising a conductive material). The electrical path between the first and second conductive elements is transverse to (i.e., passes through) said plurality of alternating nonconductive and conductive regions. In use, the resistor provides a difference in resistance between the conductive elements when contacted with a fluid comprising a chemical analyte at a first concentration, than when contacted with a fluid comprising the chemical analyte at a second different concentration.

The electrical path through any given nonconductive region is typically on the order of 100 angstroms in length, providing a resistance of on the order of 100 mΩ across the region. Variability in chemical sensitivity from sensor to sensor is conveniently provided by qualitatively or quantitatively varying the composition of the conductive and/or nonconductive regions. For example, in one embodiment, the conductive material in each resistor is held constant (e.g., the same conductive material such as polypyrrole) while the nonconductive organic polymer varies between resistors (e.g., different plastics such as polystyrene).

Arrays of such sensors are constructed with at least two sensors having different chemically sensitive resistors providing dissimilar differences in resistance. An electronic nose for detecting an analyte in a fluid may be constructed by using such arrays in conjunction with an electrical measuring device electrically connected to the conductive elements of each sensor. Such electronic noses may incorporate a variety of additional components including means for monitoring the temporal response of each sensor, assembling and analyzing sensor data to determine analyte identity, etc. Methods of making and using the disclosed sensors, arrays and electronic noses are also provided.

In another embodiment, the sensor for detecting the presence of a chemical analyte in a fluid comprises a chemically sensitive resistor electrically connected to an electrical measuring apparatus where the resistor is in thermal communication with a temperature control apparatus. The chemically sensitive resistor comprises a mixture of a nonconductive organic polymer and a conductive material compositionally different than said nonconductive organic polymer and provides an electrical path therethrough. The chemically sensitive resistor provides varying electrical resistances ($R_m$) at varying temperatures ($T_m$) when contacted with a fluid comprising a particular chemical analyte.

Such sensors also function to provide an electrical impedance $Z_m$ at frequency $\omega_m$ when contacted with a fluid comprising a chemical analyte, where m is an integer greater than 1 and $\omega_m$ does not equal 0. Finally, such sensors may also provide an electrical impedance $Z_{m,n}$ at frequency $\omega_m$ and temperature $T_n$ when contacted with a fluid comprising a chemical analyte, where m and/or n is an integer greater than 1. The invention is also directed to systems and methods for employing such sensors for the detection of a chemical analyte in a fluid.

BRIEF DESCRIPTION OF THE FIGURES

FIGS. 1A and 1A–I show an overview of sensor design; FIG. 1B shows an overview of sensor operation, FIG. 1C shows an overview of system operation.

FIG. 2 shows cyclic voltammogram of a poly(pyrrole)-coated platinum electrode. The electrolyte was 0.10 M $[(C_4H_9)_4N]^+[ClO_4]^-$ in acetonitrile, with a scan rate of 0.10 V $s^{-1}$.

FIG. 3A shows the optical spectrum of a spin coated poly(pyrrole) film that had been washed with methanol to remove excess pyrrole and reduced phosphomolybdic acid.

FIG. 3B shows the optical spectrum of a spin-coated poly(pyrrole) film on indium-tin-oxide after 10 potential cycles between +0.70 and −1.00 V vs. SCE in 0.10 M $[(C_4H_9)_4N]^+[ClO_4]^-$ in acetonitrile at a scan rate of 0.10 V-$s^{-1}$. The spectra were obtained in 0.10 M KCl—$H_2O$.

FIGS. 4A and 4A–I are a schematic of a sensor array showing an enlargement of one of the modified ceramic capacitors used as sensing elements. The response patterns generated by the sensor array described in Table 3 are displayed for: FIG. 4B acetone, FIG. 4C benzene, and FIG. 4D ethanol.

FIG. 5 is a principle component analysis of autoscaled data from individual sensors containing different plasticizers. The numbers in the upper right hand corner of each square refer to the different sensor elements described in Table 3.

FIGS. 6A and 6B are principle component analysis of data obtained from all sensors (Table 3). Conditions and symbols are identical to FIGS. 5A–5D. FIG. 6A shows data represented in the first three principle components pc1, pc2 and pc3, while FIG. 6B shows the data when represented in pc1, pc2, and pc4. A higher degree of discrimination between some solvents could be obtained by considering the fourth principle component as illustrated by larger separations between chloroform, tetrahydrofuran, and isopropyl alcohol in FIG. 6B.

FIG. 7A is a plot of acetone partial pressure (O) as a function of the first principle component, linear least square fit (−) between the partial pressure of acetone and the first principle component ($P_a$=8.26·pc1+83.4, $R^2$=0.989); acetone partial pressure (+) predicted from a multi-linear least square fit between the partial pressure of acetone and the first three principle components ($P_a$=8.26·pc1−0.673·pc2+6.25·pc3+83.4, $R^2$=0.998). FIG. 7B is a plot of the mole fraction of methanol, $x_m$, (O) in a methanol—ethanol mixture as a function of the first principle component, linear least square fit (−) between $x_m$ and the first principle component ($x_m$=0.112·pc1+0.524, $R^2$=0.979); $x_m$ predicted from a multi-linear least square fit (+) between $x_m$ and the first three principle components ($x_m$=0.112·pc1−0.0300·pc2−0.0444·pc3+0.524, R =0.987).

FIG. 8 is the resistance response of a poly(N-vinylpyrrolidone):carbon black (20 w/w % carbon black) sensor element to methanol, acetone, and benzene. The analyte was introduced at t=60 s for 60 s. Each trace is normalized by the resistance of the sensor element (approx. 125 Ω) before each exposure.

FIG. 9 is the first three principal components for the response of a carbon-black based sensor array with 10 element. The non-conductive components of the carbon-black composites used are listed in Table 3, and the resistors were 20 w/w % carbon black.

FIGS. 10A and 10B are a schematic illustration of the sensor employed to measure the effect of temperature on differential resistance responses to various chemical analytes.

FIGS. 11A–11M are graphical representations of the data presented in Table 6 which is the average resistance measured by each sensor employed and for each of the eight analytes tested.

FIGS. 12A–12M are graphical representations of the data presented in Table 7 which is the normalized average resistance measured by each sensor employed and for each of the either analytes tested.

DETAILED DESCRIPTION OF THE INVENTION

The invention provides sensor arrays for detecting an analyte in a fluid for use in conjunction with an electrical measuring apparatus. These arrays comprise a plurality of compositionally different chemical sensors. Each sensor comprises at least first and second conductive leads electrically coupled to and separated by a chemically sensitive resistor. The leads may be any convenient conductive material, usually a metal, and may be interdigitized to maximize signal-to-noise strength.

The resistor comprises a plurality of alternating nonconductive and conductive regions transverse to the electrical path between the conductive leads. Generally, the resistors are fabricated by blending a conductive material with a nonconductive organic polymer such that the electrically conductive path between the leads coupled to the resistor is interrupted by gaps of non-conductive organic polymer material. For example, in a colloid, suspension or dispersion of particulate conductive material in a matrix of nonconductive organic polymer material, the matrix regions separating the particles provide the gaps. The nonconductive gaps range in path length from about 10 to 1,000 angstroms, usually on the order of 100 angstroms providing individual resistance of about 10 to 1,000 mΩ, usually on the order of 100 mΩ, across each gap. The path length and resistance of a given gap is not constant but rather is believed to change as the nonconductive organic polymer of the region absorbs, adsorbs or imbibes an analyte. Accordingly, the dynamic aggregate resistance provided by these gaps in a given resistor is a function of analyte permeation of the nonconductive regions. In some embodiments, the conductive material may also contribute to the dynamic aggregate resistance as a function of analyte permeation (e.g., when the conductive material is a conductive organic polymer such as polyprryole).

A wide variety of conductive materials and nonconductive organic polymer materials can be used. Table 1 provides exemplary conductive materials for use in resistor fabrication; mixtures, such as of those listed, may also be used. Table 2 provides exemplary nonconductive organic polymer materials, blends and copolymers, such as of the polymers listed here, may also be used . Combinations, concentrations, blend stoichiometries, percolation thresholds, etc. are readily determined empirically by fabricating and screening prototype resistors (chemiresistors) as described below.

TABLE 1

| Major Class | Examples |
| --- | --- |
| Organic Conductors | conducting polymers (poly(anilines), poly(thiophenes), poly(pyrroles), poly(acetylenes), etc.)), carbonaceous materials (carbon blacks, graphite, coke, $C_{60}$, etc.), charge transfer complexes (tetramethylparaphenylenediamine-chloranile, alkali metal tetracyanoquinodimethane complexes, tetrathiofulvalene halide complexes, etc.), etc. |
| Inorganic Conductors | metals and metal alloys (Ag, Au, Cu, Pt, AuCu alloy, etc.), highly doped semiconductors (Si, GaAs, Inp, $MoS_2$, $TiO_2$, etc.), conductive metal oxides ($In_2O_3$, $SnO_2$, $Na_xPt_3O_4$, etc.), superconductors ($YBa_2Cu_3O_7$, $Tl_2Ba_2Ca_2Cu_3O_{10}$, etc.), etc. |
| Mixed inorganic/organic Conductors | Tetracyanoplatinate complexes, Iridium halocarbonyl complexes, stacked macrocyclic complexes, etc. |

TABLE 2

| Major Class | Examples |
| --- | --- |
| Main-chain carbon polymers | poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitriles), poly(vinyl esters), poly(styrenes), poly(arylenes), etc. |
| Main-chain acyclic heteroatom polymers | poly(oxides), poly(carbonates), poly(esters), poly(anhydrides), poly(urethanes), poly(sufonates), poly(siloxanes), poly(sulfides), poly(thioesters), poly(sulfones), poly(sulionamides), poly(amides), poly(ureas), poly(phosphazenes), poly(silanes), poly(silazanes) etc. |
| Main-chain heterocyclic polymers. | poly(furan tetracarboxylic acid diimides), poly(benzoxazoles), poly(oxadiazoles), poly(benzothiazinophenothiazines); poly(benzothiazoles), poly(pyrazinoquinoxalines), poly(pyromellitimides), poly(quinoxalines), poly(benzimidazoles), poly(oxindoles), poly(oxoisoindolines), poly(dioxoisoindolines), poly(triazines), poly(pyridazines), poly(piperazines), poly(pyridines), poly(piperidines), poly(triazoles), |

TABLE 2-continued

| Major Class | Examples |
| --- | --- |
| | poly(pyrazoles), poly(pyrrolidines), poly(carboranes), poly(oxabicyclononanes), poly(dibenzofurans), poly(phthalides), poly(acetals), poly(anhydrides), carbohydrates, etc. |

The chemiresistors can be fabricated by many techniques such as, but not limited to, solution casting, suspension casting, and mechanical mixing. In general, solution cast routes are advantageous because they provide homogeneous structures and ease of processing. With solution cast routes, resistor elements may be easily fabricated by spin, spray or dip coating. Since all elements of the resistor must be soluble, however, solution cast routes are somewhat limited in their applicability. Suspension casting still provides the possibility of spin, spray or dip coating but more heterogeneous structures than with solution casting are expected. With mechanical mixing, there are no solubility restrictions since it involves only the physical mixing of the resistor components, but device fabrication is more difficult since spin, spray and dip coating are no longer possible. A more detailed discussion of each of these follows.

For systems where both the conducting and non-conducting media or their reaction precursors are soluble in a common solvent, the chemiresistors can be fabricated by solution casting. The oxidation of pyrrole by phosphomolybdic acid presented herein represents such a system. In this reaction, the phosphomolybdic acid and pyrrole are dissolved in tetrahydrofuran (THF) and polymerization occurs upon solvent evaporation. This allows for THF soluble non-conductive polymers to be dissolved into this reaction mixture thereby allowing the blend to be formed in a single step upon solvent evaporation. The choice of non-conductive polymers in this route is, of course, limited to those that are soluble in the reaction media. For the poly (pyrrole) case described above, preliminary reactions were performed in THF, but this reaction should be generalizable to other non-aqueous solvent such as acetonitrile or ether. A variety of permutations on this scheme are possible for other conducting polymers. Some of these are listed below. Certain conducting polymers, such as substituted poly (cyclooctatetraenes), are soluble in their undoped, non-conducting state in solvents such as THF or acetonitrile. Consequently, the blends between the undoped polymer and plasticizing polymer can be formed from solution casting. After which, the doping procedure (exposure to $I_2$ vapor, for instance) can be performed on the blend to render the substituted poly(cyclooctatetraene) conductive. Again, the choice of non-conductive polymers is limited to those that are soluble in the solvents that the undoped conducting polymer is soluble in and to those stable to the doping reaction. Certain conducting polymers can also be synthesized via a soluble precursor polymer. In these cases, blends between the precursor polymer and the non-conducting polymer can first be formed followed by chemical reaction to convert the precursor polymer into the desired conducting polymer. For instance poly(p-phenylene vinylene) can be synthesized through a soluble sulfonium precursor. Blends between this sulfonium precursor and the non-conductive polymer can be formed by solution casting. After which, the blend can be subjected to thermal treatment under vacuum to convert the sulfonium precursor to the desired poly(p-phenylene vinylene).

In suspension casting, one or more of the components of the resistor is suspended and the others dissolved in a common solvent. Suspension casting is a rather general technique applicable to a wide range of species, such as carbon blacks or colloidal metals, which can be suspended in solvents by vigorous mixing or sonication. In one application of suspension casting, the non-conductive polymer is dissolved in an appropriate solvent (such as THF, acetonitrile, water, etc.). Colloidal silver is then suspended in this solution and the resulting mixture is used to dip coat electrodes.

Mechanical mixing is suitable for all of the conductive/ non-conductive combinations possible. In this technique, the materials are physically mixed in a ball-mill or other mixing device. For instance, carbon black:non-conductive polymer composites are readily made by ball-milling. When the non-conductive polymer can be melted or significantly softened without decomposition, mechanical mixing at elevated temperature can improve the mixing process. Alternatively, composite fabrication can sometimes be improved by several sequential heat and mix steps.

Once fabricated, the individual elements can be optimized for a particular application by varying their chemical make up and morphologies. The chemical nature of the resistors determines to which analytes they will respond and their ability to distinguish different analytes. The relative ratio of conductive to insulating components determines the magnitude of the response since the resistance of the elements becomes more sensitive to sorbed molecules as the percolation threshold is approached. The film morphology is also important in determining response characteristics. For instance, thin films respond more quickly to analytes than do thick ones. Hence, with an empirical catalogue of information on chemically diverse sensors made with varying ratios of insulating to conducting components and by differing fabrication routes, sensors can be chosen that are appropriate for the analytes expected in a particular application, their concentrations, and the desired response times. Further optimization can then be performed in an iterative fashion as feedback on the performance of an array under particular conditions becomes available.

The resistor may itself form a substrate for attaching the lead or the resistor. For example, the structural rigidity of the resistors may be enhanced through a variety of techniques:chemical or radiation cross-linking of polymer components (dicumyl peroxide radical cross-linking, UV-radiation cross-linking of poly(olefins), sulfur cross-linking of rubbers, e-beam cross-linking of Nylon, etc.), the incorporation of polymers or other materials into the resistors to enhance physical properties (for instance, the incorporation of a high molecular weight, high transition metal (Tm) polymers), the incorporation of the resistor elements into supporting matrices such as clays or polymer networks (forming the resistor blends within poly- (methylmethacrylate) networks or within the lamellae of montmorillonite, for instance), etc. In another embodiment, the resistor is deposited as a surface layer on a solid matrix which provides means for supporting the leads. Typically, the matrix is a chemically inert, non-conductive substrate such as a glass or ceramic.

Sensor arrays particularly well-suited to scaled up production are fabricated using integrated circuit (IC) design technologies. For example, the chemiresistors can easily be integrated onto the front end of a simple amplifier interfaced to an A/D converter to efficiently feed the data stream directly into a neural network software or hardware analysis section. Micro-fabrication techniques can integrate the chemiresistors directly onto a micro-chip which contains the circuitry for analogue signal conditioning/processing and then data analysis. This provides for the production of millions of incrementally different sensor elements in a single manufacturing step using ink-jet technology. Controlled compositional gradients in the chemiresistor elements of a sensor array can be induced in a method analogous to how a color ink-jet printer deposits and mixes multiple colors. However, in this case rather than multiple colors, a plurality of different polymers in solution which can be deposited are used. A sensor array of a million distinct elements only requires a 1 cm×1 cm sized chip employing lithography at the 10 $\mu$m feature level, which is within the capacity of conventional commercial processing and deposition methods. This technology permits the production of sensitive, small-sized, stand-alone chemical sensors.

Preferred sensor arrays have a predetermined inter-sensor variation in the structure or composition of the nonconductive organic polymer regions. The variation may be quantitative and/or qualitative. For example, the concentration of the nonconductive organic polymer in the blend can be varied across sensors. Alternatively, a variety of different organic polymers may be used in different sensors. An electronic nose for detecting an analyte in a fluid is fabricated by electrically coupling the sensor leads of an array of compositionally different sensors to an electrical measuring device. The device measures changes in resistivity at each sensor of the array, preferably simultaneously and preferably over time. Frequently, the device includes signal processing means and is used in conjunction with a computer and data structure for comparing a given response profile to a structure-response profile database for qualitative and quantitative analysis. Typically such a nose comprises at least ten, usually at least 100, and often at least 1000 different sensors though with mass deposition fabrication techniques described herein or otherwise known in the art, arrays of on the order of at least $10^6$ sensors are readily produced.

In operation, each resistor provides a first electrical resistance between its conductive leads when the resistor is contacted with a first fluid comprising a chemical analyte at a first concentration, and a second electrical resistance between its conductive leads when the resistor is contacted with a second fluid comprising the same chemical analyte at a second different concentration. Moreover, a resistor may provide a first electrical resistance when the resistor is contacted with a first fluid comprising a first chemical analyte at a concentration $C_m$ and a second electrical resistance when the resistor is contacted with a second fluid comprising a second, different chemical analyte at concentration $C_n$, wherein $C_m$ and $C_n$ may be the same or different. The fluids may be liquid or gaseous in nature. The first and second fluids may reflect samples from two different environments, a change in the concentration of an analyte in a fluid sampled at two time points, a sample and a negative control, etc. The sensor array necessarily comprises sensors which respond differently to a change in an analyte concentration, i.e., the difference between the first and second electrical resistance of one sensor is different from the difference between the first second electrical resistance of another sensor.

In a preferred embodiment, the temporal response of each sensor (resistance as a function of time) is recorded. The temporal response of each sensor may be normalized to a maximum percent increase and percent decrease in resistance which produces a response pattern associated with the exposure of the analyte. By iterative profiling of known analytes, a structure-function database correlating analytes and response profiles is generated. Unknown analyte may then be characterized or identified using response pattern comparison and recognition algorithms. Accordingly, analyte detection systems comprising sensor arrays, an electrical measuring devise for detecting resistance across each chemiresistor, a computer, a data structure of sensor array response profiles, and a comparison algorithm are provided. In another embodiment, the electrical measuring device is an integrated circuit comprising neural network-based hardware and a digital-analog converter (DAC) multiplexed to each sensor, or a plurality of DACs, each connected to different sensor(s).

A wide variety of analytes and fluids may be analyzed by the disclosed sensors, arrays and noses so long as the subject analyte is capable generating a differential response across a plurality of sensors of the array. Analyte applications include broad ranges of chemical classes such as organics such as alkanes, alkenes, alkynes, dienes, alicyclic hydrocarbons, arenes, alcohols, ethers, ketones, aldehydes, carbonyls, carbanions, polynuclear aromatics and derivatives of such organics, e.g., halide derivatives, etc., biomolecules such as sugars, isoprenes and isoprenoids, fatty acids and derivatives, etc. Accordingly, commercial applications of the sensors, arrays and noses include environmental toxicology and remediation, biomedicine, materials quality control, food and agricultural products monitoring, etc.

The general method for using the disclosed sensors, arrays and electronic noses, for detecting the presence of an analyte in a fluid involves resistively sensing the presence of an analyte in a fluid with a chemical sensor comprising first and second conductive leads electrically coupled to and separated by a chemically sensitive resistor as described above by measuring a first resistance between the conductive leads when the resistor is contacted with a first fluid comprising an analyte at a first concentration and a second different resistance when the resistor is contacted with a second fluid comprising the analyte at a second different concentration.

In another embodiment, the sensor for detecting the presence of a chemical analyte in a fluid comprises a chemically sensitive resistor electrically connected to an electrical measuring apparatus where the resistor is in thermal communication with a temperature control apparatus. As described above, the chemically sensitive resistor(s) comprise a mixture of a nonconductive organic polymer and a conductive material which is compositionally different than the nonconductive organic polymer. The chemically sensitive resistor provides an electrical path through which electrical current may flow and a resistance (R) at a temperature (T) when contacted with a fluid comprising a chemical analyte.

In operation, the chemically sensitive resistor(s) of the sensor for detecting the presence of a chemical analyte in a fluid provide an electrical resistance ($R_m$) when contacted with a fluid comprising a chemical analyte at a particular temperature ($T_m$). The electrical resistance observed may vary as the temperature varies, thereby allowing one to define a unique profile of electrical resistances at various different temperatures for any chemical analyte of interest. For example, a chemically sensitive resistor, when contacted with a fluid comprising a chemical analyte of interest, may provide an electrical resistance $R_m$ at temperature $T_m$ where m is an integer greater than 1, and may provide a different electrical resistance $R_n$ at a different temperature $T_n$. The difference between $R_m$ and $R_n$ is readily detectable by an electrical measuring apparatus.

As such, the chemically sensitive resistor(s) of the sensor are in thermal communication with a temperature control apparatus, thereby allowing one to vary the temperature at which electrical resistances are measured. If the sensor comprises an array of two or more chemically sensitive resistors each being in thermal communication with a temperature control apparatus, one may vary the temperature across the entire array (i.e., generate a temperature gradient across the array), thereby allowing electrical resistances to be measured simultaneously at various different temperatures and various different resistor compositions. For example, in an array of chemically sensitive resistors, one may vary the composition of the resistors in the horizontal direction across the array, such that resistor composition in the vertical direction across the array remains constant. One may then create a temperature gradient in the vertical direction across the array, thereby allowing the simultaneous analysis of chemical analytes at different resistor compositions and different temperatures.

Methods for placing chemically sensitive resistors in thermal communication with a temperature control apparatus are readily apparent to those skilled in the art and include, for example, attaching a heating element to the sensor and passing electrical current through said heating element. The temperature range across which electrical resistances may be measured will be a function of the resistor composition, for example the melting temperature of the resistor components, the thermal stability of the analyte of interest or any other component of the system, and the like. For the most part, the temperature range across which electrical resistance will be measured will be about 20° C. to 80° C., preferably from about 22° C. to about 70° C. and more preferably from about 22° C. to 65° C.

In yet another embodiment, rather than subjecting the sensor to a direct electrical current and measuring the true electrical resistance through the chemically sensitive resistor (s), the sensor can be subjected to an alternating electrical current at different frequencies to measure impedance. Impedance is the apparent resistance in an alternating electrical current as compared to the true electrical resistance in a direct current. As such, the present invention is also directed to a sensor for detecting the presence of a chemical analyte in a fluid, said sensor comprising a chemically sensitive resistor electrically connected to an electrical measuring apparatus, said chemically sensitive resistor comprising a mixture of nonconductive organic polymer and a conductive material compositionally different than said nonconductive organic polymer and wherein said resistor provides (a) an electrical path through said mixture of nonconductive organic polymer and said conductive material, and (b) an electrical impedance $Z_m$ at frequency $\omega_m$ when contacted with a fluid comprising said chemical analyte, where m is an integer greater than 1 and $\omega_m$ does not equal 0. For measuring impedance as a function of frequency, the frequencies employed will generally range from about 1 Hz to 5 GHz, usually from about 1 MHz to 1 GHz, more usually from about 1 MHz to 10 MHz and preferably from about 1 MHz to 5 MHz. Chemical analytes of interest will exhibit unique impedance characteristics at varying alternating current frequencies, thereby allowing one to detect the presence of any chemical analyte of interest in a fluid by measuring $Z_m$ at alternating frequency $\omega_m$.

For performing impedance measurements, one may employ virtually any impedance analyzer known in the art. Preferably, a Schlumberger Model 1260 Impedance/Gain-Phase Analyzer (Schlumberger Technologies, Farnborough, Hampshire, England) with approximately 6 inch RG174 coaxial cables is employed. In such an apparatus, the resistor/sensor is held in an A1 chassis box to shield them from external electronic noise.

In still another embodiment of the present invention, one may vary both the frequency $\omega_m$ of the electrical current employed and the temperature $T_n$ and measure the electrical impedance $Z_{m,n}$, thereby allowing for the detection of the presence of a chemical analyte of interest. As such, the present invention is also directed to a sensor for detecting the presence of a chemical analyte in a fluid, said sensor comprising a chemically sensitive resistor electrically connected to an electrical measuring apparatus and being in thermal communication with a temperature control apparatus, said chemically sensitive resistor comprising a mixture of nonconductive organic polymer and a conductive material compositionally different than said nonconductive organic polymer, wherein said resistor provides (1) an electrical path through said mixture of nonconductive organic polymer and said conductive material, and (2) an electrical impedance $Z_{m,n}$ at frequency $\omega_m$ and temperature $T_n$ when contacted with a fluid comprising said chemical analyte, where m and/or n is an integer greater than 1. For measuring impedance as a function of frequency and temperature, the frequencies employed will generally not be higher than 10 MHz, preferably not higher than 5 MHz. Chemical analytes of interest will exhibit unique impedance characteristics at varying alternating current frequencies and varying temperatures, thereby allowing one to detect the presence of any chemical analyte of interest in a fluid by measuring $Z_{m,n}$ at frequency $\omega_m$ and temperature $T_n$.

The present invention is also directed to systems and methods for employing the above described sensors for detecting the presence of a chemical analyte in a fluid.

The following examples are offered by way of illustration and not by way of limitation.

EXAMPLES

I. Sensor Arrays

Polymer Synthesis

Poly(pyrrole) films used for conductivity, electrochemical, and optical measurements were prepared by injecting equal volumes of $N_2$-purged solutions of pyrrole (1.50 mmoles in 4.0 ml dry tetrahydrofuran) and phosphomolybdic acid (0.75 mmoles in 4.0 ml tetrahydrofuran) into a $N_2$-purged test tube. Once the two solutions were mixed, the yellow phosphomolybdic acid solution turned dark green, with no observable precipitation for several hours. This solution was used for film preparation within an hour of mixing.

Sensor Fabrication

Plasticized poly(pyrrole) sensors were made by mixing two solutions, one of which contained 0.29 mmoles pyrrole in 5.0 ml tetrahydrofuran, with the other containing 0.25 mmoles phosphomolybdic acid and 30 mg of plasticizer in 5.0 ml of tetrahydrofuran. The mixture of these two solutions resulted in a w:w ratio of pyrrole to plasticizer of 2:3. An inexpensive, quick method for crating the chemiresistor array elements was accomplished by effecting a cross sectional cut through commercial 22 nF ceramic capacitors (Kemet Electronics Corporation). Mechanical slices through these capacitors revealed a series of interdigitated metal lines (25% Ag:75% Pt), separated by 15 $\mu$m, that could be readily coated with conducting polymer. The monomer—plasticizer—oxidant solutions were then used to dip coat interdigitated electrodes in order to provide a robust electrical contact to the polymerized organic films. After polymerization was complete, the film was insoluble and was rinsed with solvent (tetrahydrofuran or methanol) to remove residual phosphomolybdic acid and unreacted monomer. The sensors were then connected to a commercial bus strip, with the resistances of the various "chemiresistor" elements readily monitored by use of a multiplexing digital ohmmeter.

Instrumentation

Optical spectra were obtained on a Hewlett Packard 8452A spectrophotometer, interfaced to an IBM XT. Electrochemical experiments were performed using a Princeton Applied Research Inc. 173 potentiostat/175 universal programmer. All electrochemical experiments were performed with a Pt flag auxiliary and a saturated calomel reference electrode (SCE). Spin-coating was performed on a Headway Research Inc. photoresist spin coater. Film thicknesses were determined with a Dektak Model 3030 profilometer. Conductivity measurements were performed with an osmium-tipped four point probe (Alessi Instruments Inc., tip spacing=0.050", tip radii=0.010"). Transient resistance measurements were made with a conventional multimeter (Fluke Inc., "Hydra Data Logger" Meter).

Principle Component Analysis and Multi-linear Least Square Fits. A data set obtained from a single exposure of the array to an odorant produced a set of descriptors (i.e., resistances), $d_i$. The data obtained from multiple exposures thus produced a data matrix D where each row, designated by j, consisted of n descriptors describing a single member of the data set (i.e., a single exposure to an odor). Since the baseline resistance and the relative changes in resistance varied among sensor,s the data matrix was autoscaled before further processing (Hecht (1990) *Mathematics in Chemistry: An Introduction to Modern Methods* (Prentice Hall, Englewood Cliffs, N.J.)). In this preprocessing technique, all the data associated with a single descriptor (i.e., a column in the data matrix) were centered around zero with unit standard deviation $$d'_{ij}=(d_{ij}-\bar{d}_i)/\sigma_i \tag{1}$$

where $\bar{d}_i$ is the mean value for descriptor i and $\sigma_i$ is the corresponding standard deviation.

Principle component analysis (Hecht (1990)) was performed to determine linear combinations of the data such that the maximum variance [defined as the square of the standard deviation] between the members of the data set was obtained in n mutually orthogonal dimensions. The linear combinations of the data resulted in the largest variance [or separation] between the members of the data set in the first principle component (pc1) and produced decreasing magnitudes of variance from the second to the $n^{th}$ principle component (pc2–pcn). The coefficients required to transform the autoscaled data into principle component space (by linear combination) were determined by multiplying the data matrix, D, by its transpose, $D^T$ (i.e., diagnolizing the matrix) (Hecht (1990) *Mathematics in Chemistry: An Introduction to Modern Methods* (Prentice Hall, Englewood Cliffs, N.J.))

$$R=D^T \cdot D \tag{2}$$

This operation produced the correlation matrix, R whose diagonal elements were unity and whose off-diagonal elements were the correlation coefficients of the data. The total variance in the data was thus given by the sum of the diagonal elements in R. The n eigenvalues, and the corresponding n eigenvectors, were then determined for R. Each eigenvector contained a set of n coefficients which were used to transform the data by linear combination into one of its n principle components. The corresponding eigenvalue yielded the fraction of the total variance that was contained in that principle component. This operation produced a principle component matrix, P, which had the same dimensions as the original data matrix. Under these conditions, each row of the matrix P was still associated with a particular odor and each column was associated with a particular principle component.

Since the values in the principle component space had no physical meaning, it was useful to express the results of the principle component analysis in terms of physical parameters such as partial pressure and mole fraction. This was achieved via a multi-linear least square fit between the principle component values and the corresponding parameter of interest. A multi-linear least square fit resulted in a linear combination of the principle components which yielded the best fit to the corresponding parameter value. Fits were achieved by appending a column with each entry being unity to the principle component matrix P, with each row, j, corresponding to a different parameter value (e.g., partial pressure), $v_j$, contained in vector V. The coefficients for the best multi-linear fit between the principle components and parameter of interest were obtained by the following matrix operation $$C=(P^T \cdot P)^{-1} \cdot P^T \cdot V \tag{3}$$

where C was a vector containing the coefficients for the linear combination.

A key to our ability to fabricate chemically diverse sensing elements was the preparation of processable, air stable films of electrically conducting organic polymers. This was achieved through the controlled chemical oxidation of pyrrole (PY) using phosphomolybdic acid ($H_3PMo_{12}O_{40}$) (20 in tetrahydrofuran:

$$PY \rightarrow PY^+ + e^- \tag{4}$$

$$2PY^+ \rightarrow PY_2 + 2H^+ \tag{5}$$

$$H_3PMo_{12}O_{40} + 2e^- + 2H^+ \rightarrow H_5PMo_{12}O_{40} \tag{6}$$

The redox-driven or electrochemically-induced polymerization of pyrrole has been explored previously, but this process typically yields insoluble, intractable deposits of poly(pyrrole) as the product (Salmon et al. (1982) *J. Polym. Sci., Polym. Lett.* 20:187–193). Our approach was to use low concentrations of the $H_3PMo_{12}O_{40}$ oxidant (E°=+0.36 V vs. SCE) (Pope (1983) Heteropoly and Isopoly Oxoinetalates (Springer-Verlag, New York), Chap. 4). Since the electrochemical potential of $PY^+/PY$ is more positive (E°=+1.30 V vs. SCE) (Andrieux et al. (1990) *J. Am. Chem. Soc.* 112:2439–2440) than that of $H_3PMo_{12}O_{40}/H_5PMo_{12}O_{40}$, the equilibrium concentration of $PY^+$, and thus the rate of polymerization, was relatively low in dilute solutions (0.19 M PY, 0.09 M $H_3PMo_{12}O_{40}$). However, it has been shown that the oxidation potential of pyrrole oligomers decreases from +1.20 V to +0.55 to +0.26 V vs. SCE as the number of units increase from one to two to three, and that the oxidation potential of bulk poly(pyrrole) occurs at −0.10 V vs. SCE (Diaz et al. (1981) *J. Electroanal. Chem.* 121:355–361). As a result, oxidation of pyrrole trimers by phosphomolybdic acid is expected to be thermodynamically favorable. This allowed processing of the monomer-oxidant solution (i.e., spin coating, dip coating, introduction of plasticizers, etc.), after which time polymerization to form thin films was simply effected by evaporation of the solvent. The dc electrical conductivity of poly(pyrrole) films formed by this method on glass slides, after rinsing the films with methanol to remove excess phosphomolybdic acid and/or monomer, was on the order of 15–30 S-cm$^{-1}$ for films ranging from 40–100 nm in thickness.

The poly(pyrrole) films produced in this work exhibited excellent electrochemical and optical properties. For example, FIG. 2 shows the cyclic voltammetric behavior of a chemically polymerized poly(pyrrole) film following ten cycles from −1.00 V to +0.70 V vs. SCE. The cathodic wave at −0.40 V corresponded to the reduction of poly(pyrrole) to its neutral, nonconducting state, and the anodic wave at −0.20 V corresponded to the reoxidation of poly(pyrrole) to its conducting state (Kanazawa et al. (1981) *Synth. Met.* 4:119–130). The lack of additional faradaic current, which would result from the oxidation and reduction of phosphomolybdic acid in the film, suggests that the Keggin structure of phosphomolybdic acid was not present in the film anions (Bidan et al. (1988) *J. Electroanal. Chem.* 251:297–306) and implies that $MoO_4^{2-}$, or other anions, served as the poly (pyrrole) counterions in the polymerized films.

FIG. 3A shows the optical spectrum of a processed polypyrrole film that had been spin-coated on glass and then rinsed with methanol. The single absorption maximum was characteristic of a highly oxidized poly(pyrrole) (Kaufman et al. (1984) *Phys. Rev. Lett.* 53:1005–1008), and the absorption band at 4.0 eV was characteristic of an interband transition between the conduction and valence bands. The lack of other bands in this energy range was evidence for the presence of bipolaron states (see FIG. 3A), as have been observed in highly oxidized poly(pyrrole) (Id.). By cycling the film in 0.10 M $[(C_4H_9)_4N]^+[ClO_4]^-$—acetonitrile and then recording the optical spectra in 0.10 M KCl—$H_2O$, it was possible to observe optical transitions characteristic of polaron states in oxidized poly(pyrrole) (see FIG. 3B). The polaron states have been reported to produce three optical transitions (Id.), which were observed at 2.0, 2.9, and 4.1 eV in FIG. 3B. Upon reduction of the film (c.f. FIG. 3B), an increased intensity and a blue shift in the 2.9 eV band was observed, as expected for the $\pi \rightarrow \pi^*$ transition associated with the pyrrole units contained in the polymer backbone (Yakushi et al. (1983) *J. Chem. Phys.* 79:4774–4778).

As described in the experimental section, various plasticizers were introduced into the polymer films (Table 3).

TABLE 3

| Plasticizers used in array elements* | |
|---|---|
| sensor | plasticizer |
| 1 | none |
| 2 | none** |
| 3 | poly(styrene) |
| 4 | poly(styrene) |
| 5 | poly(styrene) |
| 6 | poly(a-methyl styrene) |
| 7 | poly(styrene-acrylonitrile) |
| 8 | poly(styrene-maleic anydride) |
| 9 | poly(styrene-allyl alcohol) |
| 10 | poly(vinyl pyrrolidone) |
| 11 | poly(vinyl phenol) |
| 12 | poly(vinyl butral) |
| 13 | poly(vinyl acetate) |
| 14 | poly(carbonate) |

*Sensors contained 2:3 (w:w) ratio of pyrrole to plasticizer.
**Film not rinsed to remove excess phosphomolybdic acid.

These inclusions allowed chemical control over the binding properties and electrical conductivity of the resulting plasticized polymers. Sensor arrays consisted of as many as 14 different elements, with each element synthesized to produce a distinct chemical composition, and thus a distinct sensor response, for its polymer film. The resistance, R, of each film-coated individual sensor was automatically recorded before, during, and after exposure to various odorants. A typical trial consisted of a 60 sec rest period in which the sensors were exposed to flowing air (3.0 liter-min$^{-1}$), a 60 sec exposure to a mixture of air (3.0 liter-min$^{-1}$) and air that had been saturated with solvent (0.5–3.5 liter-min$^{-1}$), and then a 240 sec exposure to air (3.0 liter-min$^{-1}$).

In an initial processing of the data, presented in this paper, the only information used was the maximum amplitude of the resistance change divided by the initial resistance, $\Delta R_{max}/R_i$, of each individual sensor element. Most of the sensors exhibited either increases or decreases in resistance upon exposure to different vapors, as expected from changes in the polymer properties upon exposure to different types chemicals (Topart and Josowicz (1992) *J. Phys. Chem.* 96:7824–7830; Charlesworth et al. (1993) *J. Phys. Chem.* 97:5418–5423). However, in some cases, sensors displayed an initial decrease followed by an increase in resistance in response to a test odor. Since the resistance of each sensor could increase and/or decrease relative to its initial value, two values of $\Delta R_{max}/R_i$ were reported for each sensor. The source of the bi-directional behavior of some sensor/odor pairs has not yet been studied in detail, but in most cases this behavior arose from the presence of water (which by itself induced rapid decreases in the film resistance) in the reagent-grade solvents used to generate the test odors of this study. The observed behavior in response to these air-exposed, water-containing test solvents was reproducible and reversible on a given sensor array, and the environment was representative of many practical odor sensing applications in which air and water would not be readily excluded.

FIGS. 4B–4D depict representative examples of sensor amplitude responses of a sensor array (see, Table 3). In this experiment, data were recorded for three separate exposures to vapors of acetone, benzene, and ethanol flowing in air. The response patterns generated by the sensor array described in Table 3 are displayed for: (B) acetone; (C) benzene; and (D) ethanol. The sensor response was defined as the maximum percent increase and decrease of the resistance divided by the initial resistance (gray bar and black bar, respectively) of each sensor upon exposure to solvent vapor. In many cases sensors exhibited reproducible increases and decreases in resistance. An exposure consisted of: (i) a 60 sec rest period in which the sensors were exposed to flowing air (3.0 liter-min$^{-1}$); (ii) a 60 sec exposure to a mixture of air (3.0 liter-min$^{-1}$) and air that had been saturated with solvent (0.5 liter-min$^{-1}$); and (iii) a 240 sec exposure to air (3.0 liter-min$^{-1}$). It is readily apparent that these odorants each produced a distinctive response on the sensor array. In additional experiments, a total of 8 separate vapors (acetone, benzene, chloroform, ethanol, isopropyl alcohol, methanol, tetrahydrofuran, and ethyl acetate), chosen to span a range of chemical and physical characteristics, were evaluated over a five-day period on a 14-element sensor array (Table 3). As discussed below, each odorant could be clearly and reproducibly identified from the others using this sensor apparatus.

Principle component analysis (Hecht (1990) *Mathematics in Chemistry: An Introduction to Modern Methods* (Prentice Hall, Englewood Cliffs, N.J.)) was used to simplify presentation of the data and to quantify the distinguishing abilities of individual sensors and of the array as a whole. In this approach, linear combinations of the $\Delta R_{max}/R_i$ data for the elements in the array were constructed such that the maximum variance (defined as the square of the standard deviation) was contained in the fewest mutually orthogonal dimensions. This allowed representation of most of the information contained in data sets shown in FIGS. 4B–4D in two (or three) dimensions. The resulting clustering, or lack thereof, of like exposure data in the new dimensional space was used as a measure of the distinguishing ability, and of the reproducibility, of the sensor array.

In order to illustrate the variation in sensor response of individual sensors that resulted from changes in the plasticizing polymer, principle component analysis was performed on the individual, isolated responses of each of the 14 individual sensor elements in a typical array (FIG. 5). Data were obtained from multiple exposures to acetone (a), benzene (b), chloroform (c), ethanol (e), isopropyl alcohol (i), methanol (m), tetrahydrofuran (t), or ethyl acetate (@) over a period of five days with the test vapors exposed to the array in various sequences. The numbers of the figures refer to the sensor elements described in Table 3. The units along the axes indicate the amplitude of the principle component that was used to describe the particular data set for an odor. The black regions indicate clusters corresponding to a single solvent which could be distinguished from all others; gray regions highlight data of solvents whose signals overlapped with others around it. Exposure conditions were identical to those in FIG. 4.

Since each individual sensor produced two data values, principle component analysis of these responses resulted in only two orthogonal principal components; pc1 and pc2. As an example of the selectivity exhibited by an individual sensor element, the sensor designated as number 5 in FIG. 5 (which was plasticized with poly(styrene)) confused acetone with chloroform, isopropyl alcohol, and tetrahydrofuran. It also confused benzene with ethyl acetate, while easily distinguishing ethanol and methanol from all other solvents. Changing the plasticizer to poly (α-methyl styrene) (sensor number 6 in FIG. 5) had little effect on the spatial distribution of the responses with respect to one another and with respect to the origin. Thus, as expected, a rather slight chemical modification of the plasticizer had little effect on the relative variance of the eight test odorants. In contrast, the addition of a cyano group to the plasticizer, in the form of poly(styrene-acrylonitrile), (sensor number 7 in FIG. 5), resulted in a larger contribution to the overall variance by benzene and chloroform, while decreasing the contribution of ethanol. Changing the substituent group in the plasticizer to a hydrogen bonding acid (poly(styrene-allyl alcohol), sensor number 9 in FIG. 5) increased the contribution of acetone to the overall variance while having little effect on the other odors, with the exception of confusing methanol and ethanol. These results suggest that the behavior of the sensors can be systematically altered by varying the chemical composition of the plasticizing polymer.

FIGS. 6A and 6B show the principle component analysis for all 14 sensors described in Table 3 and FIGS. 4 and 5. When the solvents were projected into a three dimensional odor space (FIG. 6A or 6B), all eight solvents were easily distinguished with the specific array discussed herein. Detection of an individual test odor, based only on the criterion of observing ~1% $\Delta R_{max}/R_i$ values for all elements in the array, was readily accomplished at the parts per thousand level with no control over the temperature or humidity of the flowing air. Further increases in sensitivity are likely after a thorough utilization of the temporal components of the $\Delta R_{max}/R_i$ data as well as a more complete characterization of the noise in the array.

We have also investigated the suitability of this sensor array for identifying the components of certain test mixtures. This task is greatly simplified if the array exhibits a predictable signal response as the concentration of a given odorant is varied, and if the responses of various individual odors are additive (i.e., if superposition is maintained).

When a 19-element sensor array was exposed to a number, n, of different acetone concentrations in air, the $(CH_3)_2CO$ concentration was semi-quantitavely predicted from the first principle component. This was evident from a good linear least square fit through the first three principle components (see FIG. 7A for the linear least square fit for the first principle component).

The same sensor array was also able to resolve the components in various test methanol-ethanol mixtures (Morris et al. (1942) *Can. J. Res. B* 20:207–211. As shown in FIG. 7B, a linear relationship was observed between the first principle component and the mole fraction of methanol in the liquid phase, $x_m$, in a $CH_3OH$—$C_2H_5OH$ mixture, demonstrating that superposition held for this mixture/sensor array combination. Furthermore, although the components in the mixture could be predicted fairly accurately from just the first principle component, an increase in the accuracy could be achieved using a multi-linear least square fit through the first three principle components. This relationship held for $CH_3OH/(CH_3OH+C_2H_5OH)$ ratios of 0 to 1.0 in air-saturated solutions of this vapor mixture. The conducting polymer-based sensor arrays could therefore not only distinguish between pure test vapors, but also allowed analysis of concentrations of odorants as well as analysis of binary mixtures of vapors.

In summary, the results presented herein advance the area of analyte sensor design. A relatively simple array design, using only a multiplexed low-power dc electrical resistance readout signal, has been shown to readily distinguish between various test odorants. Such conducting polymer-based arrays are simple to construct and modify, and afford an opportunity to effect chemical control over the response pattern of a vapor. For example, by increasing the ratio of plasticizer to conducting polymer, it is possible to approach the percolation threshold, at which point the conductivity exhibits a very sensitive response to the presence of the sorbed molecules. Furthermore, producing thinner films will afford the opportunity to obtain decreased response times, and increasing the number of plasticizing polymers and polymer backbone motifs will likely result in increased diversity among sensors. This type of polymer-based array is chemically flexible, is simple to fabricate, modify, and analyze, and utilizes a low power dc resistance readout signal transduction path to convert chemical data into electrical signals. It provides a new approach to broadly-responsive odor sensors for fundamental and applied investigations of chemical mimics for the mammalian sense of smell. Such systems are useful for evaluating the generality of neural network algorithms developed to understand how the mammalian olfactory system identifies the directionality, concentration, and identity of various odors.

Fabrication and Testing of Carbon Black-based Sensor Arrays, Sensor Fabrication

Individual sensor elements were fabricated in the following manner. Each non-conductive polymer (80 mg, see Table 4) was dissolved in 6 ml of THF.

TABLE 4

| Sensor # | Non-Conductive Polymer |
| --- | --- |
| 1 | poly(4-vinyl phenol) |
| 2 | poly(styrene - allyl alcohol) |
| 3 | poly(α-methyl styrene) |
| 4 | poly(vinyl chloride - vinyl acetate) |
| 5 | poly(vinyl acetate) |

TABLE 4-continued

| Sensor # | Non-Conductive Polymer |
| --- | --- |
| 6 | poly(N-vinyl pyrrolidone) |
| 7 | poly(bisphenol A carbonate) |
| 8 | poly(styrene) |
| 9 | poly(styrene-maleic anhydride) |
| 10 | poly(sulfone) |

Then, 20 mg of carbon black (BP 2000, Cabot Corp.) were suspended with vigorous mixing. Interdigitated electrodes (the cleaved capacitors previously described) were then dipped into this mixture and the solvent allowed to evaporate. A series of such sensor elements with differing non-conductive polymers were fabricated and incorporated into a commercial bus strip which allowed the chemiresistors to be easily monitored with a multiplexing ohmmeter.

Sensor Array Testing

To evaluate the performance of the carbon-black based sensors, arrays with as many as 20 elements were exposed to a series of analytes. A sensor exposure consisted of (1) a 60 second exposure to flowing air (6 liter min-1), (2) a 60 second exposure to a mixture of air (6 liter min-1) and air that had been saturated with the analyte (0.5 liter min-1), (3) a five minute recovery period during which the sensor array was exposed to flowing air (6 liter min-1). The resistance of the elements were monitored during exposure, and depending on the thickness and chemical make-up of the film, resistance changes as large as 250% could be observed in response to an analyte. In one experiment, a 10 element sensor array consisting carbon-black composites formed with a series of non-conductive polymers (see Table 4) was exposed to acetone, benzene, chloroform, ethanol, hexane, methanol, and toluene over a two day period. A total of 58 exposures to these analytes were performed in this time period. In all cases, resistance changes in response to the analytes were positive, and with the exception of acetone, reversible (see FIG. 8). The maximum positive deviations were then subjected to principal component analysis in a manner analogous to that described for the poly(pyrrole) based sensor. FIG. 9 shows the results of the principal component analysis for the entire 10-element array. With the exception of overlap between toluene with benzene, the analytes were distinguished from one and other.

II. Temperature Variance (Experiment 1)

Sensor Fabrication

Into 15 ml of benzene, was dissolved 160 mg of polymer (either poly(styrene) and poly(ethylene-co-vinyl acetate) and to this was added 40 mg of carbon black forming a suspension. The sensor substrate was a 10 mm by 25 mm glass slide onto which had been evaporated two gold pads approximately 1000 angstroms thick. These gold pads entirely covered one face of the slide with the exception of a 5 mm wide section across the middle of one face of the slide. The glass slide was rapidly dipped into the polymer suspension of carbon black 5–10 times to coat the slide with the polymer composite. The face opposite the gold pads was wiped clean of deposits.

The heating element was made from 24 gauge nickel chromium wire which was bent into a zig-zag shape with each turn being equal in length to the width of the sensor element. Wire tails were allowed to extend about 1 cm from opposite sides of the sensors for external electrical connections. The total length of the heating elements was approximately 7 cm. The heating element was attached to the back (the face opposite the gold pads) with epoxy (able to withstand 120° C.) by sandwiching it between the sensor and another (uncoated) glass slide of the same size as the sensor. The final sensor configuration was allowed to stand 5–10 days before use. The heating elements were heated by passing 0.8, 1.2 or 1.6 A of current through the elements.

Data Collection

Each sensor was placed in the flow chamber individually, with all electrical connections in place, and allowed to equilibrate to the background air flow until a stable baseline was achieved. Each exposure consisted of talking data for 60 seconds to establish a baseline, followed by a 60 second exposure to the analyte vapor stream and finally followed by a five minute recovery period before the next cycle began. For both sensors, data were collected for exposures to chloroform and benzene at four different temperatures for each solvent. First, data were collected for analyte exposure while at ambient temperature (about 22° C.; i.e., "temperature 1"), followed by the temperature associated with passing 0.8 A of electrical current through the heating element ("temperature 2"), then 1.2 A ("temperature 3") and then 1.6 A of current ("temperature 4") (the latter temperatures being undetermined). The sensors were allowed to equilibrate at each new temperature for 15 minutes before data collection was initiated. Three exposures at each current were taken.

Data Analysis

The data streams were saved to the computer during the exposures to the analyte. Baseline resistances were taken by averaging the resistance data during the 20 seconds prior to exposure to the analyte. The maximum resistance was extracted from the data stream and the change in resistance between baseline and maximum resistance was calculated ($\Delta R$). This $\Delta R$ value was divided by the baseline resistance (R) and multiplied by 100 to express the response as a percentage. The percent responses for the three exposures at each temperature were averaged to obtain one value for each temperature/solvent combination. The responses for each vapor at the four temperatures tested were normalized by summing the four values and dividing each response by this sum. The results of these experiments are presented in Table 5.

TABLE 5

| Polymer composition/analyte | ($\Delta R/R$) × 100 | Normalized |
| --- | --- | --- |
| A. Poly(styrene)/Chloroform | | |
| temperature 1 | 0.60770905 | 0.23762355 |
| temperature 2 | 0.69325945 | 0.27107507 |
| temperature 3 | 0.75494462 | 0.29519491 |
| temperature 4 | 0.50153141 | 0.19610647 |
| Sum | 2.55744454 | |
| B. Poly(styrene)/Benzene | | |
| temperature 1 | 0.33986648 | 0.38334474 |
| temperature 2 | 0.23028222 | 0.25974165 |
| temperature 3 | 0.14179893 | 0.15993891 |
| temperature 4 | 0.17463419 | 0.1969747 |
| Sum | 0.88658181 | |
| C. Poly(ethylene-co-vinyl acetate)/Chloroform | | |
| temperature 1 | 33.5395398 | 0.63563285 |
| temperature 2 | 12.1030896 | 0.22937468 |
| temperature 3 | 5.71049748 | 0.1082239 |
| temperature 4 | 1.41245945 | 0.02676857 |
| Sum | 52.7655863 | |
| D. Poly(ethylene-co-vinyl acetate)/Benzene | | |
| temperature 1 | 10.236522 | 0.54522797 |

TABLE 5-continued

| Polymer composition/analyte | ($\Delta R/R$) × 100 | Normalized |
| --- | --- | --- |
| temperature 2 | 5.66926122 | 0.30196192 |
| temperature 3 | 2.37495836 | 0.12649743 |
| temperature 4 | 0.49401403 | 0.02631267 |
| Sum | 18.7747556 | |

The results in Table 5 demonstrate that both the poly (styrene) and poly(ethylene-co-vinyl acetate) sensors provided different electrical resistances at different temperatures with the two analytes tested. Moreover, the results presented in Table 5 demonstrate that different analytes provide different, unique patterns of electrical resistance at the various temperatures tested. Therefore, these data demonstrate that by varying the temperature at which the electrical resistance readings are obtained from the sensor element, one is able to identify a unique pattern of electrical resistances for any analyte of interest, thereby allowing for the identification of an analyte of interest.

III. Temperature Variance (Experiment 2)

Three sensor composites were used. These were poly (ethylene-co-vinyl acetate), poly(ethylene oxide), and poly (4-vinyl phenol). These composites were blended with conductive carbon black in a 1:4 carbon black to polymer ratio. The composite material was coated onto a glass slide which had evaporated gold tabs as electrical contacts. To the underside of the glass slide (the side without the polymer film) was affixed nickel-chromium heating wire using low vapor pressure/high temperature epoxy. The wire was bent into a zig zag shape and affixed so that the main heating area was directly opposite the region between the gold tabs. Next was attached the underside of the heating wire a plain (not coated with gold or polymer) glass slide of the same dimension as the substrate slide. In this configuration the heating wire was sandwiched between two glass slides. A thin thermocouple was glued to the second glass slide on the opposite side from the heating wire. Therefore, the temperature detection was made at a similar orientation to the heater as the polymer composite film. (See FIG. 10).

The current for the resistive heaters was supplied by one common power supply. The resistive heaters were wired in parallel with the power supply. There was a rheostat (variable resistor) in series with each branch of the parallel circuit. This way the amount of current to each heater, and subsequently its temperature, could be controlled. The temperatures were measured by the attached thermocouples. These temperatures were not monitored continuously, but were recorded before an experiment began and at selected times during the experiment. Once equilibrium was reached, the temperature of the sensor/heater did not deviate more than 0.1° C. over the course of minutes and did not deviate more than 1° C. over the course of each experiment (about 3 hours).

Multiple copies of each sensor/heater were made and placed into a flow chamber. For poly(ethylene oxide), five sensors were made; sensors 4, 6, 9, 15, and 16. Sensors 15 and 16 were heated, with sensor 15 being set to higher temperatures. Sensors 4, 6, and 9 were not heated. For poly(ethylene-co-vinyl acetate), four sensors were made; sensors 3, 8, 17, and 20. Sensors 17 and 20 were heated, with sensor 17 being set to higher temperatures. Sensors 3 and 8 were not heated. For poly(4-vinyl phenol), four sensors were made; sensors 5, 7, 18, and 19. Sensors 18 and 19 were heated, with sensor 18 being set to higher temperatures. Sensors 5 and 7 were not heated.

In these experiments, exposures were made to eight different solvents: benzene, chloroform, toluene, cyclohexane, hexane, 2-propanol, ethanol, and methanol. Each solvent was exposed at a concentration of 900 ppm. In every experiment, the solvents were exposed to the sensors three times in the order listed above. The average of these three trials was taken and the standard deviation calculated.

Six experiments were performed. First, all the sensors were kept at room temperature during the exposures. Second, the heated sensors were heated to the first set of temperature values, TEMP1. (The specific temperature values are listed in Tables 6 and 7 below.) This was followed by another exposure set where all the sensors were at room temperature. Fourth, the second temperature experiment was repeated, TEMP2. The temperatures of TEMP1 and of TEMP2 were meant to be nominally the same values (see data tables below). The fifth experiment was another set of room temperature exposures. Finally, another heated exposure set, TEMP3, was collected.

The temperatures of the sensors in TEMP3 were adjusted to be higher than those in TEMP1 or TEMP2.

The average resistance and the standard deviations for the three trials in each experiment were calculated and are listed in Table 6. Since the over-all signal for each sensor decreases at higher temperatures, the average responses and the standard deviation for each sensor were normalized and are listed in Table 7. The first, second, and third columns of the tables are the three room temperature experiments. The last three columns are TEMP1, TEMP2, and TEMP3, respectively. The values in Tables 6 and 7 are also presented graphically in FIGS. 11 and 12.

TABLE 6

|  | Exp 1 | Exp 3 | Exp 5 | Exp 2 | Exp 4 | Exp 6 |
| --- | --- | --- | --- | --- | --- | --- |
|  | 22° C. | 22° C. | 23° C. | 22° C. | 22° C. | 22° C. |
| AVERAGES Sensor 3 poly(ethylene-vinyl acetate) (not heated) | | | | | | |
| 2-propanol | 1.81E−03 | 1.75E−03 | 1.91E−03 | 1.84E−03 | 1.94E−03 | 1.84E−03 |
| benzene | 6.25E−03 | 6.07E−03 | 6.52E−03 | 6.54E−03 | 6.49E−03 | 6.19E−03 |
| chloroform | 5.67E−03 | 5.36E−03 | 5.92E−03 | 5.96E−03 | 5.81E−03 | 5.57E−03 |
| cyclohexane | 5.08E−03 | 4.89E−03 | 5.35E−03 | 5.17E−03 | 5.27E−03 | 5.06E−03 |
| ethanol | 1.33E−03 | 1.31E−03 | 1.40E−03 | 1.40E−03 | 1.39E−03 | 1.33E−03 |
| hexane | 2.95E−03 | 2.67E−03 | 2.90E−03 | 3.04E−03 | 2.93E−03 | 2.75E−03 |
| methanol | 3.31E−04 | 3.21E−04 | 3.53E−04 | 4.27E−04 | 3.76E−04 | 3.24E−04 |
| toluene | 2.59E−02 | 2.51E−02 | 2.69E−02 | 2.63E−02 | 2.68E−02 | 2.50E−02 |
| STANDARD DEVIATION Sensor 3 poly(ethylene-vinyl acetate) (not heated) | | | | | | |
| 2-propanol | 1.31E−04 | 3.54E−05 | 1.73E−05 | 1.15E−04 | 4.06E−05 | 1.32E−04 |
| benzene | 2.10E−04 | 1.09E−04 | 7.78E−05 | 1.07E−04 | 5.47E−05 | 2.40E−04 |
| chloroform | 2.68E−04 | 1.92E−04 | 1.08E−04 | 6.68E−05 | 1.54E−04 | 4.12E−04 |
| cyclohexane | 3.40E−04 | 8.72E−05 | 3.93E−05 | 6.75E−05 | 1.04E−04 | 1.27E−04 |
| ethanol | 1.04E−04 | 4.64E−06 | 4.02E−05 | 4.93E−05 | 6.15E−06 | 9.95E−05 |
| hexane | 7.78E−05 | 9.45E−05 | 9.02E−05 | 1.65E−04 | 4.74E−05 | 1.27E−04 |
| methanol | 4.35E−05 | 8.52E−06 | 3.66E−05 | 1.13E−04 | 2.92E−05 | 7.60E−05 |
| toluene | 7.89E−04 | 1.09E−04 | 1.97E−04 | 2.95E−04 | 7.18E−05 | 6.94E−04 |
|  | 22° C. | 22° C. | 23° C. | 22° C. | 22° C. | 22° C. |
| AVERAGES Sensor 8 poly(ethylene-vinyl acetate) (not heated) | | | | | | |
| 2-propanol | 1.98E−03 | 1.99E−03 | 2.09E−03 | 1.99E−03 | 2.15E−03 | 2.07E−03 |
| benzene | 6.30E−03 | 6.29E−03 | 6.64E−03 | 6.54E−03 | 6.65E−03 | 6.40E−03 |
| chloroform | 5.77E−03 | 5.68E−03 | 6.07E−03 | 6.05E−03 | 6.06E−03 | 5.89E−03 |
| cyclohexane | 5.09E−03 | 4.98E−03 | 5.33E−03 | 5.20E−03 | 5.29E−03 | 5.10E−03 |
| ethanol | 1.46E−03 | 1.48E−03 | 1.52E−03 | 1.51E−03 | 1.54E−03 | 1.51E−03 |
| hexane | 2.89E−03 | 2.71E−03 | 2.92E−03 | 3.01E−03 | 2.93E−03 | 2.76E−03 |
| methanol | 4.09E−04 | 3.81E−04 | 4.24E−04 | 4.08E−04 | 4.39E−04 | 4.05E−04 |
| toluene | 2.60E−02 | 2.59E−02 | 2.70E−02 | 2.63E−02 | 2.74E−02 | 2.59E−02 |
| STANDARD DEVIATION Sensor 8 poly(ethylene-vinyl acetate) (not heated) | | | | | | |
| 2-propanol | 1.51E−04 | 2.74E−05 | 1.64E−05 | 1.01E−04 | 2.63E−05 | 1.54E−04 |
| benzene | 2.16E−04 | 8.58E−05 | 1.10E−04 | 1.35E−05 | 4.36E−05 | 3.07E−04 |
| chloroform | 3.16E−04 | 1.85E−04 | 1.32E−04 | 1.25E−04 | 2.21E−04 | 4.06E−04 |
| cyclohexane | 2.92E−04 | 5.74E−05 | 6.15E−05 | 6.35E−05 | 1.42E−04 | 1.59E−04 |
| ethanol | 1.06E−04 | 5.89E−06 | 2.59E−05 | 7.20E−05 | 1.26E−05 | 1.16E−04 |
| hexane | 1.22E−05 | 1.35E−04 | 9.43E−05 | 7.96E−05 | 6.86E−05 | 1.18E−04 |
| methanol | 5.87E−05 | 3.07E−05 | 4.54E−05 | 5.25E−05 | 4.22E−05 | 8.63E−05 |
| toluene | 8.10E−04 | 1.75E−04 | 2.71E−04 | 2.82E−04 | 1.08E−04 | 7.10E−04 |
|  | 22° C. | 22° C. | 23° C. | 45° C. | 46° C. | 55° C. |
| AVERAGES Sensor 17 poly(ethylene-vinyl acetate) | | | | | | |
| 2-propanol | 2.21E−03 | 2.41E−03 | 2.44E−03 | 2.98E−04 | 7.14E−04 | 2.53E−04 |
| benzene | 6.90E−03 | 7.49E−03 | 7.72E−03 | 1.21E−03 | 1.73E−03 | 7.61E−04 |
| chloroform | 6.49E−03 | 6.83E−03 | 7.07E−03 | 1.59E−03 | 1.77E−03 | 6.25E−04 |
| cyclohexane | 5.80E−03 | 6.20E−03 | 6.41E−03 | 1.97E−03 | 2.32E−03 | 9.23E−04 |

TABLE 6-continued

|  | Exp 1 | Exp 3 | Exp 5 | Exp 2 | Exp 4 | Exp 6 |
|---|---|---|---|---|---|---|
| ethanol | 1.54E-03 | 1.74E-03 | 1.72E-03 | 3.31E-03 | 5.19E-04 | 1.75E-04 |
| hexane | 3.33E-03 | 3.34E-03 | 3.46E-03 | 1.29E-03 | 1.18E-03 | 7.20E-04 |
| methanol | 4.19E-04 | 4.45E-04 | 4.55E-04 | 3.68E-05 | 5.55E-04 | 8.80E-05 |
| toluene | 2.72E-02 | 2.93E-02 | 2.98E-02 | 7.81E-03 | 6.29E-03 | 3.63E-03 |
| STANDARD DEVIATION Sensor 17 poly(ethylene-vinyl acetate) | | | | | | |
| 2-propanol | 1.90E-04 | 6.46E-05 | 2.05E-05 | 4.27E-04 | 2.19E-04 | 1.36E-04 |
| benzene | 3.13E-04 | 1.13E-04 | 1.38E-04 | 1.30E-03 | 4.55E-04 | 1.51E-04 |
| chloroform | 3.89E-04 | 2.87E-04 | 1.57E-04 | 1.75E-04 | 1.92E-04 | 1.77E-04 |
| cyclohexane | 4.04E-04 | 1.79E-04 | 8.12E-05 | 3.61E-06 | 3.20E-04 | 1.51E-04 |
| ethanol | 1.32E-04 | 4.09E-05 | 3.1IE-05 | 1.22E-04 | 1.08E-04 | 1.11E-04 |
| hexane | 8.52E-05 | 1.86E-04 | 9.90E-05 | 2.44E-04 | 1.37E-05 | 3.93E-04 |
| methanol | 5.97E-05 | 3.50E-05 | 5.45E-05 | 9.24E-05 | 8.97E-05 | 1.46E-04 |
| toluene | 9.38E-04 | 3.33E-04 | 3.38E-04 | 3.07E-03 | 2.14E-04 | 2.95E-03 |
|  | 22° C. | 22° C. | 23° C. | 33° C. | 34° C. | 37° C. |
| AVERAGES Sensor 20 poly(ethylene-vinyl acetate) | | | | | | |
| 2-propanol | 3.83E-03 | 3.75E-03 | 3.91E-03 | 2.56E-03 | 2.89E-03 | 2.30E-03 |
| benzene | 1.09E-02 | 1.09E-02 | 1.12E-02 | 8.36E-03 | 8.20E-03 | 6.82E-03 |
| chloroform | 1.06E-02 | 1.02E-02 | 1.07E-02 | 7.63E-03 | 7.61E-03 | 5.87E-03 |
| cyclohexane | 9.50E-03 | 9.22E-03 | 9.63E-03 | 7.39E-03 | 7.52E-03 | 6.08E-03 |
| ethanol | 2.75E-03 | 2.82E-03 | 2.77E-03 | 2.00E-03 | 2.43E-03 | 1.82E-03 |
| hexane | 5.39E-03 | 4.93E-03 | 5.20E-03 | 4.20E-03 | 4.34E-03 | 3.13E-03 |
| methanol | 8.33E-04 | 7.91E-04 | 8.08E-04 | 6.09E-04 | 9.35E-04 | 5.63E-04 |
| toluene | 4.49E-02 | 4.37E-02 | 4.56E-02 | 3.01E-02 | 3.14E-02 | 2.35E-02 |
| STANDARD DEVIATION Sensor 20 poly(ethylene-vinyl acetate) | | | | | | |
| 2-propanol | 2.89E-04 | 6.98E-05 | 3.96E-05 | 2.04E-04 | 1.50E-04 | 5.24E-04 |
| benzene | 4.76E-04 | 1.63E-04 | 2.44E-04 | 6.45E-04 | 4.10E-04 | 5.20E-04 |
| chloroform | 6.01E-04 | 3.53E-04 | 2.61E-04 | 2.21E-04 | 3.29E-04 | 4.52E-04 |
| cyclohexane | 6.43E-04 | 1.88E-04 | 1.46E-04 | 3.20E-04 | 8.44E-05 | 6.69E-04 |
| ethanol | 2.17E-04 | 1.31E-05 | 5.29E-05 | 9.05E-05 | 3.28E-04 | 3.89E-04 |
| hexane | 1.71E-04 | 2.28E-04 | 1.38E-04 | 1.31E-04 | 1.42E-04 | 3.19E-04 |
| methanol | 5.76E-05 | 5.00E-05 | 2.52E-05 | 9.05E-05 | 9.12E-04 | 3.11E-04 |
| toluene | 1.75E-03 | 3.75E-04 | 5.35E-04 | 1.71E-03 | 5.16E-04 | 9.34E-04 |
|  | 22° C. | 22° C. | 23° C. | 22° C. | 22° C. | 22° C. |
| AVERAGES Sensor 4 poly(ethylene oxide) (not heated) | | | | | | |
| 2-propanol | 3.34E-03 | 3.16E-03 | 3.34E-03 | 3.33E-03 | 3.28E-03 | 3.16E-03 |
| benzene | 8.18E-03 | 7.34E-03 | 8.06E-03 | 8.25E-03 | 7.86E-03 | 7.26E-03 |
| chloroform | 7.83E-03 | 7.17E-03 | 7.73E-03 | 8.01E-03 | 7.56E-03 | 7.20E-03 |
| cyclohexane | 9.32E-04 | 8.13E-04 | 9.19E-04 | 9.16E-04 | 8.74E-04 | 8.17E-04 |
| ethanol | 3.12E-03 | 2.94E-03 | 3.12E-03 | 3.09E-03 | 3.05E-03 | 2.90E-03 |
| hexane | 7.00E-04 | 5.70E-04 | 6.80E-04 | 6.86E-04 | 6.47E-04 | 6.05E-04 |
| methanol | 1.48E-03 | 1.38E-03 | 1.48E-03 | 1.47E-03 | 1.44E-03 | 1.39E-03 |
| toluene | 2.96E-02 | 2.65E-02 | 2.88E-02 | 2.93E-02 | 2.83E-02 | 2.62E-02 |
| STANDARD DEVIATION Sensor 4 poly(ethylene oxide) (not heated) | | | | | | |
| 2-propanol | 1.26E-04 | 6.19E-05 | 3.44E-05 | 1.13E-05 | 6.71E-06 | 1.12E-04 |
| benzene | 2.33E-04 | 2.30E-04 | 7.16E-05 | 1.07E-05 | 6.90E-05 | 1.74E-04 |
| chloroform | 3.43E-04 | 3.64E-04 | 1.47E-04 | 1.26E-04 | 2.29E-04 | 2.85E-04 |
| cyclohexane | 1.72E-05 | 5.23E-05 | 1.83E-07 | 8.32E-06 | 1.81E-05 | 1.76E-05 |
| ethanol | 1.40E-04 | 1.37E-04 | 2.17E-05 | 2.32E-05 | 2.82E-05 | 1.33E-04 |
| hexane | 1.37E-05 | 6.93E-05 | 3.62E-06 | 3.07E-06 | 1.41E-05 | 2.07E-05 |
| methanol | 2.24E-05 | 2.22E-05 | 2.51E-05 | 2.03E-05 | 1.21E-05 | 4.49E-05 |
| toluene | 4.39E-04 | 1.17E-04 | 1.75E-04 | 2.24E-04 | 8.57E-05 | 3.94E-04 |
|  | 22° C. | 22° C. | 23° C. | 22° C. | 22° C. | 22° C. |
| AVERAGES Sensor 6 poly(ethylene oxide) (not heated) | | | | | | |
| 2-propanol | 3.30E-03 | 3.08E-03 | 3.29E-03 | 3.27E-03 | 3.21E-03 | 3.11E-03 |
| benzene | 9.14E-03 | 7.90E-03 | 8.92E-03 | 9.15E-03 | 8.61E-03 | 8.01E-03 |
| chlorofonm | 8.33E-03 | 7.45E-03 | 8.19E-03 | 8.42E-03 | 7.90E-03 | 7.58E-03 |
| cyclohexane | 1.05E-03 | 8.60E-04 | 1.02E-03 | 1.01E-03 | 9.59E-04 | 9.11E-04 |
| ethanol | 2.97E-03 | 2.78E-03 | 2.97E-03 | 2.94E-03 | 2.90E-03 | 2.78E-03 |
| hexane | 8.32E-04 | 6.13E-04 | 7.86E-04 | 7.95E-04 | 7.27E-04 | 7.00E-04 |
| methanol | 1.41E-03 | 1.29E-03 | 1.41E-03 | 1.40E-03 | 1.36E-03 | 1.32E-03 |
| toluene | 3.26E-02 | 2.86E-02 | 3.16E-02 | 3.21E-02 | 3.08E-02 | 2.86E-02 |
| STANDARD DEVIATION Sensor 6 poly(ethylene oxide) (not heated) | | | | | | |
| 2-propanol | 1.41E-04 | 9.26E-05 | 3.57E-05 | 2.04E-05 | 1.50E-05 | 1.28E-04 |

TABLE 6-continued

|  | Exp 1 | Exp 3 | Exp 5 | Exp 2 | Exp 4 | Exp 6 |
|---|---|---|---|---|---|---|
| benzene | 2.67E−04 | 4.58E−04 | 7.88E−05 | 1.53E−05 | 9.19E−05 | 2.07E−04 |
| chloroform | 3.71E−04 | 4.83E−04 | 1.55E−04 | 1.30E−04 | 2.75E−04 | 3.12E−04 |
| cyclohexane | 2.33E−05 | 9.05E−05 | 7.15E−06 | 1.49E−05 | 2.55E−05 | 2.30E−05 |
| ethanol | 1.33E−04 | 4.14E−05 | 2.35E−05 | 1.28E−05 | 1.62E−05 | 1.31E−04 |
| hexane | 5.79E−06 | 1.20E−04 | 8.29E−06 | 6.28E−06 | 1.99E−05 | 1.83E−05 |
| methanol | 2.66E−05 | 3.85E−05 | 2.54E−05 | 1.50E−05 | 1.27E−05 | 5.24E−05 |
| toluene | 4.69E−04 | 4.37E−04 | 1.57E−04 | 2.68E−04 | 1.32E−04 | 4.26E−04 |
|  | 22° C. | 22° C. | 23° C. | 22° C. | 22° C. | 22° C. |

AVERAGES Sensor 9 poly(ethylene oxide) (not heated)

|  | Exp 1 | Exp 3 | Exp 5 | Exp 2 | Exp 4 | Exp 6 |
|---|---|---|---|---|---|---|
| 2-propanol | 3.22E−03 | 3.50E−03 | 3.30E−03 | 3.27E−03 | 3.17E−03 | 3.44E−03 |
| benzene | 6.27E−03 | 5.77E−03 | 6.10E−03 | 6.32E−03 | 5.80E−03 | 5.19E−03 |
| chloroform | 6.60E−03 | 6.27E−03 | 6.51E−03 | 6.78E−03 | 6.37E−03 | 5.95E−03 |
| cyclohexane | 7.82E−04 | 9.06E−04 | 7.59E−04 | 7.55E−04 | 7.16E−04 | 6.71E−04 |
| ethanol | 3.03E−03 | 3.22E−03 | 2.98E−03 | 2.96E−03 | 2.99E−03 | 3.02E−03 |
| hexane | 5.46E−04 | 8.12E−04 | 5.37E−04 | 5.84E−04 | 5.11E−04 | 5.61E−04 |
| methanol | 1.50E−03 | 1.75E−03 | 1.45E−03 | 1.51E−03 | 1.55E−03 | 1.63E−03 |
| toluene | 2.20E−02 | 1.84E−02 | 2.11E−02 | 2.18E−02 | 1.99E−02 | 1.72E−02 |

STANDARD DEVIATION Sensor 9 poly(ethylene oxide) (not heated)

|  | Exp 1 | Exp 3 | Exp 5 | Exp 2 | Exp 4 | Exp 6 |
|---|---|---|---|---|---|---|
| 2-propanol | 1.61E−04 | 1.51E−04 | 7.00E−05 | 2.98E−05 | 1.16E−04 | 3.78E−04 |
| benzene | 2.27E−04 | 4.88E−04 | 1.35E−04 | 1.08E−04 | 4.08E−05 | 9.07E−05 |
| chloroform | 2.06E−04 | 1.36E−04 | 5.63E−05 | 6.31E−05 | 1.40E−04 | 4.07E−04 |
| cyclohexane | 5.07E−05 | 1.66E−04 | 3.37E−05 | 9.69E−05 | 9.88E−06 | 3.78E−05 |
| ethanol | 1.73E−04 | 2.07E−04 | 1.65E−05 | 6.02E−05 | 1.96E−04 | 1.85E−04 |
| hexane | 8.37E−05 | 2.83E−04 | 4.77E−05 | 4.83E−05 | 1.68E−04 | 1.64E−04 |
| methanol | 7.56E−05 | 1.00E−04 | 2.88E−05 | 5.50E−05 | 8.35E−05 | 1.31E−04 |
| toluene | 4.26E−04 | 3.61E−04 | 8.15E−05 | 2.75E−04 | 4.39E−04 | 3.32E−04 |
|  | 22° C. | 22° C. | 23° C. | 44° C. | 47° C. | 57° C. |

AVERAGES Sensor 15 poly(ethylene oxide)

|  | Exp 1 | Exp 3 | Exp 5 | Exp 2 | Exp 4 | Exp 6 |
|---|---|---|---|---|---|---|
| 2-propanol | 2.77E−03 | 2.98E−03 | 2.72E−03 | 7.13E−04 | 9.59E−04 | 3.19E−04 |
| benzene | 2.84E−03 | 3.10E−03 | 2.68E−03 | 9.04E−04 | 1.20E−03 | 3.39E−04 |
| chloroform | 3.58E−03 | 3.69E−03 | 3.36E−03 | 1.08E−03 | 1.24E−03 | 3.68E−04 |
| cyclohexane | 5.61E−04 | 8.60E−04 | 5.55E−04 | 1.34E−04 | 3.74E−04 | 1.79E−04 |
| ethanol | 2.57E−03 | 2.79E−03 | 2.47E−03 | 7.74E−04 | 7.59E−04 | 3.65E−04 |
| hexane | 4.32E−04 | 6.88E−04 | 4.27E−04 | 2.39E−04 | 2.71E−04 | 7.47E−05 |
| methanol | 1.30E−03 | 1.56E−03 | 1.27E−03 | 4.09E−04 | 4.07E−04 | 2.53E−04 |
| toluene | 9.45E−03 | 8.67E−03 | 8.77E−03 | 3.66E−03 | 3.18E−03 | 1.29E−03 |

STANDARD DEVIATION Sensor 15 poly(ethylene oxide)

|  | Exp 1 | Exp 3 | Exp 5 | Exp 2 | Exp 4 | Exp 6 |
|---|---|---|---|---|---|---|
| 2-propanol | 7.33E−05 | 3.50E−05 | 3.75E−05 | 2.57E−04 | 6.46E−05 | 9.75E−05 |
| benzene | 2.31E−05 | 4.43E−04 | 5.95E−05 | 3.78E−04 | 1.52E−04 | 2.56E−04 |
| chloroform | 1.11E−04 | 1.88E−04 | 2.75E−05 | 1.65E−04 | 9.19E−05 | 1.11E−04 |
| cyclohexane | 2.69E−05 | 1.20E−04 | 1.32E−04 | 4.88E−05 | 1.96E−04 | 2.41E−04 |
| ethanol | 8.53E−05 | 1.61E−04 | 1.35E−04 | 8.05E−05 | 9.10E−05 | 2.14E−04 |
| hexane | 8.14E−05 | 9.59E−05 | 1.24E−05 | 2.91E−04 | 1.21E−04 | 3.69E−05 |
| methanol | 7.68E−05 | 3.61E−05 | 1.24E−04 | 7.45E−05 | 1.30E−04 | 1.33E−04 |
| toluene | 1.23E−04 | 3.63E−04 | 9.63E−05 | 7.71E−05 | 1.43E−04 | 2.46E−04 |
|  | 22° C. | 22° C. | 23° C. | 33° C. | 33° C. | 37° C. |

AVERAGES Sensor 16 poly(ethylene oxide)

|  | Exp 1 | Exp 3 | Exp 5 | Exp 2 | Exp 4 | Exp 6 |
|---|---|---|---|---|---|---|
| 2-propanol | 3.02E−03 | 3.03E−03 | 2.96E−03 | 1.84E−03 | 1.81E−03 | 1.35E−03 |
| benzene | 6.36E−03 | 5.48E−03 | 5.99E−03 | 4.56E−03 | 4.14E−03 | 2.95E−03 |
| chloroform | 6.49E−03 | 5.86E−03 | 6.18E−03 | 4.20E−03 | 3.87E−03 | 2.77E−03 |
| cyclohexane | 6.70E−04 | 6.68E−04 | 6.34E−04 | 5.19E−04 | 4.89E−04 | 4.13E−04 |
| ethanol | 2.74E−03 | 2.81E−03 | 2.68E−03 | 1.71E−03 | 1.66E−03 | 1.28E−03 |
| hexane | 4.22E−04 | 5.13E−04 | 4.37E−04 | 3.48E−04 | 3.53E−04 | 3.02E−04 |
| methanol | 1.32E−03 | 1.42E−03 | 1.27E−03 | 8.77E−04 | 8.50E−04 | 7.23E−04 |
| toluene | 2.28E−02 | 1.87E−02 | 2.08E−02 | 1.61E−02 | 1.43E−02 | 1.03E−02 |

STANDARD DEVIATION Sensor 16 poly(ethylene oxide)

|  | Exp 1 | Exp 3 | Exp 5 | Exp 2 | Exp 4 | Exp 6 |
|---|---|---|---|---|---|---|
| 2-propanol | 1.18E−04 | 7.87E−05 | 2.67E−05 | 4.18E−05 | 2.22E−05 | 4.92E−05 |
| bentene | 2.12E−04 | 1.65E−04 | 4.59E−05 | 3.95E−05 | 6.30E−05 | 1.12E−04 |
| chloroform | 3.17E−04 | 8.02E−05 | 1.20E−04 | 4.67E−05 | 6.31E−05 | 1.40E−04 |
| cyclohexane | 7.01E−06 | 7.16E−05 | 8.73E−06 | 4.19E−05 | 4.15E−05 | 1.80E−05 |
| ethanol | 1.27E−04 | 1.07E−04 | 1.53E−05 | 2.90E−05 | 1.12E−05 | 4.05E−05 |
| hexane | 2.13E−05 | 7.84E−05 | 4.94E−06 | 2.98E−05 | 2.28E−05 | 3.25E−05 |
| methanol | 2.01E−05 | 5.03E−05 | 3.18E−05 | 1.20E−05 | 4.36E−05 | 1.71E−05 |
| toluene | 4.12E−04 | 2.44E−04 | 1.78E−04 | 2.16E−04 | 1.77E−04 | 1.18E−04 |

TABLE 6-continued

|  | Exp 1 | Exp 3 | Exp 5 | Exp 2 | Exp 4 | Exp 6 |
| --- | --- | --- | --- | --- | --- | --- |
|  | 22° C. | 22° C. | 23° C. | 22° C. | 22° C. | 22° C. |
| AVERAGES Sensor 5 poly(4-vinyl phenol) (not heated) | | | | | | |
| 2-propanol | 3.31E−03 | 1.60E−03 | 2.56E−03 | 3.18E−03 | 2.44E−03 | 1.53E−03 |
| benzene | 5.11E−04 | 3.45E−04 | 4.77E−04 | 5.23E−04 | 4.47E−04 | 3.93E−04 |
| chloroform | 9.93E−04 | 6.38E−04 | 9.01E−04 | 1.05E−03 | 8.95E−04 | 5.96E−04 |
| cyclohexane | 1.32E−04 | 7.83E−05 | 9.96E−05 | 7.61E−05 | 8.85E−05 | 1.01E−04 |
| ethanol | 1.75E−02 | 1.33E−02 | 1.57E−02 | 1.67E−02 | 1.51E−02 | 1.27E−02 |
| hexane | 1.33E−04 | 1.05E−04 | 1.20E−04 | 1.74E−04 | 1.10E−04 | 1.07E−04 |
| methanol | 1.27E−02 | 1.15E−02 | 1.18E−02 | 1.23E−02 | 1.18E−02 | 1.11E−02 |
| toluene | 1.08E−03 | 7.02E−04 | 9.74E−04 | 1.08E−03 | 8.69E−04 | 6.69E−04 |
| STANDARD DEVIATION Sensor 5 poly(4-vinyl phenol) (not heated) | | | | | | |
| 2-propanol | 1.26E−04 | 7.17E−05 | 5.29E−05 | 7.47E−05 | 8.36E−05 | 1.09E−04 |
| benzene | 1.84E−05 | 2.92E−05 | 4.24E−05 | 4.00E−05 | 1.96E−05 | 2.42E−05 |
| chloroform | 6.73E−05 | 3.52E−05 | 2.11E−05 | 5.81E−05 | 2.35E−05 | 4.43E−05 |
| cyclohexane | 1.52E−05 | 3.30E−05 | 1.33E−05 | 5.11E−05 | 1.66E−05 | 6.08E−05 |
| ethanol | 5.63E−04 | 5.20E−04 | 1.40E−04 | 5.19E−04 | 3.34E−04 | 6.10E−04 |
| hexane | 3.54E−05 | 9.39E−06 | 2.96E−05 | 3.18E−05 | 3.84E−06 | 2.68E−05 |
| methanol | 5.31E−05 | 1.78E−04 | 1.50E−04 | 1.62E−04 | 9.92E−05 | 3.93E−04 |
| toluene | 5.06E−05 | 5.00E−05 | 9.14E−05 | 9.22E−05 | 4.81E−05 | 5.81E−06 |
|  | 22° C. | 22° C. | 23° C. | 22° C. | 22° C. | 22° C. |
| AVERAGES Sensor 7 poly(4-vinyl phenol) (not heated) | | | | | | |
| 2-propanol | 1.55E−03 | 2.49E−04 | 1.10E−03 | 1.47E−03 | 7.27E−04 | 2.63E−04 |
| benzene | 6.95E−04 | 2.83E−04 | 4.63E−04 | 4.46E−04 | 3.87E−04 | 3.08E−04 |
| chloroform | 5.86E−04 | 2.19E−04 | 4.86E−04 | 6.59E−04 | 3.87E−04 | 2.11E−04 |
| cyclohexane | 3.35E−04 | 8.02E−05 | 1.17E−04 | 1.61E−04 | 8.90E−05 | 1.43E−04 |
| ethanol | 1.20E−02 | 4.88E−03 | 1.06E−02 | 1.17E−02 | 8.79E−03 | 4.38E−03 |
| hexane | 1.84E−04 | 1.60E−04 | 2.16E−04 | 1.72E−04 | 1.57E−04 | 1.34E−04 |
| methanol | 1.09E−02 | 1.02E−02 | 1.10E−02 | 1.13E−02 | 1.29E−02 | 1.04E−02 |
| toluene | 1.06E−03 | 6.43E−04 | 9.00E−04 | 9.33E−04 | 7.33E−04 | 5.74E−04 |
| STANDARD DEVIATION Sensor 7 poly(4-vinyl phenol) (not heated) | | | | | | |
| 2-propanol | 1.36E−04 | 4.15E−05 | 8.21E−05 | 1.56E−04 | 5.48E−05 | 5.45E−05 |
| benzene | 1.16E−05 | 8.23E−05 | 8.53E−05 | 1.03E−04 | 8.77E−05 | 4.20E−05 |
| chloroform | 6.41E−05 | 1.21E−04 | 7.59E−05 | 1.31E−04 | 1.36E−04 | 3.63E−05 |
| cyclohexane | 4.14E−05 | 3.62E−05 | 5.71E−05 | 6.57E−05 | 3.68E−05 | 8.23E−05 |
| ethanol | 8.41E−05 | 4.75E−04 | 2.43E−04 | 4.28E−04 | 5.34E−04 | 2.41E−04 |
| hexane | 1.12E−04 | 5.94E−05 | 9.81E−05 | 2.63E−05 | 4.34E−05 | 6.98E−05 |
| methanol | 1.97E−04 | 5.53E−04 | 2.48E−04 | 3.93E−04 | 5.12E−04 | 2.80E−04 |
| toluene | 8.16E−05 | 8.98E−05 | 9.25E−05 | 3.72E−05 | 8.43E−05 | 7.97E−05 |
|  | 22° C. | 22° C. | 23° C. | 45° C. | 46° C. | 64° C. |
| AVERAGES Sensor 18 poly(4-vinyl phenol) | | | | | | |
| 2-propanol | 7.57E−04 | 1.57E−03 | 9.23E−04 | 2.45E−03 | 1.42E−03 | 4.89E−03 |
| benzene | 3.58E−04 | 2.91E−03 | 2.76E−03 | 1.12E−03 | 3.35E−03 | 2.62E−03 |
| chloroform | 3.12E−03 | 6.87E−03 | 2.50E−03 | 3.91E−03 | 1.73E−03 | 4.88E−03 |
| cyclohexane | 2.72E−03 | 8.70E−03 | 1.27E−03 | 1.67E−03 | 2.42E−03 | 3.45E−03 |
| ethanol | 4.83E−03 | 4.53E−03 | 5.14E−03 | 1.50E−02 | 1.81E−02 | 1.03E−02 |
| hexane | 1.81E−03 | 3.69E−03 | 1.27E−03 | 3.42E−03 | 2.12E−03 | 5.06E−03 |
| methanol | 3.18E−02 | 1.77E−02 | 3.93E−02 | 2.54E−02 | 3.42E−02 | 1.20E−02 |
| toluene | 3.89E−03 | 2.17E−03 | 1.16E−03 | −9.19E−04 | 3.59E−03 | 2.81E−03 |
| STANDARD DEVIATION Sensor 18 poly(4-vinyl phenol) | | | | | | |
| 2-propanol | 4.19E−04 | 2.50E−03 | 4.77E−04 | 9.88E−04 | 2.29E−03 | 3.09E−03 |
| benzene | 3.18E−03 | 3.65E−03 | 1.91E−03 | 2.53E−03 | 1.78E−04 | 1.98E−03 |
| chloroform | 2.20E−03 | 3.96E−04 | 1.63E−03 | 3.21E−03 | 1.08E−03 | 7.30E−03 |
| cyclohexane | 2.31E−03 | 1.17E−02 | 1.56E−03 | 4.69E−03 | 8.68E−04 | 1.71E−03 |
| ethanol | 1.61E−03 | 2.37E−03 | 9.72E−04 | 2.33E−03 | 2.40E−03 | 9.56E−03 |
| hexane | 1.01E−03 | 2.80E−03 | 6.31E−04 | 1.70E−03 | 8.44E−04 | 1.95E−03 |
| methanol | 8.72E−03 | 5.25E−03 | 1.23E−03 | 1.11E−02 | 4.57E−03 | 5.97E−03 |
| toluene | 3.90E−03 | 5.32E−03 | 9.34E−04 | 3.75E−03 | 1.47E−03 | 2.99E−04 |
|  | 22° C. | 22° C. | 23° C. | 37° C. | 38° C. | 43° C. |
| AVERAGES Sensor 19 poly(4-vinyl phenol) | | | | | | |
| 2-propanol | 9.09E−04 | 2.38E−04 | 1.86E−04 | 1.02E−03 | 2.74E−04 | 1.72E−04 |
| benzene | 2.32E−04 | 2.14E−04 | 2.22E−04 | 2.58E−04 | 1.52E−04 | 1.28E−04 |
| chloroform | 3.91E−04 | 1.31E−04 | 1.69E−04 | 3.29E−04 | 1.76E−04 | 8.66E−05 |
| cyclohexane | 1.31E−04 | 8.34E−05 | 1.16E−04 | 4.71E−05 | 7.94E−05 | 1.25E−04 |

TABLE 6-continued

|  | Exp 1 | Exp 3 | Exp 5 | Exp 2 | Exp 4 | Exp 6 |
|---|---|---|---|---|---|---|
| ethanol | 1.09E−02 | 6.48E−03 | 5.48E−03 | 7.68E−03 | 4.81E−03 | 2.38E−03 |
| hexane | 8.28E−05 | 9.80E−05 | 1.03E−04 | 4.48E−05 | 7.25E−05 | 1.66E−04 |
| methanol | 1.06E−02 | 9.98E−03 | 9.23E−03 | 6.73E−03 | 5.82E−03 | 4.04E−03 |
| toluene | 4.57E−04 | 4.10E−04 | 4.62E−04 | 3.51E−04 | 2.17E−04 | 1.62E−04 |

STANDARD DEVIATION Sensor 19 poly(4-vinyl phenol)

|  | Exp 1 | Exp 3 | Exp 5 | Exp 2 | Exp 4 | Exp 6 |
|---|---|---|---|---|---|---|
| 2-propanol | 1.62E−05 | 4.38E−05 | 6.09E−05 | 5.69E−05 | 1.25E−04 | 8.61E−05 |
| benzene | 1.60E−05 | 7.93E−05 | 6.85E−05 | 1.43E−04 | 4.41E−05 | 2.55E−05 |
| cchloroform | 6.82E−05 | 2.86E−05 | 1.82E−05 | 2.95E−05 | 9.03E−05 | 3.69E−05 |
| cyclohexane | 1.32E−05 | 4.94E−05 | 7.90E−05 | 6.32E−05 | 3.30E−05 | 3.08E−05 |
| ethanol | 5.51E−04 | 5.99E−04 | 3.17E−05 | 7.08E−04 | 5.44E−04 | 4.33E−04 |
| hexane | 4.84E−05 | 6.92E−06 | 3.30E−05 | 9.91E−05 | 1.03E−05 | 7.23E−05 |
| methanol | 2.21E−04 | 4.53E−04 | 1.04E−04 | 5.95E−04 | 2.21E−04 | 3.94E−04 |
| toluene | 9.02E−05 | 2.26E−05 | 1.02E−04 | 1.68E−05 | 1.38E−04 | 1.72E−04 |

TABLE 7

|  | Exp 1 | Exp 3 | Exp 5 | Exp 2 | Exp 4 | Exp 6 |
|---|---|---|---|---|---|---|
|  | 22° C. | 22° C. | 23° C. | 22° C. | 22° C. | 22° C. |

Normalized Sensor 3 poly(ethylene-vinyl acetate) (not heated) averages

|  | Exp 1 | Exp 3 | Exp 5 | Exp 2 | Exp 4 | Exp 6 |
|---|---|---|---|---|---|---|
| 2-propanol | 3.67E−02 | 3.69E−02 | 3.73E−02 | 3.63E−02 | 3.80E−02 | 3.82E−02 |
| benzene | 1.27E−01 | 1.28E−01 | 1.27E−01 | 1.29E−01 | 1.27E−01 | 1.29E−01 |
| chloroform | 1.15E−01 | 1.13E−01 | 1.16E−01 | 1.18E−01 | 1.14E−01 | 1.16E−01 |
| cyclohexane | 1.03E−01 | 1.03E−01 | 1.04E−01 | 1.02E−01 | 1.03E−01 | 1.05E−01 |
| ethanol | 2.70E−02 | 2.76E−02 | 2.73E−02 | 2.77E−02 | 2.73E−02 | 2.77E−02 |
| hexane | 5.97E−02 | 5.63E−02 | 5.67E−02 | 5.99E−02 | 5.75E−02 | 5.72E−02 |
| methanol | 6.71E−03 | 6.76E−03 | 6.89E−03 | 8.42E−03 | 7.37E−03 | 6.74E−03 |
| toluene | 5.25E−01 | 5.28E−01 | 5.25E−01 | 5.19E−01 | 5.25E−01 | 5.21E−01 |

Normalized Sensor 3 poly(ethylene-vinyl acetate) (not heated)
STANDARD DEVIATION

|  | Exp 1 | Exp 3 | Exp 5 | Exp 2 | Exp 4 | Exp 6 |
|---|---|---|---|---|---|---|
| 2-propanol | 2.66E−03 | 7.46E−04 | 3.37E−04 | 2.26E−03 | 7.96E−04 | 2.75E−03 |
| benzene | 4.25E−03 | 2.31E−03 | 1.52E−03 | 2.12E−03 | 1.07E−03 | 4.98E−03 |
| chloroform | 5.44E−03 | 4.04E−03 | 2.12E−03 | 1.32E−03 | 3.03E−03 | 8.57E−03 |
| cyclohexane | 6.89E−03 | 1.84E−03 | 7.68E−04 | 1.33E−03 | 2.04E−03 | 2.64E−03 |
| ethanol | 2.11E−03 | 9.77E−05 | 7.85E−04 | 9.72E−04 | 1.21E−04 | 2.07E−03 |
| hexane | 1.58E−03 | 1.99E−03 | 1.76E−03 | 3.26E−03 | 9.29E−04 | 2.63E−03 |
| methanol | 8.81E−04 | 1.80E−04 | 7.15E−04 | 2.22E−03 | 5.73E−04 | 1.58E−03 |
| toluene | 1.60E−02 | 2.29E−03 | 3.84E−03 | 5.82E−03 | 1.41E−03 | 1.44E−02 |

|  | 22° C. | 22° C. | 23° C. | 22° C. | 22° C. | 22° C. |
|---|---|---|---|---|---|---|

Normalized Sensor 8 poly(ethylene-vinyl acetate) (not heated) averages

|  | Exp 1 | Exp 3 | Exp 5 | Exp 2 | Exp 4 | Exp 6 |
|---|---|---|---|---|---|---|
| 2-propanol | 3.97E−02 | 4.02E−02 | 4.01E−02 | 3.91E−02 | 4.10E−02 | 4.13E−02 |
| benzene | 1.26E−01 | 1.27E−01 | 1.28E−01 | 1.28E−01 | 1.27E−01 | 1.28E−01 |
| chloroform | 1.16E−01 | 1.15E−01 | 1.17E−01 | 1.19E−01 | 1.16E−01 | 1.18E−01 |
| cyclohexane | 1.02E−01 | 1.01E−01 | 1.02E−01 | 1.02E−01 | 1.01E−01 | 1.02E−01 |
| ethanol | 2.93E−02 | 3.00E−02 | 2.91E−02 | 2.96E−02 | 2.94E−02 | 3.01E−02 |
| hexane | 5.79E−02 | 5.48E−02 | 5.61E−02 | 5.90E−02 | 5.60E−02 | 5.53E−02 |
| methanol | 8.20E−03 | 7.71E−03 | 8.14E−03 | 8.01E−03 | 8.37E−03 | 8.10E−03 |
| toluene | 5.21E−01 | 5.25E−01 | 5.20E−01 | 5.16E−01 | 5.22E−01 | 5.17E−01 |

Normalized Sensor 8 poly(ethylene-vinyl (not heated)
STANDARD DEVIATION

|  | Exp 1 | Exp 3 | Exp 5 | Exp 2 | Exp 4 | Exp 6 |
|---|---|---|---|---|---|---|
| 2-propanol | 3.03E−03 | 5.54E−04 | 3.15E−04 | 1.98E−03 | 5.01E−04 | 3.08E−03 |
| benzene | 4.33E−03 | 1.74E−03 | 2.12E−03 | 2.65E−04 | 8.33E−04 | 6.15E−03 |
| chloroform | 6.34E−03 | 3.74E−03 | 2.54E−03 | 2.46E−03 | 4.2iE−03 | 8.12E−03 |
| cyclohexane | 5.86E−03 | 1.16E−03 | 1.19E−03 | 1.25E−03 | 2.70E−03 | 3.18E−03 |
| ethanol | 2.13E−03 | 1.19E−04 | 4.98E−04 | 1.41E−03 | 2.40E−04 | 2.32E−03 |
| hexane | 2.45E−04 | 2.73E−03 | 1.81E−03 | 1.56E−03 | 1.31E−03 | 2.36E−03 |
| methanol | 1.18E−03 | 6.21E−04 | 8.73E−04 | 1.03E−03 | 8.06E−04 | 1.73E−03 |
| toluene | 1.62E−02 | 3.54E−03 | 5.20E−03 | 5.53E−03 | 2.06E−03 | 1.42E−02 |

TABLE 7-continued

| | Exp 1 | Exp 3 | Exp 5 | Exp 2 | Exp 4 | Exp 6 |
|---|---|---|---|---|---|---|
| | 22° C. | 22° C. | 23° C. | 45° C. | 46° C. | 55° C. |
| Normalized Sensor 17 poly(ethylene-vinyl acetate) averages | | | | | | |
| 2-propanol | 4.10E−02 | 4.17E−02 | 4.13E−02 | 2.05E−02 | 4.72E−02 | 3.52E−02 |
| benzene | 1.28E−01 | 1.30E−01 | 1.31E−01 | 8.31E−02 | 1.15E−01 | 1.06E−01 |
| chloroform | 1.20E−01 | 1.18E−01 | 1.20E−01 | 1.09E−01 | 1.17E−01 | 8.71E−02 |
| cyclohexane | 1.08E−01 | 1.07E−01 | 1.08E−01 | 1.35E−01 | 1.54E−01 | 1.29E−01 |
| ethanol | 2.86E−02 | 3.02E−02 | 2.91E−02 | 2.28E−02 | 3.43E−02 | 2.43E−02 |
| hexane | 6.18E−02 | 5.79E−02 | 5.85E−02 | 8.87E−02 | 7.79E−02 | 1.00E−01 |
| methanol | 7.78E−03 | 7.71E−03 | 7.70E−03 | 2.53E−03 | 3.87E−02 | 1.23E−02 |
| toluene | 5.04E−01 | 5.07E−01 | 5.05E−01 | 5.37E−01 | 4.16E−01 | 5.06E−01 |
| Normalized Sensor 17 poly(ethylene-vinyl acetate) STANDARD DEVIATION | | | | | | |
| 2-propanol | 3.52E−03 | 1.12E−03 | 3.46E−04 | 2.94E−02 | 1.45E−02 | 1.90E−02 |
| benzene | 5.81E−03 | 1.97E−03 | 2.33E−03 | 8.94E−02 | 3.01E−02 | 2.11E−02 |
| chloroform | 7.22E−03 | 4.96E−03 | 2.66E−03 | 1.20E−02 | 1.27E−02 | 2.47E−02 |
| cyclohexane | 7.49E−03 | 3.11E−03 | 1.37E−03 | 2.48E−04 | 2.12E−02 | 2.10E−02 |
| ethanol | 2.44E−03 | 7.09E−04 | 5.26E−04 | 8.40E−03 | 7.16E−03 | 1.55E−02 |
| hexane | 1.58E−03 | 3.23E−04 | 1.67E−03 | 1.68E−03 | 9.06E−04 | 5.47E−03 |
| methanol | 1.11E−03 | 6.06E−04 | 9.22E−04 | 6.36E−03 | 5.94E−02 | 2.04E−02 |
| toluene | 1.74E−02 | 5.77E−03 | 5.71E−03 | 2.11E−01 | 1.42E−02 | 4.10E−01 |

| | 22° C. | 22° C. | 23° C. | 33° C. | 34° C. | 37° C. |
|---|---|---|---|---|---|---|
| Normalized Sensor 20 poly(ethylene-vinyl acetate) averages | | | | | | |
| 2-propanol | 4.31E−02 | 4.35E−02 | 4.35E−02 | 4.08E−02 | 4.42E−02 | 4.60E−02 |
| benzene | 1.23E−01 | 1.26E−01 | 1.25E−01 | 1.33E−01 | 1.25E−01 | 1.36E−01 |
| chloroform | 1.20E−01 | 1.18E−01 | 1.19E−01 | 1.21E−01 | 1.16E−01 | 1.17E−01 |
| cyclohexane | 1.07E−01 | 1.07E−01 | 1.07E−01 | 1.18E−01 | 1.15E−01 | 1.21E−01 |
| ethanol | 3.10E−02 | 3.27E−02 | 3.08E−02 | 3.18E−02 | 3.73E−02 | 3.63E−02 |
| hexane | 6.07E−02 | 5.72E−02 | 5.79E−02 | 6.68E−02 | 6.64E−02 | 6.26E−02 |
| methanol | 9.39E−03 | 9.17E−03 | 8.99E−03 | 9.69E−03 | 1.43E−02 | 1.12E−02 |
| toluene | 5.06E−01 | 5.06E−01 | 5.07E−01 | 4.79E−01 | 4.81E−01 | 4.69E−01 |
| Normalized Sensor 20 poly(ethylene-vinyl acetate) STANDARD DEVIATION | | | | | | |
| 2-propanol | 3.26E−03 | 8.09E−04 | 4.41E−04 | 3.24E−03 | 2.30E−03 | 1.05E−02 |
| benzene | 5.36E−03 | 1.89E−03 | 2.72E−03 | 1.03E−02 | 6.27E−03 | 1.04E−02 |
| chloroform | 6.77E−03 | 4.09E−03 | 2.90E−03 | 3.51E−03 | 5.03E−03 | 9.04E−03 |
| cyclohexane | 7.25E−03 | 2.18E−03 | 1.63E−03 | 5.10E−03 | 1.29E−03 | 1.34E−02 |
| ethanol | 2.45E−03 | 1.51E−04 | 5.88E−04 | 1.44E−03 | 5.03E−03 | 7.77E−03 |
| hexane | 1.93E−03 | 2.64E−03 | 1.54E−03 | 2.09E−03 | 2.17E−03 | 6.38E−03 |
| methanol | 6.49E−04 | 5.80E−04 | 2.81E−04 | 1.44E−03 | 1.40E−02 | 6.22E−03 |
| toluene | 1.98E−02 | 4.35E−03 | 5.95E−03 | 2.72E−02 | 7.90E−03 | 1.86E−02 |

| | 22° C. | 22° C. | 23° C. | 22° C. | 22° C. | 22° C. |
|---|---|---|---|---|---|---|
| Normalized Sensor 4 poly(ethylene oxide) (not heated) averages | | | | | | |
| 2-propanol | 6.06E−02 | 6.34E−02 | 6.16E−02 | 6.05E−02 | 6.18E−02 | 6.38E−02 |
| benzene | 1.48E−01 | 1.47E−01 | 1.49E−01 | 1.50E−01 | 1.48E−01 | 1.47E−01 |
| chloroform | 1.42E−01 | 1.44E−01 | 1.43E−01 | 1.46E−01 | 1.43E−01 | 1.45E−01 |
| cyclohexane | 1.69E−02 | 1.63E−02 | 1.70E−02 | 1.66E−02 | 1.65E−02 | 1.65E−02 |
| ethanol | 5.66E−02 | 5.89E−02 | 5.77E−02 | 5.62E−02 | 5.74E−02 | 5.85E−02 |
| hexane | 1.27E−02 | 1.14E−02 | 1.26E−02 | 1.25E−02 | 1.22E−02 | 1.22E−02 |
| methanol | 2.69E−02 | 2.76E−02 | 2.74E−02 | 2.68E−02 | 2.72E−02 | 2.80E−02 |
| toluene | 5.36E−01 | 5.31E−01 | 5.32E−01 | 5.32E−01 | 5.34E−01 | 5.29E−01 |
| Normalizod Sensor 4 poly(ethylene oxide) (not heated) STANDARD DEVIATION | | | | | | |
| 2-propanol | 2.28E−03 | 1.24E−03 | 6.36E−04 | 2.06E−04 | 1.27E−04 | 2.26E−03 |
| benzene | 4.22E−03 | 4.61E−03 | 1.32E−03 | 1.94E−04 | 1.30E−03 | 3.51E−03 |
| chloroform | 6.22E−03 | 7.31E−03 | 2.71E−03 | 2.29E−03 | 4.33E−03 | 5.76E−03 |
| cyclohexane | 3.11E−04 | 1.05E−03 | 3.37E−06 | 1.51E−04 | 3.40E−04 | 3.55E−04 |
| ethanol | 2.53E−03 | 2.74E−04 | 4.01E−04 | 4.21E−04 | 5.31E−04 | 2.68E−03 |
| hexane | 2.48E−04 | 1.39E−03 | 6.69E−05 | 5.57E−05 | 2.66E−04 | 4.18E−04 |
| methanol | 4.06E−04 | 4.45E−04 | 4.64E−04 | 3.70E−04 | 2.29E−04 | 9.06E−04 |
| toluene | 7.97E−03 | 2.34E−03 | 3.23E−03 | 4.07E−03 | 1.62E−03 | 7.97E−03 |

TABLE 7-continued

|  | Exp 1 | Exp 3 | Exp 5 | Exp 2 | Exp 4 | Exp 6 |
| --- | --- | --- | --- | --- | --- | --- |
|  | 22° C. | 22° C. | 23° C. | 22° C. | 22° C. | 22° C. |
| Normalized Sensor 6 poly(ethylene oxide) (not heated) averages | | | | | | |
| 2-propanol | 5.53E−02 | 5.86E−02 | 5.65E−02 | 5.53E−02 | 5.69E−02 | 5.86E−02 |
| benzene | 1.53E−01 | 1.50E−01 | 1.53E−01 | 1.55E−01 | 1.53E−01 | 1.51E−01 |
| chloroform | 1.40E−01 | 1.42E−01 | 1.41E−01 | 1.43E−01 | 1.40E−01 | 1.43E−01 |
| cyclohexane | 1.75E−02 | 1.63E−02 | 1.76E−02 | 1.72E−02 | 1.70E−02 | 1.72E−02 |
| ethanol | 4.98E−02 | 5.28E−02 | 5.10E−02 | 4.97E−02 | 5.14E−02 | 5.24E−02 |
| hexane | 1.39E−02 | 1.16E−02 | 1.35E−02 | 1.35E−02 | 1.29E−02 | 1.32E−02 |
| methanol | 2.36E−02 | 2.46E−02 | 2.43E−02 | 2.36E−02 | 2.41E−02 | 2.49E−02 |
| toluene | 5.47E−01 | 5.44E−01 | 5.43E−01 | 5.43E−01 | 5.45E−01 | 5.40E−01 |
| Normalized Sensor 6 poly(ethylene oxide) (not heated) STANDARD DEVIATION | | | | | | |
| 2-propanol | 2.36E−03 | 1.76E−03 | 6.15E−04 | 3.46E−04 | 2.65E−04 | 2.42E−03 |
| benzene | 4.47E−03 | 8.71E−03 | 1.36E−03 | 2.59E−04 | 1.63E−03 | 3.91E−03 |
| chloroform | 6.22E−03 | 9.18E−03 | 2.66E−03 | 2.20E−03 | 4.88E−03 | 5.88E−03 |
| cyclohexane | 3.90E−04 | 1.73E−03 | 1.23E−04 | 2.53E−04 | 4.51E−04 | 4.35E−04 |
| ethanol | 2.23E−03 | 7.86E−04 | 4.03E−04 | 2.16E−04 | 2.87E−04 | 2.47E−03 |
| hexane | 9.70E−05 | 2.27E−03 | 1.43E−04 | 1.06E−04 | 3.53E−04 | 3.45E−04 |
| methanol | 4.47E−04 | 7.32E−04 | 4.36E−04 | 2.54E−04 | 2.25E−04 | 9.89E−04 |
| toluene | 7.87E−03 | 8.31E−03 | 2.69E−03 | 4.53E−03 | 2.34E−03 | 8.03E−03 |
|  | 22° C. | 22° C. | 23° C. | 22° C. | 22° C. | 22° C. |
| Normalized Sensor 9 poly(ethylene oxide) (not heated) averages | | | | | | |
| propanol | 7.33E−02 | 8.62E−02 | 7.74E−02 | 7.45E−02 | 7.72E−02 | 9.14E−02 |
| benzene | 1.43E−01 | 1.42E−01 | 1.43E−01 | 1.44E−01 | 1.41E−01 | 1.38E−01 |
| chloroform | 1.50E−01 | 1.55E−01 | 1.52E−01 | 1.54E−01 | 1.55E−01 | 1.58E−01 |
| cyclohexane | 1.78E−02 | 2.23E−02 | 1.78E−02 | 1.72E−02 | 1.74E−02 | 1.78E−02 |
| ethanol | 6.89E−02 | 7.93E−02 | 6.97E−02 | 6.73E−02 | 7.28E−02 | 8.01E−02 |
| hexane | 1.24E−02 | 2.00E−02 | 1.26E−02 | 1.33E−02 | 1.25E−02 | 1.49E−02 |
| methanol | 3.42E−02 | 4.32E−02 | 3.39E−02 | 3.43E−02 | 3.78E−02 | 4.32E−02 |
| toluene | 5.01E−01 | 4.52E−01 | 4.93E−01 | 4.95E−01 | 4.86E−01 | 4.57E−01 |
| Normalized Sensor 9 poly(ethylene oxide) (not heated) STANDARD DEVIATION | | | | | | |
| 2-propanol | 3.67E−03 | 3.73E−03 | 1.64E−03 | 6.77E−04 | 2.83E−03 | 1.00E−02 |
| benzene | 5.16E−03 | 1.20E−02 | 3.16E−03 | 2.47E−03 | 9.94E−04 | 2.41E−03 |
| chloroform | 4.69E−03 | 3.34E−03 | 1.32E−03 | 1.44E−03 | 3.40E−03 | 1.08E−02 |
| cyclohexane | 1.15E−03 | 4.09E−03 | 7.89E−04 | 2.21E−03 | 2.41E−04 | 1.01E−03 |
| ethanol | 3.94E−03 | 5.11E−03 | 3.86E−04 | 1.37E−03 | 4.78E−04 | 4.93E−03 |
| hexane | 1.90E−03 | 6.97E−03 | 1.12E−03 | 1.10E−03 | 4.08E−03 | 4.35E−03 |
| methanol | 1.72E−03 | 2.46E−03 | 6.74E−04 | 1.25E−03 | 2.04E−03 | 3.49E−03 |
| toluene | 9.70E−03 | 8.90E−03 | 1.91E−03 | 6.27E−03 | 1.07E−02 | 8.81E−03 |
|  | 22° C. | 22° C. | 23° C. | 44° C. | 47° C. | 57° C. |
| Normalized Sensor 15 poly(ethylene oxide) averages | | | | | | |
| 2-propanol | 1.18E−01 | 1.22E−01 | 1.22E−01 | 9.01E−02 | 1.14E−01 | 9.98E−02 |
| benzene | 1.21E−01 | 1.27E−01 | 1.20E−01 | 1.14E−01 | 1.43E−01 | 1.06E−01 |
| chloroform | 1.52E−01 | 1.52E−01 | 1.51E−01 | 1.37E−01 | 1.48E−01 | 1.15E−01 |
| cyclohexane | 2.39E−02 | 3.53E−02 | 2.62E−02 | 1.69E−02 | 4.46E−02 | 5.62E−02 |
| ethanol | 1.09E−01 | 1.15E−01 | 1.11E−01 | 9.78E−02 | 9.05E−02 | 1.14E−01 |
| hexane | 1.84E−02 | 2.83E−02 | 1.92E−02 | 3.02E−02 | 3.23E−02 | 2.34E−02 |
| methanol | 5.54E−02 | 6.39E−02 | 5.71E−02 | 5.17E−02 | 4.85E−02 | 7.93E−02 |
| toluene | 4.02E−01 | 3.56E−01 | 3.93E−01 | 4.63E−01 | 3.79E−01 | 4.06E−01 |
| Normalized Sensor 15 poly(ethylene oxide) STANDARD DEVIATION | | | | | | |
| 2-propanol | 3.12E−03 | 1.56E−03 | 1.68E−03 | 3.25E−02 | 7.71E−03 | 3.05E−02 |
| benzene | 9.84E−04 | 1.82E−02 | 2.67E−03 | 4.78E−02 | 1.81E−02 | 8.01E−02 |
| chloroform | 4.71E−03 | 7.72E−03 | 1.23E−03 | 2.09E−02 | 1.10E−02 | 3.47E−02 |
| cyclohexane | 1.14E−03 | 4.95E−03 | 5.91E−03 | 6.16E−03 | 2.33E−02 | 7.55E−02 |
| ethanol | 3.63E−03 | 6.63E−03 | 6.06E−03 | 1.02E−02 | 1.08E−02 | 6.71E−02 |
| hexane | 3.46E−03 | 3.94E−03 | 5.55E−04 | 3.68E−02 | 1.44E−02 | 1.16E−02 |
| methanol | 3.27E−03 | 1.48E−03 | 5.57E−03 | 9.42E−03 | 1.56E−02 | 4.16E−02 |
| toluene | 5.22E−03 | 1.49E−02 | 4.32E−03 | 9.75E−03 | 1.71E−02 | 7.70E−02 |

TABLE 7-continued

|  | Exp 1 | Exp 3 | Exp 5 | Exp 2 | Exp 4 | Exp 6 |
| --- | --- | --- | --- | --- | --- | --- |
|  | 22° C. | 22° C. | 23° C. | 33° C. | 33° C. | 37° C. |
| Normalized Sensor 16 poly(ethylene oxide) averages | | | | | | |
| 2-propanol | 6.88E−02 | 7.87E−02 | 7.22E−02 | 6.11E−02 | 6.60E−02 | 6.75E−02 |
| benzene | 1.45E−01 | 1.42E−01 | 1.46E−01 | 1.51E−01 | 1.50E−01 | 1.47E−01 |
| chloroform | 1.48E−01 | 1.52E−01 | 1.51E−01 | 1.39E−01 | 1.41E−01 | 1.38E−01 |
| cyclohexane | 1.53E−02 | 1.73E−02 | 1.55E−02 | 1.72E−02 | 1.78E−02 | 2.06E−02 |
| ethanol | 6.26E−02 | 7.29E−02 | 6.54E−02 | 5.69E−02 | 6.03E−02 | 6.38E−02 |
| hexane | 9.63E−03 | 1.33E−02 | 1.07E−02 | 1.16E−02 | 1.28E−02 | 1.50E−02 |
| methanol | 3.00E−02 | 3.68E−02 | 3.11E−02 | 2.91E−02 | 3.09E−02 | 3.60E−02 |
| toluene | 5.21E−01 | 4.86E−01 | 5.08E−01 | 5.33E−01 | 5.21E−01 | 5.12E−01 |
| Normalized Sensor 16 poly(ethylene oxide) STANDARD DEVIATION | | | | | | |
| 2-propanol | 2.68E−03 | 2.04E−03 | 6.52E−04 | 1.39E−03 | 8.06E−04 | 2.45E−03 |
| benzene | 4.83E−03 | 4.29E−03 | 1.12E−03 | 1.31E−03 | 2.29E−03 | 5.57E−03 |
| chloroform | 7.22E−03 | 2.08E−03 | 2.94E−03 | 1.55E−03 | 2.29E−03 | 6.97E−03 |
| cyclohexane | 1.60E−04 | 1.86E−03 | 2.13E−04 | 1.39E−03 | 1.51E−03 | 8.98E−04 |
| ethanol | 2.89E−03 | 2.78E−03 | 3.73E−04 | 9.62E−04 | 4.09E−04 | 2.02E−03 |
| hexane | 4.86E−04 | 2.03E−03 | 1.21E−04 | 9.89E−04 | 8.28E−04 | 1.62E−03 |
| methanol | 4.58E−04 | 1.31E−03 | 7.76E−04 | 3.98E−04 | 1.58E−03 | 8.50E−04 |
| toluene | 9.39E−03 | 6.32E−03 | 4.35E−03 | 7.19E−03 | 6.42E−03 | 5.87E−03 |
|  | 22° C. | 22° C. | 23° C. | 22° C. | 22° C. | 22° C. |
| Normalized Sensor 5 poly(4-vinyl phenol) (not heated) averages | | | | | | |
| 2-propanol | 9.08E−02 | 5.67E−02 | 7.83E−02 | 9.08E−02 | 7.68E−02 | 5.63E−02 |
| benzene | 1.40E−02 | 1.22E−02 | 1.46E−02 | 1.49E−02 | 1.41E−02 | 1.45E−02 |
| chloroform | 2.73E−02 | 2.26E−02 | 2.76E−02 | 3.00E−02 | 2.82E−02 | 2.19E−02 |
| cyclohexane | 3.62E−03 | 2.77E−03 | 3.05E−03 | 2.17E−03 | 2.79E−03 | 3.72E−03 |
| ethanol | 4.81E−01 | 4.71E−01 | 4.81E−01 | 4.75E−01 | 4.77E−01 | 4.68E−01 |
| hexane | 3.65E−03 | 3.72E−03 | 3.67E−03 | 4.97E−03 | 3.45E−03 | 3.92E−03 |
| methanol | 3.50E−01 | 4.06E−01 | 3.62E−01 | 3.51E−01 | 3.71E−01 | 4.08E−01 |
| toluene | 2.98E−02 | 2.49E−02 | 2.98E−02 | 3.09E−02 | 2.73E−02 | 2.46E−02 |
| Normalized Sensor 5 poly(4-vinyl phenol) (not heated) STANDARD DEVIATION | | | | | | |
| 2-propanol | 3.47E−03 | 2.54E−03 | 1.62E−03 | 2.13E−03 | 2.63E−03 | 3.99E−03 |
| benzene | 5.06E−04 | 1.03E−03 | 1.30E−03 | 1.14E−03 | 6.17E−04 | 8.88E−04 |
| chloroform | 1.85E−03 | 1.25E−03 | 6.47E−04 | 1.66E−03 | 7.39E−04 | 1.63E−03 |
| cyclohexane | 4.16E−04 | 1.17E−03 | 4.08E−04 | 1.46E−03 | 5.21E−04 | 2.23E−03 |
| ethanol | 1.55E−02 | 1.84E−02 | 4.28E−03 | 1.48E−02 | 1.05E−02 | 2.24E−02 |
| hexane | 9.72E−04 | 3.32E−04 | 9.08E−04 | 9.08E−04 | 1.21E−04 | 9.83E−04 |
| methanol | 1.46E−03 | 6.28E−03 | 4.61E−03 | 4.63E−03 | 3.12E−03 | 1.44E−02 |
| toluene | 1.39E−03 | 1.77E−03 | 2.80E−03 | 2.63E−03 | 1.51E−03 | 2.14E−04 |
|  | 22° C. | 22° C. | 23° C. | 22° C. | 22° C. | 22° C. |
| Normalized Sensor 7 poly(4-vinyl phenol) (not heated) averages | | | | | | |
| 2-propanol | 5.69E−02 | 1.49E−02 | 4.41E−02 | 5.49E−02 | 3.01E−02 | 1.60E−02 |
| benzene | 2.55E−02 | 1.69E−02 | 1.86E−02 | 1.66E−02 | 1.61E−02 | 1.88E−02 |
| chloroform | 2.15E−02 | 1.31E−02 | 1.95E−02 | 2.46E−02 | 1.61E−02 | 1.29E−02 |
| cyclohexane | 1.23E−02 | 4.79E−03 | 4.71E−03 | 6.02E−03 | 3.69E−03 | 8.74E−03 |
| ethanol | 4.39E−01 | 2.91E−01 | 4.27E−01 | 4.35E−01 | 3.64E−01 | 2.67E−01 |
| hexane | 6.74E−03 | 9.58E−03 | 8.68E−03 | 6.40E−03 | 6.52E−03 | 8.15E−03 |
| methanol | 3.99E−01 | 6.11E−01 | 4.42E−01 | 4.22E−01 | 5.33E−01 | 6.33E−01 |
| toluene | 3.87E−02 | 3.84E−02 | 3.62E−02 | 3.48E−02 | 3.04E−02 | 3.50E−02 |
| Normalized Sensor 7 poly(4-vinyl phenol) (not heated) STANDARD DEVIATION | | | | | | |
| 2-propanol | 4.99E−03 | 2.48E−03 | 3.31E−03 | 5.81 E−03 | 2.27E−03 | 3.33E−03 |
| benzene | 4.26E−04 | 4.91E−03 | 3.43E−03 | 3.84E−03 | 3.64E−03 | 2.57E−03 |
| chloroform | 2.35E−03 | 7.22E−03 | 3.06E−03 | 4.90E−03 | 5.65E−03 | 2.22E−03 |
| cyclohexane | 1.52E−03 | 2.16E−03 | 2.30E−03 | 2.45E−03 | 1.53E−03 | 5.03E−03 |
| ethanol | 3.08E−02 | 2.83E−02 | 9.78E−03 | 1.60E−02 | 2.21E−02 | 1.47E−02 |
| hexane | 4.12E−03 | 3.55E−03 | 3.95E−03 | 9.80E−04 | 1.80E−03 | 4.26E−03 |
| methanol | 7.23E−03 | 3.30E−02 | 9.99E−03 | 1.47E−02 | 2.12E−02 | 1.71E−02 |
| toluene | 2.99E−03 | 5.36E−03 | 3.72E−03 | 1.39E−03 | 3.49E−03 | 4.87E−03 |

TABLE 7-continued

|  | Exp 1 | Exp 3 | Exp 5 | Exp 2 | Exp 4 | Exp 6 |
| --- | --- | --- | --- | --- | --- | --- |
|  | 22° C. | 22° C. | 23° C. | 45° C. | 46° C. | 64° C. |
| Normalized Sensor 18 poly(4-vinyl phenol) averages | | | | | | |
| 2-propanol | 1.53E−02 | 3.25E−02 | 1.70E−02 | 4.70E−02 | 2.80E−02 | 1.06E−01 |
| benzene | 7.26E−03 | 6.05E−02 | 5.08E−02 | 2.14E−02 | 6.61E−02 | 5.69E−02 |
| chloroform | 6.33E−02 | 1.43E−01 | 4.60E−02 | 7.52E−02 | 3.42E−02 | 1.06E−01 |
| cyclohexane | 5.52E−02 | 1.81E−01 | 2.34E−02 | 3.20E−02 | 4.77E−02 | 7.52E−02 |
| ethanol | 9.79E−02 | 9.42E−02 | 9.45E−02 | 2.89E−01 | 3.57E−02 | 2.24E−01 |
| hexane | 3.66E−02 | 7.66E−02 | 2.34E−02 | 6.56E−02 | 4.18E−02 | 1.10E−01 |
| methanol | 6.45E−01 | 3.68E−01 | 7.24E−01 | 4.88E−01 | 6.75E−01 | 2.60E−01 |
| toluene | 7.89E−02 | 4.50E−02 | 2.14E−02 | 1.77E−02 | 7.10E−02 | 6.11E−02 |
| Normalized Sensor 18 poly(4-vinyl phenol) STANDARD DEVIATION | | | | | | |
| 2-propanol | 8.51E−03 | 5.20E−02 | 8.77E−03 | 1.90E−02 | 4.51E−02 | 6.73E−02 |
| benzene | 6.45E−02 | 7.58E−02 | 3.51E−02 | 4.86E−02 | 3.51E−03 | 4.31E−02 |
| chloroform | 4.47E−02 | 8.22E−03 | 2.99E−02 | 6.17E−02 | 2.13E−02 | 1.59E−02 |
| cyclohexane | 4.68E−02 | 2.43E−01 | 2.87E−02 | 9.01E−02 | 1.71E−02 | 3.73E−02 |
| ethanol | 3.26E−02 | 4.93E−02 | 1.79E−02 | 4.47E−02 | 4.74E−02 | 2.08E−01 |
| hexane | 2.05E−02 | 5.81E−02 | 1.16E−02 | 3.26E−02 | 1.67E−02 | 4.25E−02 |
| methanol | 1.77E−01 | 1.09E−01 | 2.25E−02 | 2.14E−01 | 9.03E−02 | 1.30E−01 |
| toluene | 7.92E−02 | 1.11E−01 | 1.72E−02 | 7.21E−02 | 2.90E−02 | 6.50E−03 |
|  | 22° C. | 22° C. | 23° C. | 22° C. | 22° C. | 22° C. |
| Normalized Sensor 19 poly(4-vinyl phenol) averages | | | | | | |
| 2-propanol | 3.84E−02 | 1.35E−02 | 1.16E−02 | 6.17E−02 | 2.37E−02 | 2.38E−02 |
| benzene | 9.77E−03 | 1.21E−02 | 1.39E−02 | 1.57E−02 | 1.31E−02 | 1.77E−02 |
| chloroform | 1.65E−02 | 7.41E−03 | 1.06E−02 | 2.00E−02 | 1.52E−02 | 1.19E−02 |
| cyclohexane | 5.52E−03 | 4.73E−03 | 7.25E−03 | 2.86E−03 | 6.85E−03 | 1.72E−02 |
| ethanol | 4.62E−01 | 3.68E−01 | 3.43E−01 | 4.67E−01 | 4.15E−01 | 3.28E−01 |
| hexane | 3.50E−03 | 5.55E−03 | 6.42E−03 | 2.72E−03 | 6.25E−03 | 2.29E−02 |
| methanol | 4.46E−01 | 5.66E−01 | 5.78E−01 | 4.09E−01 | 5.02E−01 | 5.56E−01 |
| toluene | 1.93E−02 | 2.33E−02 | 2.89E−02 | 2.14E−02 | 1.87E−02 | 2.23E−02 |
| Normalized Sensor 19 poly(4-vinyl phenol) STANDARD DEVIATION | | | | | | |
| 2-propanol | 6.85E−04 | 2.48E−03 | 3.81E−03 | 3.46E−03 | 1.08E−02 | 1.19E−02 |
| benzene | 6.75E−04 | 4.50E−03 | 4.29E−03 | 8.71E−03 | 3.80E−03 | 3.52E−03 |
| chloroform | 2.88E−03 | 1.62E−03 | 1.14E−03 | 1.79E−03 | 7.79E−03 | 5.08E−03 |
| cyclohexane | 5.59E−04 | 2.50E−03 | 4.95E−03 | 3.84E−03 | 2.85E−03 | 4.25E−03 |
| ethanol | 2.33E−02 | 3.40E−02 | 1.98E−03 | 4.30E−02 | 4.69E−02 | 5.96E−02 |
| hexane | 2.04E−03 | 3.93E−04 | 2.07E−03 | 6.02E−03 | 8.91E−04 | 9.96E−03 |
| methanol | 9.31E−03 | 2.57E−02 | 6.54E−03 | 3.61E−02 | 1.90E−02 | 5.43E−02 |
| toluene | 3.81E−03 | 1.28E−03 | 6.39E−03 | 1.02E−03 | 1.19E−02 | 2.38E−02 |

The average ΔR/R values for exposures to the eight solvents are listed in Table 6 and are presented graphically in the various panels of FIG. 11. It can be seen that as the temperature increases, the over-all response of a given sensor decreases (in accord with the expected decrease in gas/polymer partition coefficient with increasing temperature). In addition, the error bars became larger at the higher temperatures as the signal became smaller relative to the noise.

Because of the differences in over-all height of the responses, the differences in response patterns between the room temperature data and the elevated temperature data are difficult to visualize from the plots of the absolute ΔR/R response of the sensor array. The patterns were, therefore, normalized by adding all the responses by a sensor to the eight solvents and dividing this sum by each response to a solvent. This normalization process highlights the differences in the pattern of responses at different temperatures rather than the over-all height differences. Table 7 and the various panels of FIG. 12 show the normalized patterns for the sensors.

In general, the fingerprints for the various vapors were similar at the different temperatures, but the magnitudes of the absolute responses were quite different. This implies that the characteristic "fingerprint" pattern of the analytes chosen in this study, for the sensor films investigated, were essentially invariant over the sensor materials and temperature range probed herein. This will be beneficial in many applications, (quality control of foodstuffs, process monitoring, etc.) in that identification of a vapor or (of its constancy in composition) over various exposures to the array, and classification of the vapor type in any given exposure, using the response pattern of the sensor output signals will not significantly depend on the temperature of the sensor array or of the analyte.

Quantitive analysis of the concentration of the analyte, would, however, require knowledge of the sensor temperature. This effect can be used to advantage in other potential applications of these sensor arrays, since lowering the temperature of an array element will in general increase the signal and therefore increase the sensitivity of the sensor to the desired analyte. Thus, a plurality of compositionally identical sensors, each held at a different temperature during a measurement period, could be used to produce signals above a threshold value at different concentrations of the vapor, thereby aiding in quantifying various ranges of the vapor concentration while still maintaining a linear concentration vs. vapor concentration response (in the small swelling regime) for an individual sensor. In addition, the differential response of compositionally identical sensors at various temperatures can be used to provide classification and identification information as the basis for the output signature of the sensor array. In general, combinations of compositionally different sensors at a plurality of different temperatures will produce a more desirable, more information-rich, data set from a given set of sensor materials than measurements at one fixed temperature, and can such arrays can therefore be usefully exploited for the purpose of detection, identification, and quantification, of a particular analyte. Such detection, identification and quantitiation may also be performed by employing a single resistor at a plurality of different temperatures.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying a chemical analyte, wherein said chemical analyte is a biomolecule, using a sensor array, said method comprising:
   (a) providing a sensor array, wherein each sensor comprises a conductive region and a nonconductive organic polymer region;
   (b) contacting said biomolecule with said sensor array to produce a response; and
   (c) analyzing said response thereby identifying said biomolecule.

2. A method according to claim 1, further comprising an electrical measuring apparatus.

3. A method according to claim 1, wherein said sensor array comprises about 10 to about 100 sensors.

4. A method according to claim 1, wherein said sensor array comprises about 1000 to about $10^6$ sensors.

5. A method according to claim 1, wherein said conductive region comprises an inorganic conductor.

6. A method according to claim 1, wherein said conductive region comprises an organic conductor.

7. A method according to claim 1, wherein said nonconductive organic polymer is a bio-polymer.

8. A method according to claim 7, wherein said bio-polymer is a carbohydrate.

9. A method according to claim 1, wherein said nonconductive organic polymer region in each sensor is compositionally different.

10. A method according to claim 1, wherein said conductive region in each sensor is compositionally different.

11. A method according to claim 1, wherein said biomolecule is identified by comparing said response to a database of response patterns for known biomolecules.

12. A sensor array for identification of a chemical analyte, wherein said analyte is a biomolecule, and wherein each sensor in said array comprises a conductive region and a nonconductive organic polymer region.

13. A sensor array according to claim 12, further comprising an electrical measuring apparatus.

14. A sensor array according to claim 12, wherein said sensor array is about 10 to about 100 sensors.

15. A sensor array according to claim 12, wherein said sensor array is about 1000 to about $10^6$ sensors.

16. A sensor array according to claim 12, wherein said conductive region comprises an inorganic conductor.

17. A sensor array according to claim 12, wherein said conductive region comprises an organic conductor.

18. A sensor array according to claim 12, wherein said nonconductive organic polymer region is a bio-polymer.

19. A sensor array according to claim 18, wherein said bio-polymer is a carbohydrate.

20. A sensor array according to claim 12, wherein said nonconductive organic polymer region in each sensor is compositionally different.

21. A sensor array according to claim 12, wherein said conductive region in each sensor is compositionally different.

22. A method for detecting the presence or level of a chemical analyte, wherein said analyte is a biomolecule, in a sample using a sensor array, said method comprising:
   (a) providing a sensor array, wherein each sensor comprises a conductive region and a nonconductive organic polymer region;
   (b) contacting said sample with said sensor array to produce a response; and
   (c) analyzing said response thereby detecting the presence and level of said biomolecule present in said sample.

23. A method according to claim 22, wherein the differential presence or level of said biomolecule in multiple samples is determined by comparing said responses of said samples.

* * * * *